US008106154B2

(12) United States Patent
Holmes et al.

(10) Patent No.: US 8,106,154 B2
(45) Date of Patent: Jan. 31, 2012

(54) NITROGEN-BASED LINKERS FOR ATTACHING MODIFYING GROUPS TO POLYPEPTIDES AND OTHER MACROMOLECULES

(75) Inventors: Christopher P. Holmes, Saratoga, CA (US); Anjan Chakrabarti, Gurgoan (IN); Brian T. Frederick, Ben Lomond, CA (US); Yijun Pan, Union City, CA (US); Yaohua S. Dong, San Francisco, CA (US); Ashok Bhandari, Cupertino, CA (US)

(73) Assignee: Affymax, Inc., Palo Alto, CA (US)

( * ) Notice: Subject to any disclaimer, the term of this patent is extended or adjusted under 35 U.S.C. 154(b) by 614 days.

(21) Appl. No.: 12/022,926

(22) Filed: Jan. 30, 2008

(65) Prior Publication Data
US 2009/0048147 A1    Feb. 19, 2009

Related U.S. Application Data

(60) Provisional application No. 60/898,868, filed on Jan. 31, 2007.

(51) Int. Cl.
C07K 7/02     (2006.01)
C07K 7/08     (2006.01)
C07K 14/505   (2006.01)
C07C 233/05   (2006.01)
C07C 229/04   (2006.01)
A61K 38/19    (2006.01)

(52) U.S. Cl. .................. 530/323; 530/388.23; 530/421; 562/567; 564/192; 514/7.7

(58) Field of Classification Search ........................ None
See application file for complete search history.

(56) References Cited

U.S. PATENT DOCUMENTS

| | | |
|---|---|---|
| 4,179,337 A | 12/1979 | Davis et al. |
| 5,654,276 A | 8/1997 | Barrett et al. |
| 5,668,110 A | 9/1997 | Barrett et al. |
| 5,672,662 A | 9/1997 | Harris et al. |
| 5,677,280 A | 10/1997 | Barrett et al. |
| 5,683,983 A | 11/1997 | Barrett et al. |
| 5,767,078 A | 6/1998 | Johnson et al. |
| 5,773,569 A | 6/1998 | Wrighton et al. |
| 5,830,851 A | 11/1998 | Wrighton et al. |
| 5,869,451 A | 2/1999 | Dower et al. |
| 5,932,546 A | 8/1999 | Barrett et al. |
| 5,986,047 A | 11/1999 | Wrighton et al. |
| 6,077,939 A | 6/2000 | Wei et al. |
| 6,083,913 A | 7/2000 | Dower et al. |
| 6,113,906 A | 9/2000 | Greenwald et al. |
| 6,121,238 A | 9/2000 | Dower et al. |
| 6,153,590 A | 11/2000 | Andersen et al. |
| 6,221,608 B1 | 4/2001 | Middleton et al. |
| 6,251,864 B1 | 6/2001 | Dower et al. |
| 6,333,031 B1 | 12/2001 | Olsson et al. |
| 6,465,430 B1 | 10/2002 | Dower et al. |
| 6,498,155 B1 | 12/2002 | Luengo et al. |
| 6,506,362 B1 | 1/2003 | Dower et al. |
| 6,552,008 B1 | 4/2003 | Duffy et al. |
| 6,858,630 B2 | 2/2005 | Luengo et al. |
| 7,084,245 B2 | 8/2006 | Holmes et al. |
| 2002/0015691 A1 | 2/2002 | Greenwald et al. |
| 2002/0160013 A1 | 10/2002 | Olsson et al. |
| 2002/0177166 A1 | 11/2002 | Guthridge et al. |
| 2003/0009018 A1 | 1/2003 | Maeda et al. |
| 2005/0107297 A1 | 5/2005 | Holmes et al. |
| 2007/0032408 A1 | 2/2007 | Holmes et al. |

FOREIGN PATENT DOCUMENTS

| | | |
|---|---|---|
| EP | 0401384 | 12/1990 |
| WO | WO-90/12874 | 11/1990 |
| WO | WO-92/16555 | 10/1992 |
| WO | WO-96/40189 | 12/1996 |
| WO | WO-96/40749 C1 | 12/1996 |
| WO | WO-96/40750 | 12/1996 |
| WO | WO-96/40772 C1 | 12/1996 |
| WO | WO-98/25965 | 6/1998 |
| WO | WO-00/02050 | 1/2000 |
| WO | WO-00/24770 | 5/2000 |
| WO | WO-00/24782 | 5/2000 |
| WO | WO-00/33881 | 6/2000 |
| WO | WO-01/38342 A2 | 5/2001 |
| WO | WO-01/917804 A1 | 12/2001 |
| WO | WO-02/065988 | 8/2002 |
| WO | WO-2004/014424 | 2/2004 |
| WO | WO-2004/101600 | 11/2004 |
| WO | WO-2004/101606 | 11/2004 |
| WO | WO-2004/101611 | 11/2004 |
| WO | WO-2004/108070 | 12/2004 |
| WO | WO 2006/062685 * | 6/2006 |

OTHER PUBLICATIONS

Lanigan RS, Yamarik TA, "Final report on the safety assessment of EDTA, Calcium disoidum EDTA, diammonium EDTA, dipotassium EDTA, disodium EDTA, TEA-EDTA, tetrasodium EDTA, tripotassium EDTA, trisodium EDTA, HEDTA, and trisodium HEDTA," International Journal of Toxicology, 2002, 21(Suppl 2): 95-142.*
Definition of moiety from http://dictionary.reference.com/browse/moiety, pp. 1-3. Accessed Aug. 25, 2010.*
Wrighton et al., "Increased Potency of an Erithropoietin Peptide Mimetic through Covalent Dimerization." Nature Biotechnology, Nature Publishing, US, vol. 15, (Nov. 1, 1997), pp. 1261-1265.
Greenwald et al., "Effective Drug Delivery by PEGylated Drug Conjugates", Advanced Drug Delivery Reviews. Amsterdam, NL. vol. 55, N. 2, pp. 217-250 (Feb. 10, 2003).
Greenwald et al., "Controlled Release of Proteins from their Poly-(ethylene glycol) Conjugates: Drg Delivery Systems Employing 1,6-elimination." Bioconjugate Chemistry. vol. 14, No. 2, pp. 395-403 (Apr. 3, 2003).
Abuchowski, A.,et al., "Effect of Covalent Attachment of Polyethylene Glycol on Immunogenicity and Circulating Life of Bovine Liver Catalase," J. Biol. Chem, vol. 252, pp. 3582-3586 (1977).
Beauchamp, C.O., et al., "A New Procedure for the Synthesis of Polytheylene Glycol-Protein Adducts; Effects on Function, Receptor Recognition, and Clearance of Superoxide Dismutase, Lactoferrin, and Alpha 2-Macroglobulin", Anal Biochem., vol. 131, pp. 25-33 (1983).

(Continued)

*Primary Examiner* — Julie Ha
(74) *Attorney, Agent, or Firm* — Fish & Richardson P.C.

(57) ABSTRACT

Compounds comprising a peptide moiety, a linker moiety and a water-soluble polymer moiety such as a poly(ethylene glycol) moiety are disclosed. Various linker moieties for use in these compounds are also disclosed, along methods for their synthesis.

4 Claims, 12 Drawing Sheets

OTHER PUBLICATIONS

Chen, R.H., et al., "Properties of Two Urate Oxidases Modified by the Covalent Attachment of Poly(ethylene glycol)", Biochem. Biophys. Acta., vol. 660, pp. 293-298 (1981).

Kita, Y., et al., "Characterization of a Polyethylene Glycol Conjugate of Recombinant Human Interferon-gamma", Dr. Des. Deliv. vol. 6, pp. 157-167 (1990).

Knauf, M.J., et al., "Relationship of Effective Molecular Size to Systemic Clearance in Rats of Recombinant Interleukin-2 Chemically Modified with Water-Soluble Polymers", J. Biol. Chem., vol. 263, pp. 15064-15070 (1988).

Tsutsumi, Y. et al., "Polyethylene Glycol Modification of Interleukin-6 Enhances its Thrombopoietic Activity", J. Controlled Release, vol. 33, pp. 447 (1995).

Wang et al: "1-(5-Cloro-2-alkoxyphenyl)-3-(5-cyano-pyrazi-2-y1) Ureas as Potent and Selective Inhibitors of Chk1 Kinase: Synthesis, Preliminary SAR, and Biological Activities" J. Med Chem. 2005, 48,3118-3121.

Jonhson et al.: "Advances in Nasal Drug Delivery through Tight Junction Technology" Expert Opin. Drug Deliv. (2005) 2(2): 281-298.

Francis et al.: "PEGylation of Cytokines and other Therapeutic Proteins and Peptides: The Importance of Biological Optimisation of Coupling Techniques" International Journal of Hematology 68 (1998) 1-18.

Goodson et al.: "Site-Directed PEGylation of Recombinant Interleukin-2 at its Glycosylation Site" Bio/Technology, vol. 8, Apr. 1990; 343-346.

Malik et al.: "Polyethylene Glycol (PEG)-modified Granulocyte-Macrophage Colony-stimulating Factor (GM-CSF) with Conserved Biological Activity" Exp. Hematol. 20:1028-1035 (1992).

Veronese et al.: "Surface Modifcation of Proteins; Activation of Monmethoxy-Polyethylene Glycols by Phenylchloroformates and Modification of Rionuclease and Superoxide Dismutase" Applied Biochemistry and Biotechnology; vol. 11 (1985); 141-152.

Schwarz et al.: "Enyzmatic C-Terminal Biotinylation of Proteins" Methods in Enzymology, vol. 184 (1990); pp. 160-162.

Rose et al.: "Preparation of Well-Defined Protein Conjugates Using Enzyme-Assisted Reverse Proteolysis" Bioconjugate Chem. 1991, 2, 154-159.

Gaertner et al.: "Chemo-enzmic Backbone Engineering of Proteins"; The Journal of Biological Chemistry; vol. 269, No. 10. pp. 7224-7230 (1994).

Felix et al.: "PEGylated Peptides IV; Enhanced Biological Activity of Site-directed PEGylated GRF Analogs" (1995) Int. J. Peptide Protein Res. vol. 46. pp. 253-264.

Zalipsky et al.: "Peptide Attachment to Extremities of Liposomal Surface Grafted PEG Chains: Preparation of the Long-Circulating Form of Laminin Pentapeptide, YIGSR" Bioconjugate Chem. 1995, vol. 6, pp. 705-708.

Abuchowski et al: "Soluble Polymer-Enzyme Adducts," in *Enzymes as Drugs*. Hocenberg and Roberts, eds. (Wiley-Interscience: New York, NY) pp. 367-383 (1981).

\* cited by examiner

NITROGEN-BASED LINKERS FOR ATTACHING MODIFYING GROUPS TO POLYPEPTIDES AND OTHER MACROMOLECULES

CROSS REFERENCE TO PRIOR APPLICATION

The present application claims the benefit under 35 U.S.C. §119(e), of U.S. Provisional Application No. 60/898,868, filed on Jan. 31, 2007, which is hereby incorporated herein by reference in its entirety.

FIELD OF THE INVENTION

The present invention relates to novel linker molecules that can covalently link two molecules while providing for covalent attachment of one or more modifying groups such as poly(ethylene glycol) (PEG). In addition, the invention relates to novel therapeutic compositions comprising such compounds.

BACKGROUND OF THE INVENTION

In recent years, with the development of research on proteins, a great number of peptides having various actions have been found. With the progress of genetic recombination techniques and organic synthetic methods of peptides, it has become possible to obtain these physiologically active peptides and their structurally analogous compounds in large amounts. Many of these peptides that have special activity are extremely useful as pharmaceuticals.

Examples of such peptides include peptides that bind to erythropoietin (EPO) receptors (EPO-R). EPO is a glycoprotein hormone with 165 amino acids, 4 glycosylation sites on amino acid positions 24, 38, 83, and 126, and a molecular weight of about 34,000. It stimulates mitotic division and the differentiation of erythrocyte precursor cells and thus ensures the production of erythrocytes. EPO is essential in the process of red blood cell formation, and the hormone has potentially useful applications in both the diagnosis and the treatment of blood disorders characterized by low or defective red blood cell production. A number of peptides that interact with the EPO-R have been discovered. (See, e.g., U.S. Pat. No. 5,773,569 to Wrighton et al.; U.S. Pat. No. 5,830,851 to Wrighton et al.; and WO 01/91780 to Smith-Swintosky et al.)

However, the clearance of peptides, particularly when administered in the circulatory system, is generally very fast. Therefore, it is desirable to improve the durability of such peptides. In addition, when the peptides are obtained from different species of animals, designed by peptide protein engineering, and/or having structures different from those of the subject, there is a risk of causing serious symptoms due to the production of antibodies. Hence, it is also desirable to improve the antigenicity of such peptides. In order to use these peptides as pharmaceuticals, it is necessary to have both improved antigenicity and durability.

Chemical modification of the peptides with macromolecular compounds such as poly(ethylene glycol) has been shown to be effective to improve the antigenicity and durability of various peptides. Thus, poly(ethylene glycol) and poly(ethylene glycol) derivatives have been widely used as peptide-modifying macromolecular reagents.

In its most common form, poly(ethylene glycol) has the following structure:

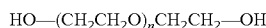

The above polymer, alpha-, omega-dihydroxyl poly(ethylene glycol) can be represented in brief form as HO-PEG-OH where it is understood that the -PEG- symbol represents the following structural unit:

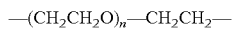

Without being limited to any particular theory or mechanism of action, the long, chain-like PEG molecule or moiety is believed to be heavily hydrated and in rapid motion when in an aqueous medium. This rapid motion is believed to cause the PEG to sweep out a large volume and prevents the approach and interference of other molecules. As a result, when attached to another chemical entity (such as a peptide), PEG polymer chains can protect such chemical entity from an immune response and other clearance mechanisms. As a result, PEGylation leads to improved drug efficacy and safety by optimizing pharmacokinetics, increasing bioavailability, and decreasing immunogenicity and dosing frequency.

For example, some active derivatives of PEG have been attached to peptides, proteins and enzymes with beneficial results. PEG is soluble in organic solvents. PEG attached to enzymes can result in PEG-enzyme conjugates that are soluble and active in organic solvents. Attachment of PEG to protein can reduce the immunogenicity and rate of kidney clearance of the PEG-protein conjugate as compared to the unmodified protein, which may result in dramatically increased blood circulation lifetimes for the conjugate.

For example, covalent attachment of PEG to therapeutic proteins such as interleukins (Knauf, M. J. et al., J. Biol. Chem. 1988, 263, 15,064; Tsutsumi, Y. et al., J. Controlled Release 1995, 33, 447), interferons (Kita, Y. et al., Drug Des. Delivery 1990, 6, 157), catalase (Abuchowski, A. et al., J. Biol. Chem. 1977, 252, 3, 582), superoxide dismutase (Beauchamp, C. O. et al., Anal. Biochem. 1983, 131, 25), and adenosine deaminase (Chen, R. et al., Biochim. Biophy. Acta 1981, 660, 293), has been reported to extend their half life in vivo, and/or reduce their immunogenicity and antigenicity.

In addition, PEG attached to surfaces can reduce protein and cell adsorption to the surface and alter the electrical properties of the surface. Similarly, PEG attached to liposomes can result in a great increase in the blood circulation lifetime of these particles and thereby possibly increase their utility for drug delivery. (J. M. Harris, Ed., "Biomedical and Biotechnical Applications of Polyethylene Glycol Chemistry," Plenum, New York, 1992).

The presence of an amino acid or peptide arm between PEG and the attached macromolecule has demonstrated several advantages due to the variability of properties that may be introduced using a suitable amino acid or peptide. Of these amino acid or peptide arms, Norleucine (Nle) is used for analytical purposes; $^{14}C$ or tritium labeled Gly is used for pharmacokinetic studies; Lys is used for branching; and Met-Nle or Met-βAla is used for PEG removal by BrCN treatment (Veronese, F. M. Biomaterials, 2001, 22, 405).

Another known type of PEG derivative with amino acid arm between PEG and the attached macromolecules is characterized by two linear PEG chains linked together through two functions of a tri-functional linker while the third function is used to bind the protein. Lysine is the tri-functional amino acid linker and the two PEG chains are linked to its alpha and epsilon amino groups while the carboxylic group is activated as hydroxysuccinimidyl esters for protein binding. This PEG derivative has the advantage of a lower inactivation of the enzymes during conjugation and its "umbrella-like" structure is effective in protecting proteins from proteolysis, in the approach of antibodies and in reducing immunogenicity (Veronese, F. M. Biomaterials, 2001, 22, 405).

PEG-linker-peptide or PEG-linker-liposome are sometimes formed as undesirable by-products when part of the activating group was incorporated into the final PEG-peptide or PEG-liposome adduct. Frances et al. (Int. J. Hematol. 1998, 68, 1) disclose that such linkers can have several types of adverse effects: (1) these linkers are not necessarily immunologically inert and there is experimental evidence that such groups are responsible for immunogenicity/antigenicity of PEG proteins; (2) some linkers moieties contain labile bonds that can be cleaved enzymatically or chemically; (3) linker moieties derived from often relatively toxic activated PEGs could lead to regulatory problems; (4) certain linker group such as triazine ring could cause crosslinking.

Chemical modification of the peptides with other compounds besides PEG has been shown to be effective to improve the activity and durability of various peptides. Examples include attachment of fatty acids (Wang et al., J. Med. Chem. 2005, 48, 3328), active transport agents (e.g., cholic acid), tight junction modulators (Johnson and Quay, Expert Opin. Drug Deliv. 2005, 2, 281), peptides (e.g., polyarginine), cytotoxic agents (e.g., doxorubicin), other polymers such as hyaluronic acid or carbohydrates, and the like.

Attachment of PEG or another chemical group to, for example, peptides may be achieved through the use of linker molecules. These linker molecules may provide multiple functional ends, allowing the attachment of several molecules through the use of a single linker. However, despite the advances made in the area of, for example, PEG or other modifier peptide-based conjugates, there remains a need for novel linker molecules to provide additional methods of molecular conjugation.

The citation and/or discussion of a reference in this section, and throughout this specification, shall not be construed as an admission that such reference is prior art to the present invention.

SUMMARY OF THE INVENTION

The linkers of the present invention are capable of attaching at least one molecular moiety to another molecular moiety.

One embodiment is a linker moiety compound, wherein the linker moiety compound has the structure:

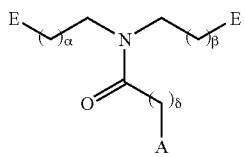

wherein
  $\alpha$ is an integer, $1 \leq \alpha \leq 7$;
  $\beta$ is an integer, $1 \leq \beta \leq 7$;
  $\delta$ is an integer, $2 \leq \delta \leq 5$;
  A is either $CO_2H$, activated $CO_2H$, $NH_2$, NCO, CHO, maleimide, or vinyl sulfone; and
  E is either $NH_2$, $CO_2H$, CHO, maleimide, or NHBoc.

A further embodiment is where
  $\alpha = \beta = 1$ or 2;
  $\delta = 3$;
  A is either $CO_2H$ or activated $CO_2H$; and
  E is $NH_2$ or NHBoc.

Another linker moiety compound embodiment is a linker moiety compound wherein the linker moiety compound has the structure:

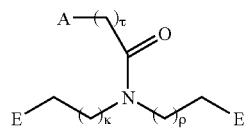

wherein
  $\kappa$ is an integer, $0 \leq \kappa \leq 8$;
  $\rho$ is an integer, $0 \leq \rho \leq 8$;
  $\tau$ is an integer, $2 \leq \tau \leq 5$;
  A is either NHR, or NRBoc;
  R is alkyl; and
  E is either $NH_2$, $CO_2H$, activated $CO_2H$, CHO, maleimide, or NRBoc, wherein R is H, or alkyl A further embodiment is where
  $\kappa = \rho = 0$;
  $\tau = 3$;
  A is NHBoc;
  R is $CH_3$; and
  E is $CO_2H$ or CONHS.

Another linker moiety compound embodiment is wherein the linker moiety compound links three or more molecules and wherein the linker moiety compound has the structure:

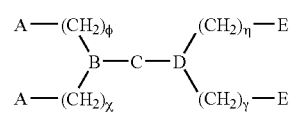

wherein
  $\chi$ is an integer, $1 \leq \chi \leq 4$
  $\phi$ is an integer, $1 \leq \phi \leq 4$;
  $\gamma$ is an integer, $2 \leq \gamma \leq 8$;
  $\eta$ is an integer $2 \leq \eta \leq 8$;
  A is either $CO_2H$, activated $CO_2H$, $NH_2$, NCO, CHO, maleimide, or vinyl sulfone;
  B is either CH or N;
  C is either $CO(CH_2)_\sigma CO$ or $(CH_2)_\sigma$;
  D is either CH or N;
  E is either $NH_2$, NHBoc, $CO_2H$, CHO, or maleimide; and
  $\sigma$ is an integer, $2 \leq \sigma \leq 5$.

A further embodiment is where
  $\chi = 1$;
  $\phi = 1$;
  $\gamma$ is an integer $2 \leq \gamma \leq 3$;
  $\eta$ is an integer $2 \leq \eta \leq 3$;
  A is either $CO_2H$ or activated $CO_2H$;
  B is N;
  C is $CO(CH_2)_v CO$ or $(CH_2)_v$;
  D is N;
  E is NHBoc; and
  $\sigma$ is an integer, $2 \leq \sigma \leq 3$.

Another embodiment is where the linker moiety compound links three or more molecules and wherein the linker moiety compound has the structure:

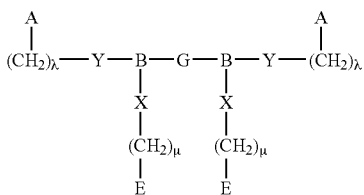

wherein
λ is an integer, 1≦λ≦4;
μ is an integer, 1≦μ≦4;
A is either CO₂H, activated CO₂H (activated CO₂H), NH₂, NCO, CHO, maleimide, or vinyl sulfone;
B is either CH or N;
G is either $(CH_2)_v$, CO or $COCH_2OCH_2CO$;
E is either NH₂, NHBoc, CO₂H, CHO, or maleimide;
X is either CO, bond, or CONH;
Y is either CO, bond, or NHCO; and
v is an integer, 2≦v≦4.
A further embodiment is where
λ is an integer, 1≦λ≦3;
μ=2;
A is either CO₂H or activated CO₂H;
B is N;
G is either $(CH_2)_v$, CO or $COCH_2OCH_2CO$;
E is NH₂ or NHBoc;
X is CO or bond;
Y is CO or bond; and
v=2.

Further embodiments of the above linker moieties include compounds comprising a peptide moiety, an above linker moiety, and a water-soluble polymer moiety. In certain embodiments, A is either CO, NH, NCO, or SO₂CH₂CH₂ and E is either NH or CO such that the linker moieties are covalently attached to the peptide or water-soluble polymer moiety.

Preferably, the water-soluble polymer moiety is a poly (ethylene glycol) moiety. More preferably the poly(ethylene glycol) moiety is linear and has a molecular weight of from about 2 kDaltons to 60 kDaltons. Even more preferably the poly(ethylene glycol) moiety has a molecular weight of about 20 to 40 kDaltons. Most preferably the poly(ethylene glycol) moiety has a molecular weight of 20 kDaltons. Preferably, the poly(ethylene glycol) moiety has a polydispersity value ($M_w/M_n$) of less than 1.20, more preferably less than 1.1, and most preferably less than 1.05. In certain embodiments, two water-soluble moieties are attached to a peptide moiety via a linker moiety.

In one embodiment on the invention, the peptide moiety is dimeric and comprises two monomeric peptides linked by a linker moiety.

In one embodiment, the peptide moiety is selected from peptides which bind to erythropoietin-receptors. Non-limiting examples of such EPO-R binding peptides include those disclosed in published international applications PCT/US00/32224 (publication no. WO 01/38342 A2, U.S. designated), PCT/US96/09810 (publication no. WO 96/40749, U.S. designated) and PCT/US01/16654 (publication no. WO 01/91780 A1); and U.S. Pat. Nos. 5,767,078, 5,773,569, 5,830,851, 5,986,047 and 6,221,608. Additional non-limiting examples of such EPO-R binding peptides disclosed in PCT/US2004/014886 (publication no. WO 2004/101611), and PCT/US2004/014889 (publication no. WO 2004/101606).

The present invention also relates to pharmaceutical compositions comprising the compound(s) described above.

DETAILED DESCRIPTION

Definitions

Figure 1:
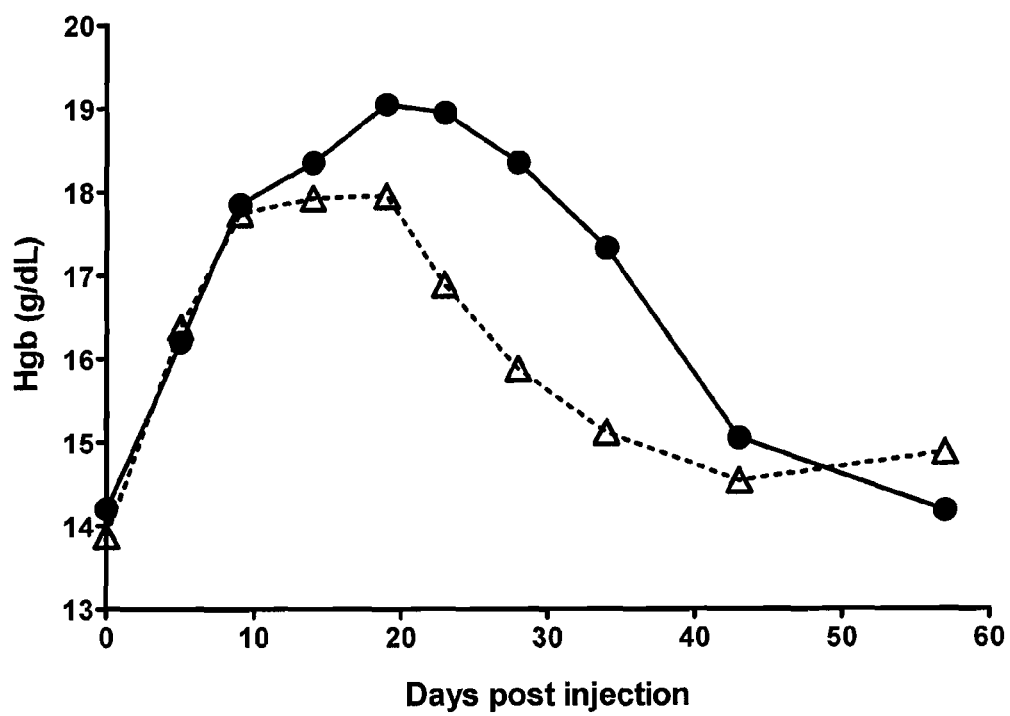
FIG. 1. Change in hemoglobin (Hgb) in male Sprague-Dawley rats after single bolus IV injection of PEGylated peptides at 10 mg/kg. Dashed line (Δ): Compound I, solid line (●): Compound XIII.
Figure 2:
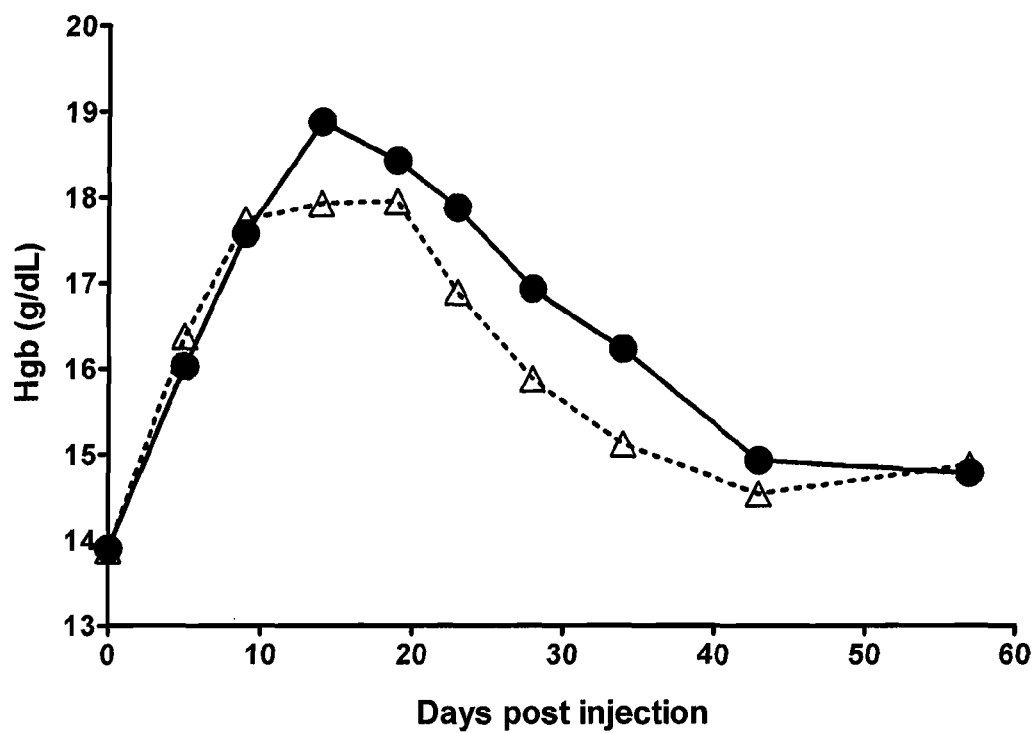
FIG. 2. Change in hemoglobin (Hgb) in male Sprague-Dawley rats after single bolus IV injection of PEGylated peptides at 10 mg/kg. Dashed line (Δ): Compound I, solid line (●): Compound V.
Figure 3:
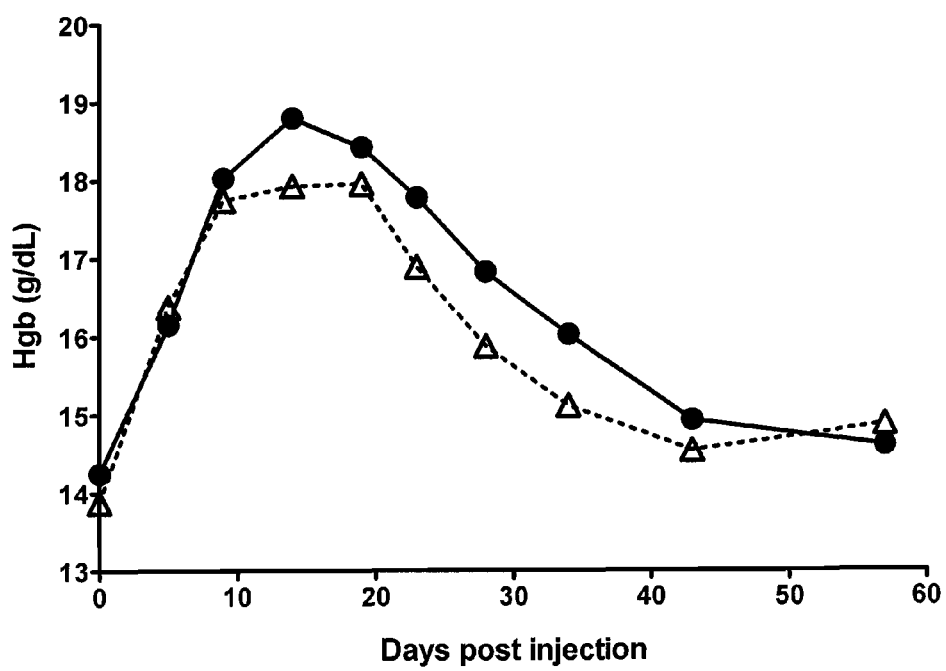
FIG. 3. Change in hemoglobin (Hgb) in male Sprague-Dawley rats after single bolus IV injection of PEGylated peptides at 10 mg/kg. Dashed line (Δ): Compound I, solid line (●): Compound IV.
Figure 4:
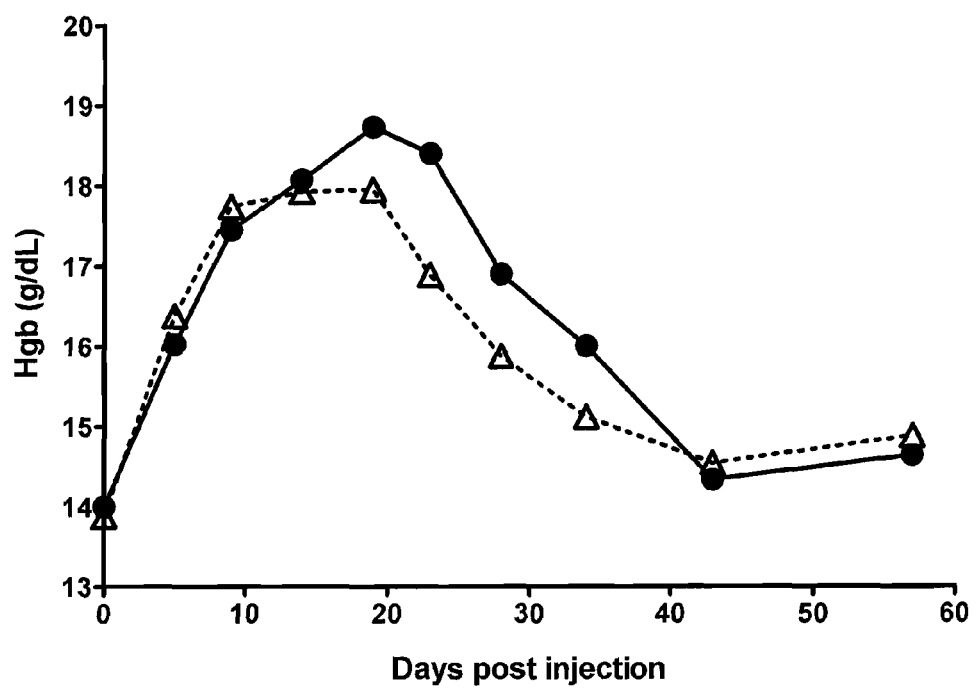
FIG. 4. Change in hemoglobin (Hgb) in male Sprague-Dawley rats after single bolus IV injection of PEGylated peptides at 10 mg/kg. Dashed line (Δ): Compound I, solid line (●): Compound III.
Figure 5:
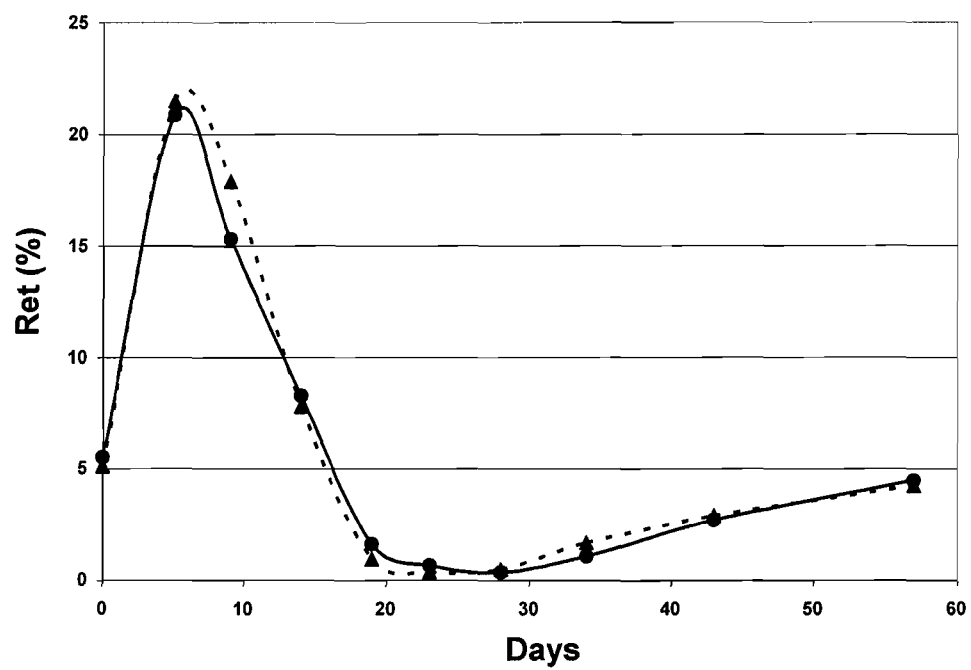
FIG. 5. Change in observed reticulocyte percent (Ret %) in male Sprague-Dawley rats according to the methods of Example 25. Dashed line (Δ): Compound I, solid line (●): Compound III.
Figure 6:
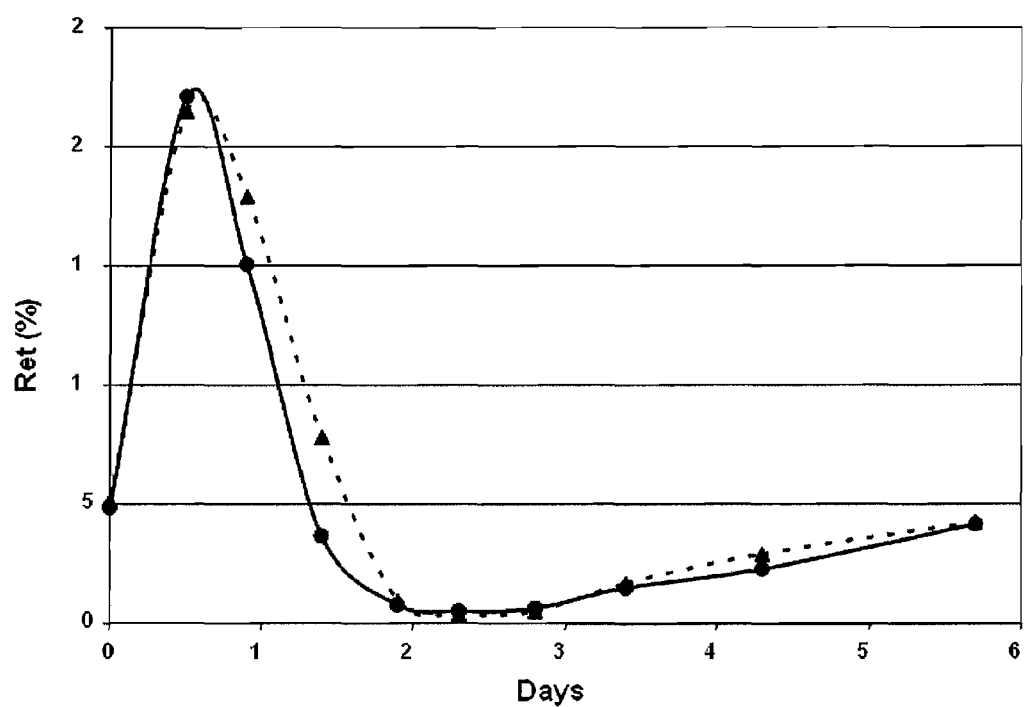
FIG. 6. Change in observed reticulocyte percent (Ret %) in male Sprague-Dawley rats according to the methods of Example 25. Dashed line (Δ): Compound I, solid line (●): Compound V.
Figure 7:
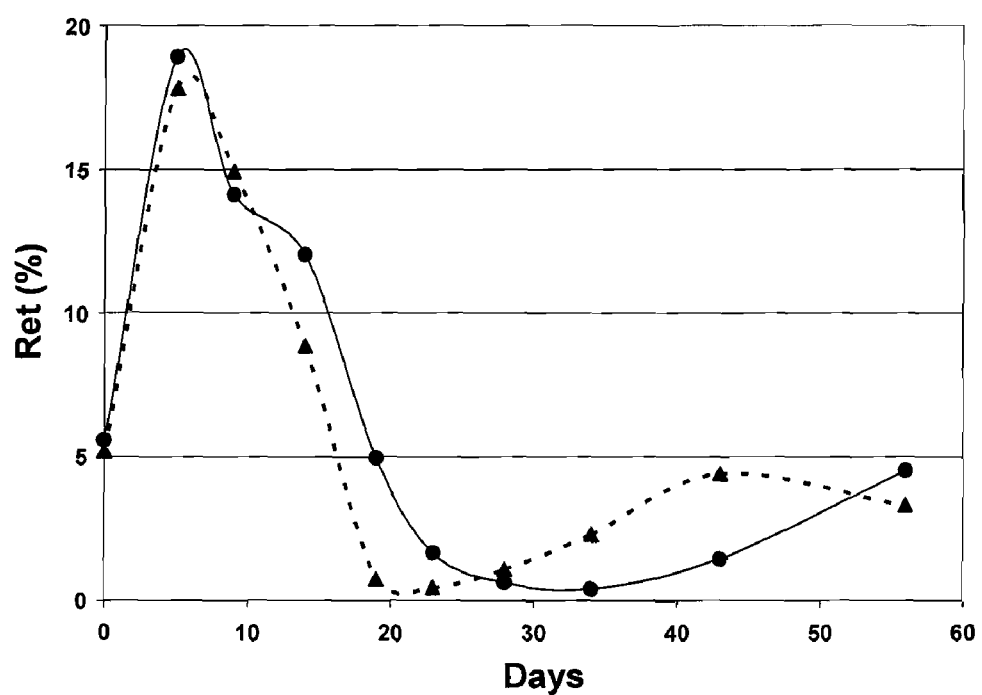
FIG. 7. Change in observed reticulocyte percent (Ret %) in male Sprague-Dawley rats according to the methods of Example 25. Dashed line (Δ): Compound I, solid line (●): Compound XIII.
Figure 8:
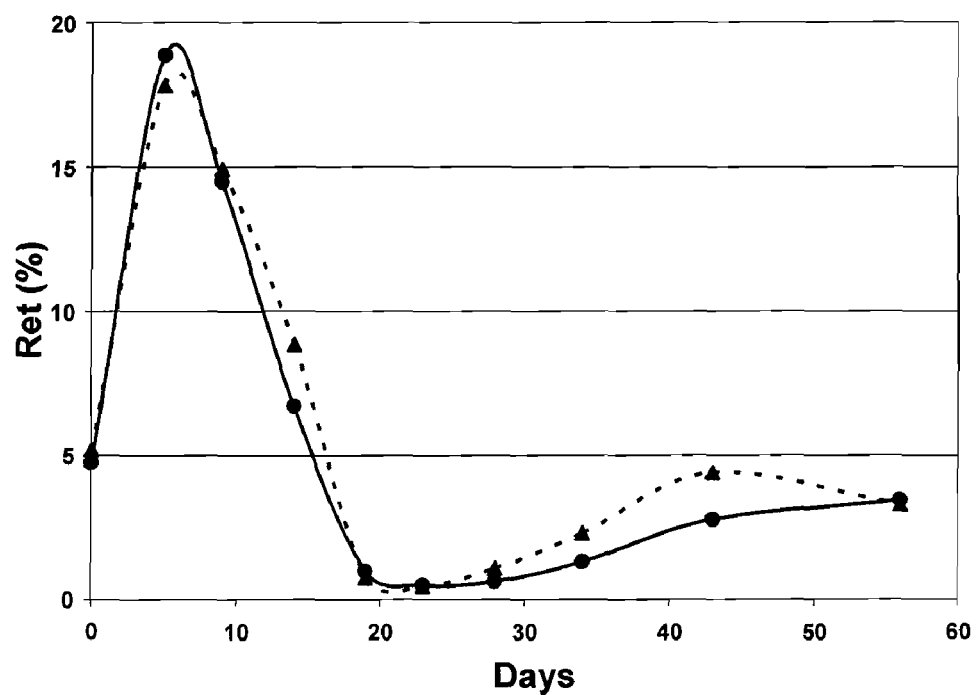
FIG. 8. Change in observed reticulocyte percent (Ret %) in male Sprague-Dawley rats according to the methods of Example 25. Dashed line (Δ): Compound I, solid line (●): Compound IV.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E;

Cysteine is Cys or C; Tryptophan is Trp or W; Arginine is Arg or R; and Glycine is Gly or G. The unconventional amino acids in peptides are abbreviated as follows: 1-naphthylalanine is 1-Nal or $N_p$; 2-naphthylalanine is 2-Nal; N-methylglycine (also known as sarcosine) is MeG or $S_c$ or Sar; and acetylated glycine (N-acetylglycine) is AcG.

"Peptide" or "polypeptide" refers to a polymer in which the monomers are alpha amino acids joined together through amide bonds. Peptides are two or often more amino acid monomers long. Preferably, peptides of the present invention contain less than about fifty amino acid monomers in length.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

As used herein the term "agonist" refers to a biologically active ligand which binds to its complementary biologically active receptor and activates the latter either to cause a biological response in the receptor, or to enhance preexisting biological activity of the receptor.

As used herein the terms "activated $CO_2H$" or "COX" refer to active esters of carboxylic acids that can participate in coupling reactions, typically to form amide or ester bonds upon treatment with an amine or hydroxy group. A preferred embodiment is an N-hydroxysuccinimide activated carboxyl group. Another preferred embodiment of this invention relies on in situ activation, in which a carboxylic acid and amine are allowed to react in the presence of a coupling agent such as diisopropylcarbodiimide, dicyclohexylcarbodiimide, 1-(3-dimethylaminopropyl)-3-ethylcarbodiimide (EDC), or the like.

Linker Moiety

The linkers of the present invention are capable of attaching at least two moieties, which may be water-soluble polymer moieties, to a third moiety, which may be a peptide.

In one embodiment of the present invention is presented a linker moiety compound wherein the linker moiety compound has the structure:

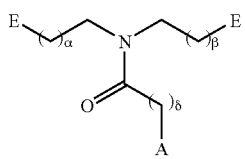

wherein $\alpha$, $\beta$, and $\delta$ are each integers whose values are independently selected.

In preferred embodiments,
$\alpha$ is an integer, $1 \leq \alpha \leq 7$;
$\beta$ is an integer, $1 \leq \beta \leq 7$;
$\delta$ is an integer, $2 \leq \delta \leq 5$;
A is either $CO_2H$, COX (activated $CO_2H$, including through N-hydroxysuccinimide), $NH_2$, NCO, CHO, maleimide, or vinyl sulfone; and
E is either $NH_2$, NHBoc, $CO_2H$, CHO, or maleimide.

In one particularly preferred embodiment,
$\alpha=\beta 1$ or 2;
$\delta=3$;
A is either $CO_2H$ or COX (activated $CO_2H$); and
E is NHBoc.

In another particularly preferred embodiment,
$\alpha=\beta 2$;
$\delta=3$;
A is either $CO_2H$ or COX (activated $CO_2H$); and
E is NHBoc.

Another linker moiety compound embodiment is a linker moiety compound wherein the linker moiety compound has the structure:

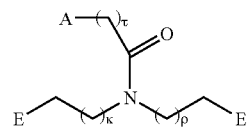

wherein
$\kappa$ is an integer, $0 \leq \kappa \leq 8$;
$\rho$ is an integer, $0 \leq \rho \leq 8$;
$\tau$ is an integer, $2 \leq \tau \leq 5$;
A is either NHR or NRBoc;
R is alkyl; and
E is either $NH_2$, $CO_2H$, activated $CO_2H$, CHO, maleimide, or NRBoc, wherein R is H, or alkyl.

A further embodiment is where
$\kappa=\rho=0$;
$\tau=3$;
A is NRBoc;
R is $CH_3$; and
E is $CO_2H$ or CONHS.

In another embodiment of the present invention, the linker moiety is a tetrafunctional linker having the following structure:

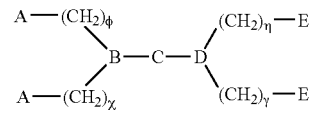

wherein $\chi$, $\phi$, $\gamma$, and $\eta$ are each integers whose values are independently selected.

In preferred embodiments,
$\chi$ is an integer, $1 \leq \chi \leq 4$;
$\phi$ is an integer, $1 \leq \phi \leq 4$;
$\gamma$ is an integer, $2 \leq \gamma \leq 8$;
$\eta$ is an integer $2 \leq \eta \leq 8$;
A is either $CO_2H$, COX (activated $CO_2H$, including through N-hydroxysuccinimide), $NH_2$, NCO, CHO, maleimide, or vinyl sulfone;
B is either CH or N;
C is either $CO(CH_2)_\sigma CO$ or $(CH_2)_\sigma$;
D is either CH or N;
E is either $NH_2$, NHBoc, $CO_2H$, CHO, or maleimide; and
$\sigma$ is an integer, $2 \leq \sigma \leq 5$.

In particularly preferred embodiments,
χ=1;
φ=1;
γ is an integer 2≦γ≦3;
η is an integer 2≦η≦3;
A is either $CO_2H$ or COX (activated $CO_2H$);
B is N;
C is $CO(CH_2)_\sigma CO$ or $(CH_2)_\sigma$;
D is N;
E is NHBoc; and
σ is an integer, 2≦σ≦3.
In one certain embodiment,
χ=1;
φ=1;
γ is an integer 2≦γ≦3;
η is an integer 2≦η≦3;
A is either $CO_2H$ or COX (activated $CO_2H$);
B is N;
C is $CO(CH_2)_\sigma CO$;
D is N;
E is NHBoc; and
σ is an integer, 2≦σ≦3.

In an another embodiment of the present invention, the linker moiety is a tetrafunctional linker having the following structure:

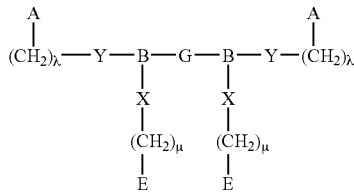

wherein λ and μ are each integers whose values are independently selected.

In preferred embodiments,
λ is an integer, 1≦λ≦4
μ is an integer, 1≦μ≦4;
A is either $CO_2H$, COX (activated $CO_2H$, including through N-hydroxysuccinimide), $NH_2$, NCO, CHO, maleimide, or vinyl sulfone;
B is either CH or N;
G is either $(CH_2)_\nu$, CO or $COCH_2OCH_2CO$;
E is either $NH_2$, NHBoc, $CO_2H$, CHO, or maleimide;
X is either CO, bond, or CONH;
Y is either CO, bond, or NHCO; and
ν is an integer, 2≦ν≦4.
In particularly preferred embodiments,
λ is an integer, 1≦λ≦3;
μ=2;
A is either $CO_2H$ or COX (activated $CO_2H$);
B is N;
G is either $(CH_2)_\nu$, CO or $COCH_2OCH_2CO$;
E is NH or NHBoc;
X is CO or bond;
Y is CO or bond; and
ν=2.

According to the invention, the E terminus of the linker may comprise a protecting group that must be removed to liberate a reactive functional group before a water-soluble polymer moiety (preferably PEG) is attached. The protecting group of the E terminus of the linker may include, but is not limited to Boc and Alloc. The water-soluble moiety may be attached directly to the E-terminus of the linker or it may be attached indirectly, for example with an amide or carbamate linkage. The linkers of the present invention allow for the attachment of one or more water-soluble polymer moieties.

According to the invention a peptide moiety may be attached to the A terminus of the linker. The linker may be attached to either the C-terminus or the N-terminus of the peptide. Hence, in embodiments where the linker is attached to the C-terminus of the peptide, A is $NH_2$. In embodiments where the linker is attached to the N-terminus of the peptide, A is $CO_2H$, COX (activated $CO_2H$), or NCO. In alternative embodiments, the peptide contains a thiol side chain such as that found in cysteine and A is maleimide. In other embodiments, the peptide contains a free amine which is attached to a linker where A is CHO by a reductive amination reaction. In alternative preferred embodiments, a linker of the invention, wherein A is $CO_2H$ or COX (activated $CO_2H$), is attached by an amide bond to the ε-amino group of a lysine residue of the peptide monomer. Said lysine residue may be in any position in the peptide monomer. In a preferred embodiment, the lysine is located at the C-terminus of the peptide.

The linker moiety may be incorporated into the peptide during peptide synthesis. For example, where a linker contains two free functional groups (e.g., a carboxyl group or an amino group) that enables binding to another molecular moiety, the linker may be conjugated to the solid support. Thereafter, the peptide may be synthesized directly onto the linker's free functional group by standard solid phase techniques.

In another embodiment, the linker moiety may be conjugated to the peptide after peptide synthesis. Such conjugation may be achieved by methods well established in the art. In one embodiment, the linker contains at least one functional group suitable for attachment to the target functional group of the synthesized peptide. For example, a linker with a free amine group may be reacted with a peptide's C-terminal carboxyl group.

In one embodiment, the linker moiety is first attached to one or two peptides, in the latter case forming a peptide dimer. Thereafter, the protecting groups of the linker are removed to liberate two reactive groups. After that, the two reactive groups are attached to two water-soluble polymer moieties (preferably PEG moieties).

Alternatively, the water-soluble moieties (preferably PEG moieties) may be conjugated to the linker first, followed by liberating reactive functional groups of the linker that can react with one or two peptides, in the latter case forming a peptide dimer.

In certain embodiments, the linker is trifunctional and the A terminus is attached to a second linker. The second linker may be attached to one or two peptides, in the latter case forming a peptide dimer.

Water-Soluble Polymer/PEG Moiety

Water-soluble polymer moieties of the present invention include, but are not limited to, (a) polyalkylene glycol and derivatives thereof, including PEG, mPEG, PEG homopolymers, polypropylene glycol homopolymers, copolymers of ethylene glycol with propylene glycol, wherein said homopolymers and copolymers are unsubstituted or substituted at one end with an alkyl group; (b) cellulose and cellulose derivatives, including methylcellulose and carboxymethyl cellulose; (c) starch and dextrines, and derivatives thereof, (d) dextran and dextran derivatives, including dextran sulfate, cross linked dextrin, and carboxymethyl dextrin; (e) heparin and fragments of heparin; (f) polyvinyl alcohol and polyvinyl ethyl ethers; (g) polyvinylpyrrolidone; (h) a,b-poly[(2-hydroxyethyl)-DL-aspartamide; and (i) polyoxyethylated polyols.

These polymers can be linear, branched, or star-shaped with a wide range of molecular weight.

The water-soluble polymer moiety preferably is PEG. The preferred PEG for use in the present invention is linear PEG having a molecular weight of more than about 2 kDaltons (kDa). Preferably the PEG has a molecular weight of about 10 kDa to about 60 kDa. Preferably the PEG has a molecular weight of from about 20 kDa to about 40 kDa. Preferably, the PEG has a molecular weight of about 40 kDa. Preferably, each PEG moiety is 10 to 30 kDaltons for a total of 20 to 60 kDaltons for two PEG moieties.

The water-soluble polymer moiety is covalently attached to the spacer or linker moiety. In one embodiment, a PEG moiety is attached to the N-terminus of the spacer or linker.

The compounds of the present invention may comprise multiple water-soluble polymer moieties (preferably PEG moieties) (e.g., 2, 3, 4, or more), at least one of such multiple water-soluble polymer moieties is linked through a linker moiety. Where the compound comprises more than one water-soluble polymer moiety, the multiple water-soluble polymer moieties may be the same or different chemical moieties (e.g., PEGs of different molecular weight). In one embodiment of the invention, the water-soluble polymer moiety is dimeric and comprises two monomeric PEGs linked by a linker moiety. In some cases, the degree of PEGylation (the number of PEG moieties attached to a peptide and/or the total number of peptides to which a PEG is attached) may be influenced by the proportion of PEG molecules versus peptide molecules in a PEGylation reaction, as well as by the total concentration if each in the reaction mixture. In general, the optimum PEG versus peptide ratio (in terms of reaction efficiency to provide for no excess unreacted peptides and/or PEG) will be determined by factors such as the desired degree of PEGylation (e.g., mono, di-, tri-, etc.), the molecular weight of the polymer selected, whether the polymer is branched or unbranched, and the reaction conditions for a particular attachment method.

There are a number of PEG attachment methods available to those skilled in the art [see, e.g., Goodson, et al. (1990) Bio/Technology 8:343 (PEGylation of interleukin-2 at its glycosylation site after site-directed mutagenesis); EP 0 401 384 (coupling PEG to G-CSF); Malik, et al., (1992) Exp. Hematol. 20:1028-1035 (PEGylation of GM-CSF using tresyl chloride); PCT Pub. No. WO 90/12874 (PEGylation of erythropoietin containing a recombinantly introduced cysteine residue using a cysteine-specific mPEG derivative); U.S. Pat. No. 5,767,078 (PEGylation of EPO peptides); U.S. Pat. No. 5,672,662 (Poly(ethylene glycol) and related polymers monosubstituted with propionic or butanoic acids and functional derivatives thereof for biotechnical applications); U.S. Pat. No. 6,077,939 (PEGylation of an N-terminal α-carbon of a peptide); Veronese et al., (1985) Appl. Biochem. Bioechnol 11:141-142 (PEGylation of an N-terminal α-carbon of a peptide with PEG-nitrophenylcarbonate ("PEG-NPC") or PEG-trichlorophenylcarbonate); and Veronese (2001) Biomaterials 22:405-417 (Review article on peptide and protein PEGylation)].

For example, PEG may be covalently bound to amino acid residues via a reactive group. Reactive groups are those to which an activated PEG molecule may be bound (e.g., a free amino or carboxyl group). For example, N-terminal amino acid residues and lysine (K) residues have a free amino group; and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide have been described [Schwarz, et al. (1990) Methods Enzymol. 184:160; Rose, et al. (1991) Bioconjugate Chem. 2:154; Gaertner, et al. (1994) J. Biol. Chem. 269:7224].

For example, PEG molecules may be attached to amino groups using methoxylated PEG ("mPEG") having different reactive moieties. Non-limiting examples of such reactive moieties include succinimidyl succinate (SS), succinimidyl carbonate (SC), mPEG-imidate, para-nitrophenylcarbonate (NPC), succinimidyl propionate (SPA), and cyanuric chloride. Non-limiting examples of such mPEGs include mPEG-succinimidyl succinate (mPEG-SS), mPEG$_2$-succinimidyl succinate (mPEG$_2$-SS); mPEG-succinimidyl carbonate (mPEG-SC), mPEG$_2$-succinimidyl carbonate (mPEG$_2$-SC); mPEG-imidate, mPEG-para-nitrophenylcarbonate (mPEG-NPC), mPEG-imidate; mPEG$_2$-para-nitrophenylcarbonate (mPEG$_2$-NPC); mPEG-succinimidyl propionate (mPEG-SPA); mPEG$_2$-succinimidyl propionate (mPEG$_2$-SPA); mPEG-N-hydroxy-succinimide (mPEG-NHS); mPEG$_2$-N-hydroxy-succinimide (mPEG$_2$-NHS); mPEG-cyanuric chloride; and mPEG$_2$-cyanuric chloride.

Where attachment of the PEG is non-specific and a peptide containing a specific PEG attachment is desired, the desired PEGylated compound may be purified from the mixture of PEGylated compounds. For example, if an N-terminally PEGylated peptide is desired, the N-terminally PEGylated form may be purified from a population of randomly PEGylated peptides (i.e., separating this moiety from other monoPEGylated moieties).

In some embodiments, PEG is attached site-specifically to a peptide or a spacer. Site-specific PEGylation at the N-terminus, side chain, and C-terminus of a potent analog of growth hormone-releasing factor has been performed through solid-phase synthesis [Felix, et al. (1995) Int. J. Peptide Protein Res. 46:253]. Another site-specific method involves attaching a peptide to extremities of liposomal surface-grafted PEG chains in a site-specific manner through a reactive aldehyde group at the N-terminus generated by sodium periodate oxidation of N-terminal threonine [Zalipsky, et al. (1995) Bioconj. Chem. 6:705]. However, this method is limited to polypeptides with N-terminal serine or threonine residues.

In one method, selective N-terminal PEGylation may be accomplished by reductive alkylation which exploits differential reactivity of different types of primary amino groups (lysine versus the N-terminal) available for derivatization in a particular peptide or linker moiety. Under the appropriate reaction conditions, a PEG containing a carbonyl group is selectively attached to the N-terminus of a peptide or linker. For example, one may selectively N-terminally PEGylate the protein by performing the reaction at a pH which exploits the $pK_a$ differences between the ε-amino groups of a lysine residue and the α-amino group of the N-terminal residue of the peptide or linker. By such selective attachment, PEGylation takes place predominantly at the N-terminus of the protein, with no significant modification of other reactive groups (e.g., lysine side chain amino groups). Using reductive alkylation, the PEG should have a single reactive aldehyde for coupling to the protein (e.g., PEG propionaldehyde may be used).

Site-specific mutagenesis is a further approach which may be used to prepare peptides for site-specific polymer attachment. By this method, the amino acid sequence of a peptide is designed to incorporate an appropriate reactive group at the desired position within the peptide. For example, WO 90/12874 describes the site-directed PEGylation of proteins modified by the insertion of cysteine residues or the substitution of other residues for cysteine residues. This publication also describes the preparation of mPEG-erythropoietin ("mPEG-EPO") by reacting a cysteine-specific mPEG derivative with a recombinantly introduced cysteine residue on EPO.

Where the PEG moiety is attached to a spacer moiety or a linker moiety, similar attachment methods may be used. In this case, the linker or spacer contains a reactive group and an activated PEG molecule containing the appropriate complementary reactive group is used to effect covalent attachment. In preferred embodiments the linker or spacer reactive group is a terminal reactive group (i.e., positioned at the terminus of the linker or spacer).

Peptides, peptide dimers and other peptide-based molecules of the invention can be attached to water-soluble polymers (e.g., PEG) using any of a variety of chemistries to link the water-soluble polymer(s) to the receptor-binding portion of the molecule (e.g., peptide+linker/spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the linker and/or to one or both peptide chains. In some embodiments, the dimer or higher order multimer will comprise distinct species of peptide chain (i.e., a heterodimer or other heteromultimer). By way of example and not limitation, a dimer may comprise a first peptide chain having a PEG attachment junction and the second peptide chain may either lack a PEG attachment junction or utilize a different linkage chemistry than the first peptide chain and in some variations the linker may contain or lack a PEG attachment junction and said linker, if PEGylated, may utilize a linkage chemistry different than that of the first and/or second peptide chains. An alternative embodiment employs a PEG attached to the linker portion of the receptor-binding portion and a different water-soluble polymer (e.g., a carbohydrate) conjugated to a side chain of one of the amino acids of the peptide portion of the molecule.

A wide variety of polyethylene glycol (PEG) species may be used for PEGylation of the receptor-binding portion (peptides+linker/spacer). Substantially any suitable reactive PEG reagent can be used. In preferred embodiments, the reactive PEG reagent will result in formation of a carbamate or amide bond upon conjugation to the receptor-binding portion. Suitable reactive PEG species include, but are not limited to, those which are available for sale in the Drug Delivery Systems catalog (2003) of NOF Corporation (Yebisu Garden Place Tower, 20-3 Ebisu 4-chome, Shibuya-ku, Tokyo 150-6019) and the Molecular Engineering catalog (2003) of Nektar Therapeutics (490 Discovery Drive, Huntsville, Ala. 35806). For example and not limitation, the following PEG reagents are often preferred in various embodiments: mPEG2-NHS, mPEG2-ALD, multi-Arm PEG, mPEG(MAL)2, mPEG2 (MAL), mPEG-NH2, mPEG-SPA, mPEG-SBA, mPEG-NPC, mPEG-thioesters, mPEG-Double Esters, mPEG-BTC, mPEG-ButyrALD, mPEG-ACET, heterofunctional PEGs (NH2-PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multi-armed PEGs of the SUNBRITE series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOH, hydroxyl-PEG-aldehyde, carboxylic anhydride type-PEG, functionalized PEG-phospholipid, and other similar and/or suitable reactive PEGs as selected by those skilled in the art for their particular application and usage.

Peptide Moiety

Any peptides derived from various animals including humans, microorganisms or plants and those produced by genetic engineering and by synthesis may be employed as the peptide moiety. Examples include peptides that bind to EPO-R; peptides that bind to TPO-R, cytokines such as various interferons (e.g. interferon-α, interferon-β, interferon-γ), interleukin-2 and interleukin-3, hormones such as insulin, growth hormone-releasing factor (GRF), calcitonin, calcitonin gene related peptide (CGRP), atrial natriuretic peptide (ANP), vasopressin, corticotropin-releasing factor (CRF), vasoactive intestinal peptide (VIP), secretin, α-melanocyte-stimulating hormone (α-MSH), adrenocorticotropic hormone (ACTH), cholecystokinin (CCK), glucagon, parathyroid hormone (PTH), somatostatin, endothelin, substance P, dynorphin, oxytocin and growth hormone-releasing peptide [GHRP, e.g. Endocrinology, 114, 1537 (1984)], growth factors such as growth hormone (GH), insulin-like growth factor (IGF-I, IGF-II), -nerve growth factor (β-NGF), basic fibroblast growth factor (bFGF), transforming growth factor, erythropoietin, granulocyte colony-stimulating factor (G-CSF), granulocyte macrophage colony-stimulating factor (GM-CSF), platelet-derived growth factor (PDGF) and epidermal growth factor (EGF), enzymes such as tissue plasminogen activator (t-PA), elastase, superoxide dismutase (SOD) bilirubin oxydase, catalase, uricase and asparaginase, other proteins such as ubiquitin, islet activating protein (IAP), serum thymic factor (STF), peptide-T and trypsin inhibitor, and derivatives thereof.

Preferably, the peptide moiety comprises one or more peptides, the length of each peptide is less than 50 amino acids, more preferably between about 10 and 25 amino acids, and most preferably between about 12-18 amino acids.

In one preferred embodiment, the peptide moiety is selected from peptides that bind to EPO-R such as those disclosed in (e.g. those disclosed in U.S. Pat. Nos. 5,773,569; 5,830,851; and 5,986,047 to Wrighton, et al.; PCT Pub. No. WO 96/40749 to Wrighton, et al.; U.S. Pat. No. 5,767,078 and PCT Pub. No. 96/40772 to Johnson and Zivin; PCT Pub. No. WO 01/38342 to Balu; and WO 01/91780 to Smith-Swintosky, et al. Still other exemplary EPO-R binding peptides which may be used as the peptide moiety in the present invention are described in PCT/US2004/014886 (publication no. WO 2004/101611), and PCT/US2004/014889 (publication no. WO 2004/101606), all of which are incorporated by reference in their entireties.

In another preferred embodiment, the peptide moiety is selected from peptides which bind to thrombopoietin-receptors ("TPO-R"). Non-limiting examples of such TPO-R binding peptides include those disclosed in U.S. Pat. Nos. 6,858,630, 6,552,008, 6,506,362, 6,498,155, 6,465,430, 6,333,031, 6,251,864, 6,121,238, 6,083,913, 5,932,546, 5,869,451, 5,683,983, 5,677,280, 5,668,110 and 5,654,276; and published U.S. Patent Applications 2003/0009018, 2002/0177166 and 2002/0160013.

In one embodiment, the peptide moiety is a monomeric peptide of 10 to 40 or more amino acid residues in length and having the sequence $X_3X_4X_5GPX_6TWX_7X_8$ (SEQ ID NO:1) where each amino acid is indicated by standard one letter abbreviation; $X_3$ is C; $X_4$ is R, H, L, or W; $X_5$ is M, F, Y, or I; $X_6$ is independently selected from any one of the 20 genetically coded L-amino acids; $X_7$ is D, E, I, L, or V; and $X_8$ is C, which bind and activate the erythropoietin receptor (EPO-R) or otherwise act as an EPO agonist.

In another embodiment, the peptide moiety is a monomeric peptide of 17 to about 40 amino acids in length that comprise the core amino acid sequence LYACHMGPITX$_1$VCQPLR (SEQ ID NO: 2), where each amino acid is indicated by standard one letter abbreviation; and X$_1$ is tryptophan (W), 1-naphthylalanine (1-Nal), or 2-naphthylalanine (2-Nal).

In yet another embodiment, the peptide moiety comprises one or more TPO-R binding peptides with sequence such as Ac-Ile-Glu-Gly-Pro-Thr-Leu-Arg-Gln-Nal(1)-Leu-Ala-Ala-Arg-Sar (SEQ ID NO: 3), or Ac-Ile-Glu-Gly-Pro-Thr-Leu-Arg-Gln-Trp-Leu-Ala-Ala-Arg-Sar (SEQ ID NO: 4).

In one preferred embodiment, the peptide is chosen from:

| SEQ ID NO: | Sequence |
|---|---|
| 5 | Ac-GGLYACHMGPIT (Nal) VCQPLR (MeG) K |
| 6 | Ac-GGLYACHMGPIT (Nal) VCQPLRK |
| 7 | Ac-GLYACHMGPIT (Nal) VCQPLR (MeG) K |
| 8 | Ac-LYACHMGPIT (Nal) VCQPLR (MeG) K |
| 9 | Ac-GLYACHMGPIT (Nal) VCQPLRK |
| 10 | Ac-LYACHMGPIT (Nal) VCQPLRK |
| 11 | Ac-GGLYLCRYGPVT (Nal) ECQPRR (MeG) K |
| 12 | Ac-GGLYLCRYGPVT (Nal) ECQPRRK |
| 13 | Ac-GLYLCRYGPVT (Nal) ECQPRR (MeG) K |
| 14 | Ac-LYLCRYGPVT (Nal) ECQPRR (MeG) K |
| 15 | Ac-GLYLCRYGPVT (Nal) ECQPRRK |
| 16 | Ac-LYLCRYGPVT (Nal) ECQPRRK |
| 17 | Ac-GGTYSCHFGPLT (Nal) VCRPQGGK |
| 18 | Ac-GGTYSCHFGPLT (Nal) VCRPQGK |
| 19 | Ac-GGTYSCHFGPLT (Nal) VCRPQK |
| 20 | Ac-GTYSCHFGPLT (Nal) VCRPQGGK |
| 21 | Ac-TYSCHFGPLT (Nal) VCRPQGGK |
| 22 | Ac-GTYSCHFGPLT (Nal) VCRPQGK |

In another embodiment, peptides are covalently attached to the linkers of the present invention wherein the peptide has a lysine at its C-terminus and the amino group of the lysine is covalently attached to the linker through its amino group.

In one embodiment, the PEG moiety is attached directly to the linker moiety.

In another embodiment, the peptide PEG moiety is attached to a spacer moiety via a linker.

According to some embodiments of this invention, two or more, and preferably between two to six amino acid residues, independently selected from any of the 20 genetically coded L-amino acids or the stereoisomeric D-amino acids, will be coupled to either or both ends of the core sequences described above. For example, the sequence GG will often be appended to either or both termini of the core sequences for ease in synthesis of the peptides. The present invention also provides conjugates of these peptides and derivatives and peptidomimetics of the peptides that retain the property of EPO-R binding.

Stereoisomers (e.g., D-amino acids) of the twenty conventional amino acids, unnatural amino acids such as a,a-disubstituted amino acids, N-alkyl amino acids, lactic acid, and other unconventional amino acids may also be suitable components for compounds of the present invention. Examples of unconventional amino acids include, but are not limited to: β-alanine, 3-pyridylalanine, 4-hydroxyproline, O-phosphoserine, N-methylglycine, N-acetylserine, N-formylmethionine, 3-methylhistidine, 5-hydroxylysine, nor-leucine, 1- or 2-naphthylalanine, sarcosine, and other similar amino acids and imino acids.

In preferred embodiments, the peptide moieties of the invention contain an intramolecular disulfide bond between the two cysteine residues of the core sequence. For example:

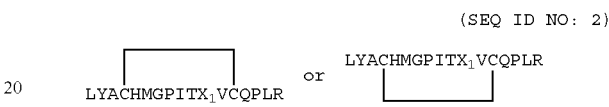

(SEQ ID NO: 2)

Dimeric and Oligomeric Peptides

The preferred embodiment, the monomeric peptide moieties of the present invention are dimerized or oligomerized to form dimers or oligomers. Moreover, such dimers and other multimers may be heterodimers or heteromultimers.

In one embodiment, the peptide monomers of the invention may be oligomerized using the biotin/streptavidin system. Biotinylated analogs of peptide monomers may be synthesized by standard techniques. For example, the peptide monomers may be C-terminally biotinylated. These biotinylated monomers are then oligomerized by incubation with streptavidin [e.g., at a 4:1 molar ratio at room temperature in phosphate buffered saline (PBS) or HEPES-buffered RPMI medium (Invitrogen) for 1 hour]. In a variation of this embodiment, biotinylated peptide monomers may be oligomerized by incubation with any one of a number of commercially available anti-biotin antibodies [e.g., goat anti-biotin IgG from Kirkegaard & Perry Laboratories, Inc. (Washington, D.C.)].

Generally, although not necessarily, peptide dimers dimerized by a technique other than formation of intermolecular disulfide bonds, will also contain one or more disulfide bonds between cysteine residues of the peptide monomers. For example, the two monomers may be cross-linked by one or more intermolecular disulfide bonds. Preferably, the two monomers contain at least one intramolecular disulfide bond. Most preferably, both monomers of a peptide dimer contain an intramolecular disulfide bond, such that each monomer contains a cyclic group.

Peptide Modification

One can also modify the amino and/or carboxy termini of the peptide compounds of the invention to produce other compounds of the invention. Amino terminus modifications include methylation (i.e., —NHCH$_3$ or —N(CH$_3$)$_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated. In most preferred embodiments an N-terminal glycine is acetylated to yield N-acetylglycine (AcG).

Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the 20 genetically encoded amino acids (or the stereoisomeric D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptide moieties by phosphorylation, and other methods [e.g., as described in Hruby, et al. (1990) Biochem J. 268:249-262].

The peptide moieties of the invention may also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis [See, Morgan and Gainor (1989) Ann. Rep. Med. Chem. 24:243-252]. These techniques include replacing the peptide backbone with a backbone composed of phosphonates, amidates, carbamates, sulfonamides, secondary amines, and N-methylamino acids.

Pharmaceutical Compositions

In another aspect of the present invention, pharmaceutical compositions of the above PEG-modified peptide based compounds are provided. Conditions alleviated or modulated by the administration of such compositions include those indicated above. Such pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration. In general, comprehended by the invention are pharmaceutical compositions comprising effective amounts of a therapeutic peptide (e.g., peptides that bind to EPO-R), with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the EPO-R agonist peptides (or chemically modified forms thereof) and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

The peptides may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. As discussed above, PEGylation is a preferred chemical modification for pharmaceutical usage. Other moieties that may be used include: propylene glycol, copolymers of ethylene glycol and propylene glycol, carboxymethyl cellulose, dextran, fatty acids (e.g. myristic acid), peptides [see Dennis, M. S. et al J. Biol. Chem. 2002, 277, 35035], polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in *Enzymes as Drugs*. Hocenberg and Roberts, eds. (Wiley-Interscience: New York, N.Y.) pp. 367-383; and Newmark, et al. (1982) J. Appl. Biochem. 4:185-189].

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The peptide (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the peptide (or derivative) may be formulated (such as by liposome or microsphere encapsulation) and then further contained within an edible product, such as a refrigerated beverage containing colorants and flavoring agents.

One may dilute or increase the volume of the peptide (or derivative) with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders. and can include powdered gums such as agar, Karaya or tragacanth. Alginic acid and its sodium salt are also useful as disintegrants.

Binders may be used to hold the peptide (or derivative) agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation of the peptide (or derivative) to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the peptide (or derivative) are for instance the fatty acids oleic acid, linoleic acid and linolenic acid.

Controlled release oral formulations may be desirable. The peptide (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptide (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Parenteral Delivery

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Rectal or Vaginal Delivery

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

Pulmonary Delivery

Also contemplated herein is pulmonary delivery of the EPO-R agonist peptides (or derivatives thereof). The peptide (or derivative) is delivered to the lungs of a mammal while inhaling and traverses across the lung epithelial lining to the blood stream [see, e.g., Adjei, et al. (1990) Pharmaceutical Research 7:565-569; Adjei, et al. (1990) Int. J. Pharmaceutics 63:135-144 (leuprolide acetate); Braquet, et al. (1989) J. Cardiovascular Pharmacology 13(sup5):143-146 (endothelin-1); Hubbard, et al. (1989) Annals of Internal Medicine, Vol. III, pp. 206-212 (α1-antitrypsin); Smith, et al. (1989) J. Clin. Invest. 84:1145-1146 (α-1-proteinase); Oswein, et al. (1990) "Aerosolization of Proteins", Proceedings of Symposium on Respiratory Drug Delivery II Keystone, Colo. (recombinant human growth hormone); Debs, et al. (1988) J. Immunol. 140:3482-3488 (interferon-γ and tumor necrosis factor α); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.).

All such devices require the use of formulations suitable for the dispensing of peptide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified peptides may also be prepared in different formulations depending on the type of chemical modification or the type of device employed.

Formulations suitable for use with a nebulizer, either jet or ultrasonic, will typically comprise peptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the peptide (or derivative) caused by atomization of the solution in forming the aerosol.

Formulations for use with a metered-dose inhaler device will generally comprise a finely divided powder containing the peptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing peptide (or derivative) and may also include a bulking agent, such as lactose, sorbitol, sucrose, or mannitol in amounts which facilitate dispersal of the powder from the device, e.g., 50 to 90% by weight of the formulation. The peptide (or derivative) should most advantageously be prepared in particulate form with an average particle size of less than 10 mm (or microns), most preferably 0.5 to 5 mm, for most effective delivery to the distal lung.

Nasal Delivery

Nasal delivery of the EPO-R agonist peptides (or derivatives) is also contemplated. Nasal delivery allows the passage of the peptide to the blood stream directly after administering the therapeutic product to the nose, without the necessity for deposition of the product in the lung. Formulations for nasal delivery include those with dextran or cyclodextran.

Other penetration-enhancers used to facilitate nasal delivery are also contemplated for use with the peptides of the present invention (such as described in International Patent Publication No. WO 2004056314, filed Dec. 17, 2003, incorporated herein by reference in its entirety).

Dosages

For all of the peptide compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of between 0.001 to 10 mg/kg of body weight daily are administered to mammals. Generally, for intravenous injection or infusion dosage may be lower. The dosing schedule may vary, depending on the circulation half-life, and the formulation used.

The peptides of the present invention (or their derivatives) may be administered in conjunction with one or more additional active ingredients or pharmaceutical compositions.

EXAMPLES

The following Examples illustrate the invention, but are not limiting.

Example 1

General Synthesis of a Trifunctional Linker

Branched trifunctional molecules having the structure:

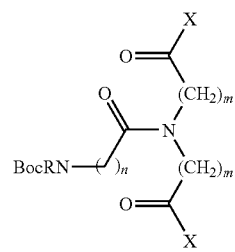

$m = 1\text{-}5, n = 1\text{-}14, m$ and $n$ are integers, R = H or alkyl wherein -continued

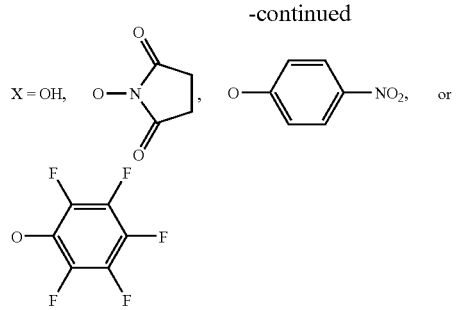

were synthesized according to the following reaction scheme:

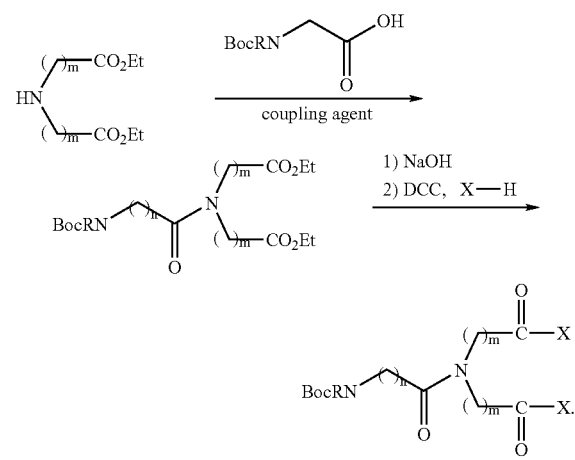

m = 1-5, n = 1-14, m and n are integers, R = H or alkyl

N-terminus protected amino acids such as Boc-beta-alanine (Boc=tert-butoxycarbonyl) are coupled to iminodiesters such as diethyl iminodiacetate with carbodiimide reagents such as dicyclohexyl-carbodiimide (DCC). After extractive workup and isolation, the ester groups are saponified to generate the desired trifunctional linkers. The acid groups are activated as the NHS ester by treatment with N-hydroxysuccinimide (NHS) and dicyclohexyl-carbodiimide in acetonitrile (ACN). Filtration of the precipitated urea and extractive workup affords the NHS activated linkers. Trituration from dichloromethane/hexane affords the linkers as white solids, which have been found to be stable for months at −20° C.

See Examples 2 and 22 for non-limiting, detailed syntheses of linkers.

Example 2

Synthesis of a Trifunctional Linker

A first trifunctional molecule having the structure

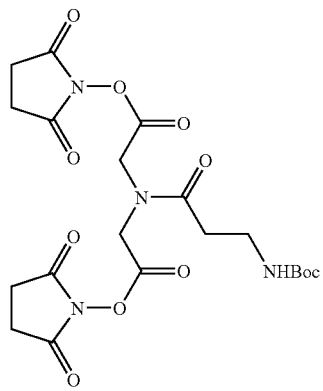

was made according to the following:
Step I

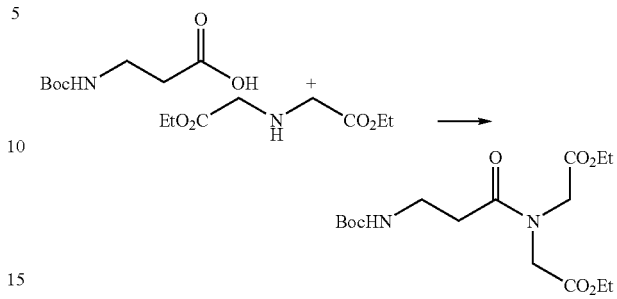

To a solution of Boc-β-Ala-OH (10.0 g, 52.8 mmol) and diethyl iminodiacetate (10.0 g, 52.8 mmol) in 200 mL of DCM at 0° C. was added DCC (10.5 g, 50.9 mmol) over 5 min. A white precipitate formed within 2 min. The reaction mixture was allowed to warm to room temperature and was stirred for 24 h. The urea was filtered off with a sintered filter (medium porosity) and the solvent removed under reduced pressure. The residue was taken up in 500 mL of EtOAc (EtOAc=ethyl acetate), filtered as above, and transferred to a separatory funnel. The organic phase was washed (sat. NaHCO$_3$, brine, 1 N HCl, brine), dried (MgSO$_4$), filtered, and dried to yield a colorless oil. The oil solidified to yield a white crystalline solid within 10 min.

Step II

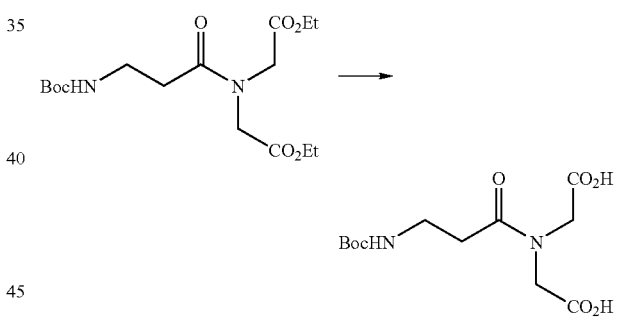

The crude diester was taken up in 75 mL of THF (THF=tetrahydrofurane) and 75 mL of MeOH (MeOH=methanol) and 50 mL of water was added. To this solution was added a solution of KOH (KOH=potassium hydroxide) (8.6 g, 153 mmol) in 25 mL of water. The reaction mixture turned light yellow in color. After stirring for 12 h (pH was still ~12), the organic solvent was removed on a rotary evaporator and the resultant slurry partitioned between Et$_2$O (Et$_2$O=Diethyl ether) and sat. NaHCO$_3$. The combined aq. phase was acidified to pH 1, saturated with NaCl, and extracted with EtOAc. The EtOAc phase was washed (brine), dried (MgSO$_4$), and concentrated to yield 13.97 g of product as a white solid (90.2% for 2 steps).

Notes: the yield dropped to 73% when the DCC reaction was performed in ACN. When using diisopropylcarbodiimide (DIC), the urea byproduct could not be removed from the desired product without chromatography; the DCC urea can be quantitatively removed without chromatography. The reaction also works well with water-soluble carbodiimide.

Step III

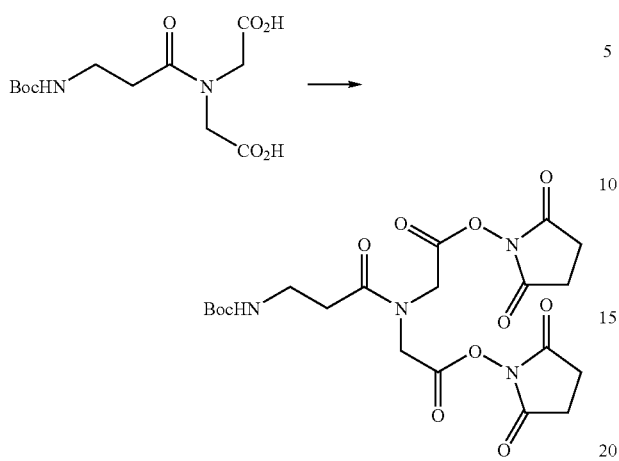

To a solution of diacid (1.00 g, 3.29 mmol) and hydroxysuccinimide (0.945 g, 8.21 mmol) in 50 mL of ACN was added DCC (1.36 g, 6.59 mmol) over 5 min. A white ppt formed immediately. The reaction mixture was stirred 22 h and was filtered to remove the DCC urea. The solvent was removed under reduced pressure and the residue taken up in EtOAc (250 mL) and transferred to a separatory funnel. The organic phase was washed (sat. $NaHCO_3$, brine, 1 N HCl, brine), dried ($MgSO_4$), and concentrated to afford a white solid. The solid was taken up in 75 mL of ACN, filtered, and concentrated to yield 1.28 g of product as a white solid (78.2% yield).

Notes: the yields dropped to 31% in THF, 68% in DMF (with DIC instead of DCC), and 57% in DCM/DMF. The starting diacid is soluble in ACN, so if there is any material which has not dissolved before the DCC is added, it may be filtered off and discarded.

Example 3

C-Terminus Dimerization and Subsequent PEGylation Using a Trifunctional Amine Linker

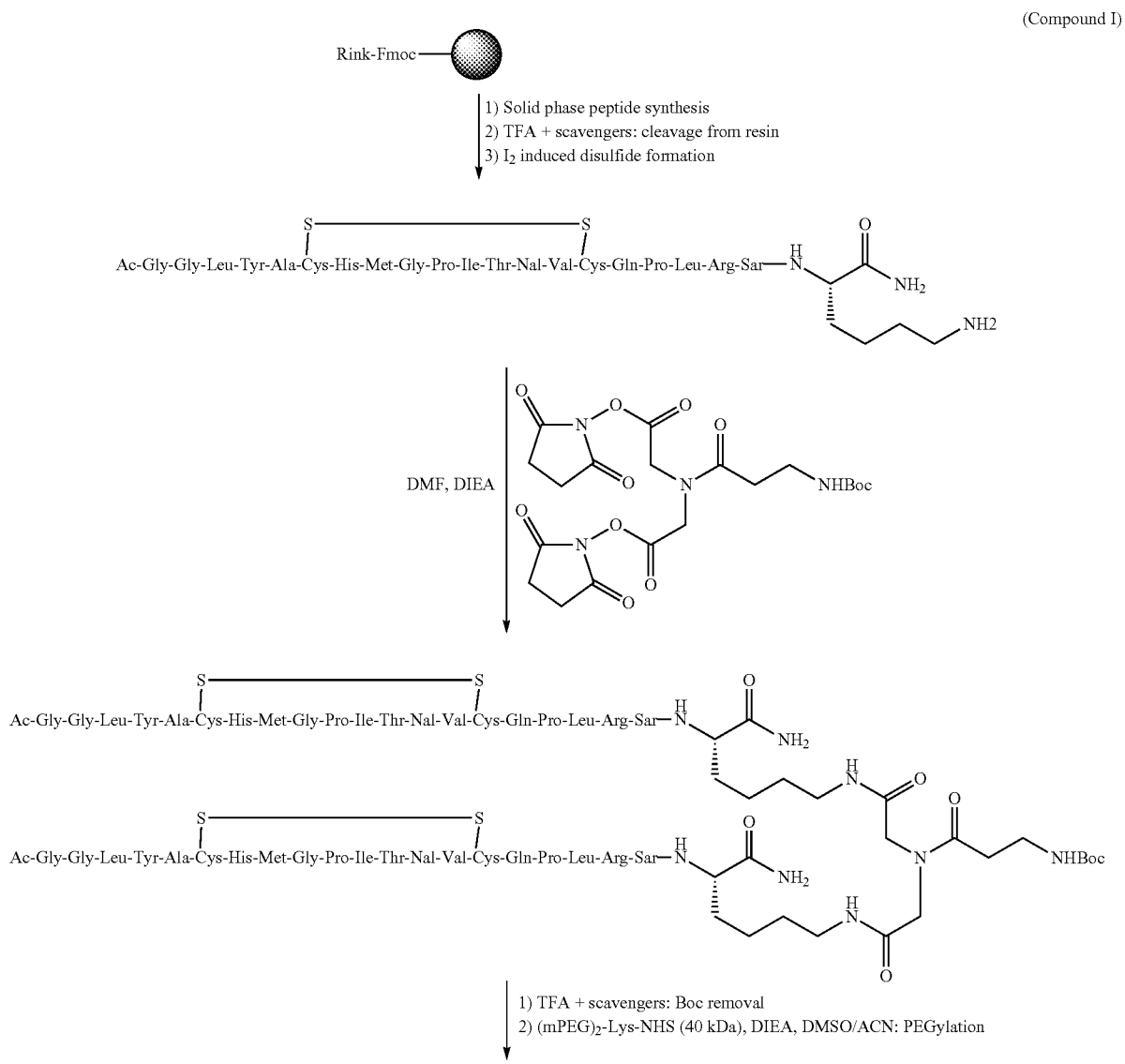

(Compound I)

-continued

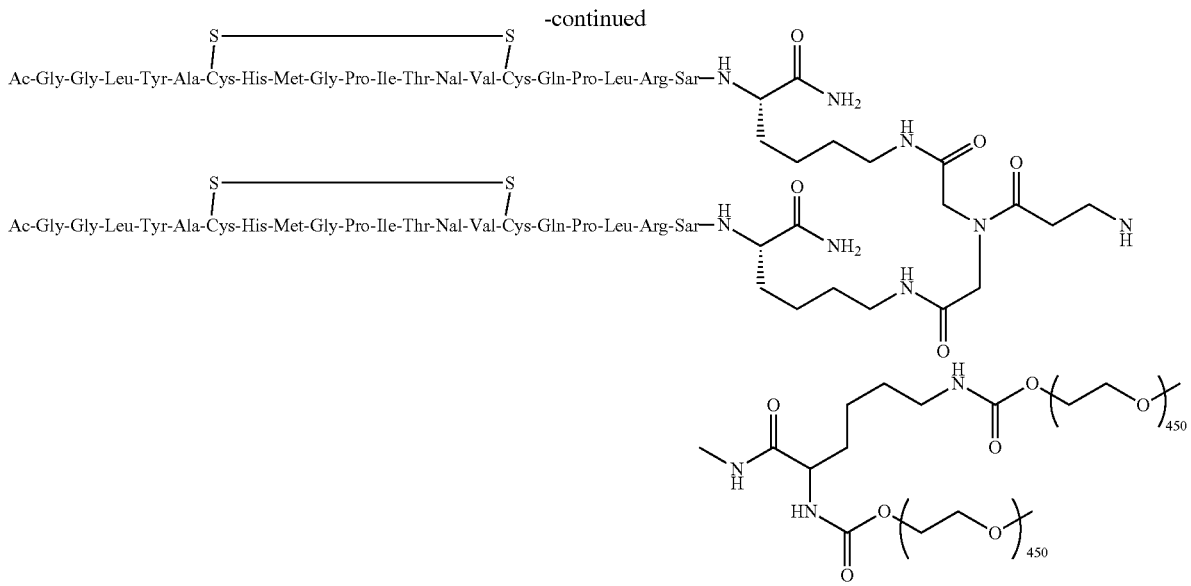

Peptide Synthesis:

The monomeric peptide (using SEQ ID NO: 5) was synthesized on 30 g of TentaGel Rink Amide resin using standard Fmoc-amino acids (TFA-labile side chain protecting groups) and diisopropylcarbodiimide (DIC)/hydroxybenzotriazole (HOBt) couplings on an ACT90 peptide synthesizer (from Advanced ChemTech, Louisville, Ky.). The resin was treated with a solution of 85% trifluoroacetic acid (TFA), 10% triisopropylsilane (TIPS), 2.5% thioanisole, 2.5% $H_2O$ 3 times, each time using 200 mL of the cleavage cocktail (agitated for 2 h the first time, then 1 h each for the next two times) and then rinsed with 100 mL of TFA. The cleavage cocktail containing the peptide was concentrated under reduced pressure to ~50 mL and was added to a 5-fold excess of cold ether to precipitate the peptide. The precipitate was washed twice with ether and was freeze dried on a lyophilizer to afford 11.4 g of the crude monomer. This monomer was dissolved into 300 mL of trifluoroethanol (TFE). A 50 mL aliquot of this solution was added to a solution of 600 mL of MeOH and 400 mL of TFE. Saturated $I_2$ in acetic acid was added drop wise with stirring until the yellow color persists. The addition of 50 mL of peptide solution in TFE to the MeOH/TFE solution followed by the addition of $I_2$/AcOH was repeated another five times to complete the oxidation. The reaction mixture was analyzed by RP-HPLC and LC/MS techniques to monitor the reaction. When complete, solid ascorbic acid was added until the solution became clear. The solvent mixture was concentrated to ~50 mL under reduced pressure, and was added to a 5-fold excess of cold ether to precipitate the peptide. The precipitate was washed twice with ether followed by purification on RP-HPLC (Kromasil C18, mM, 100 Å C18 support, 7.5×20.5 cm axial compression column, mobile phase A: water containing 0.12% TFA, mobile phase B: acetonitrile (ACN) containing 0.1% TFA, gradient of 10% B for 10 min, change to 25% B over 2 min, then to 35% B over 60 min, flow rate 125 mL/min). Fractions containing product were freeze-dried on a lyophilizer. Fractions of purity above 95% were dissolved in ACN/water, combined, and freeze-dried on a lyophilizer to afford the peptide as a white solid.

Dimerization Reaction:

Monomer (3 g, 1.27 mmol) from above was dissolved in 30 mL of anhydrous dimethyl sulfoxide (DMSO). Diisopropylethylamine (DIEA) (6.3 mmol, 5 eq.) was added and the mixture was stirred until homogenous. A stock solution of the tetrafunctional activated linker in DMSO at 30 mg/mL was prepared and a portion of this (0.55 eq.) was added to the peptide solution with stirring, After 2 h, the reaction mixture was analyzed by HPLC/LCMS. After completion of the reaction, water (200 microliters) was added to the reaction mixture and the solution freeze-dried on a lyophilizer. The dry powder was purified (reversed-phase HPLC on C18 support, elute with an acetonitrile/water/0.1% TFA gradient from 10% ACN to 35% ACN over 60 min) to obtain pure Boc-protected dimer. The Boc-protected dimer was treated with 10 mL of 95% TFA/$H_2O$ for 15 min followed by precipitation in a 5-fold excess of cold ether. The precipitate was washed twice with cold ether to obtain the crude dimer, which was purified using the same reversed phase HPLC method as above to afford 1.8 g of pure dimer peptide.

PEGylation Reaction:

The peptide (100 mg, 0.020 mmol) from above was dissolved in 2 ml of an 80:20 mixture of DMSO: acetonitrile. Activated 40 kDa (mPEG)$_2$-Lys-NHS (1.23 g, 0.030 mmol, from Nektar Therapeutics, San Carlos, Calif.) was added and the reaction mixture stirred vigorously until it became homogeneous. DIEA (69 μL, 0.4 mmol) was added and the reaction mixture was analyzed after 2 h by HPLC to reveal a complete reaction. The peptide was precipitated by addition of 20 mL of cold anhydrous diethyl ether. The precipitate obtained was washed twice with cold ether and the PEGylated peptide was purified by strong cation exchange chromatography (Source 15S 15 μm support, dissolve and load peptide in mobile phase A: 35% ACN/water containing 0.2% HOAc, gradient elute using mobile phase B: 100 mM NH$_4$OAc in 35% ACN/water containing 0.2% HOAc, 125 mm×35 mm column dimension, gradient: 2% B to 20% B over 10 min, to 100% B over 65 min). Free PEG eluted during the void volume. Fractions containing product were freeze-dried on a lyophilizer to afford 1.2 g of PEGylated peptide as a white powder.

Example 4

General Synthesis of Trifunctional Amine Linkers

Trifunctional, activated, amine linkers having the following structure:

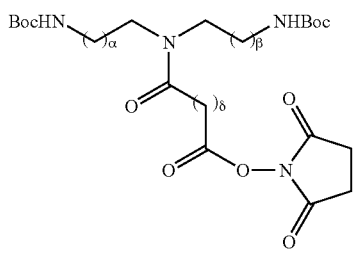

wherein α is an integer, 1≤α≤7; β is an integer, 1≤β≤7; and δ is an integer, 2≤δ≤5; were synthesized according to the following reaction scheme:

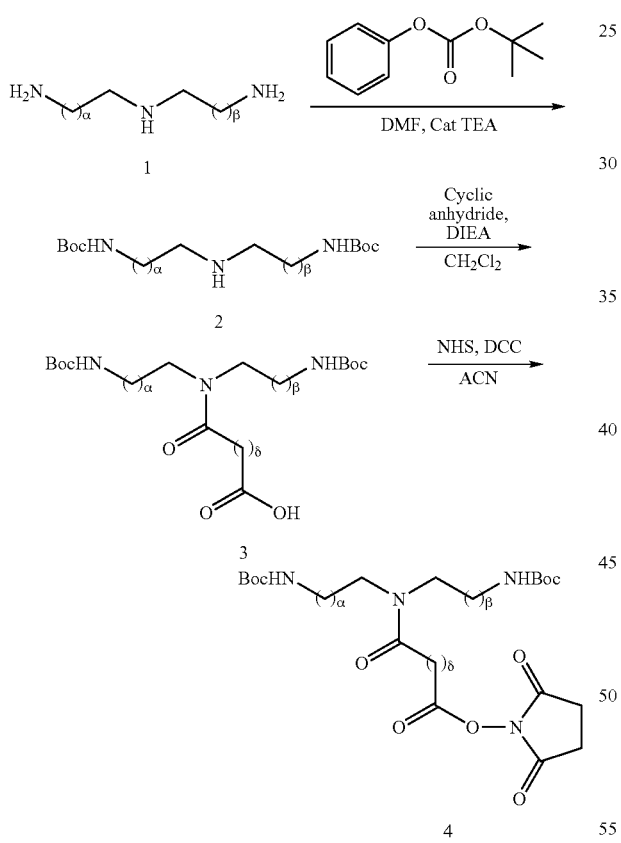

Commercially available triamino compounds 1 are treated with tert-butyl phenyl carbonate in dimethyl formamide (DMF) in the presence of a catalytic amount of triethylamine (Cat TEA) for 24 h to provide the di-tert-butyl carbamate intermediate 2. Treatment of 2 with glutaric anhydride and diisopropylethylamine (DIEA) in methylene chloride produces the diamino free acid 3. The acid group is activated as the NHS ester by treatment with N-hydroxysuccinimide (NHS) and dicyclohexylcarbodiimide (DCC) in acetonitrile (ACN). Filtration of the precipitated urea and extractive workup affords the NHS activated linkers. Trituration from DCM/hexane affords the linkers as white solids, which have been found to be stable for months at −20° C.

See Example 5 for a non-limiting, detailed synthesis of this linker.

Example 5

Synthesis of a Trifunctional Amine Linker and Activation as its NHS Ester

A trifunctional, activated amine linker having the structure

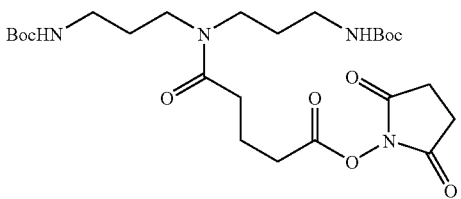

was made according to the following procedure:

Step I

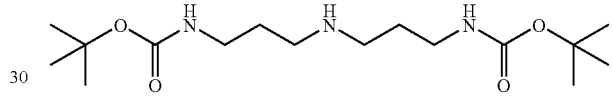

t-Butyl phenyl carbonate (20 mL, 0.11 mole) was added drop-wise to a solution of N-(3-aminopropyl)-1,3-propanediamine (0.05 mole) in anhydrous DMF (50 mL). To this solution was added $Et_3N$ (5 mL). The resulting mixture was stirred at room temperature overnight. The mixture was poured into a phosphate buffer (2 L, 0.025 M $K_2HPO_4$ and 0.025 M $NaH_2PO_4$), and the resulted solution was adjusted to pH ~3 with 2 M $H_2SO_4$ with vigorous stirring. The mixture was extracted with DCM (2×250 mL) and the organic extracts were discarded. The aqueous layer was basified with aq. 9 N NaOH; and then was extracted with DCM (3×250 mL). The organic extracts were dried over $Na_2SO_4$, concentrated under reduced pressure, and then dried under vacuum overnight to give the desired product (15 g, 90% yield).

Step II

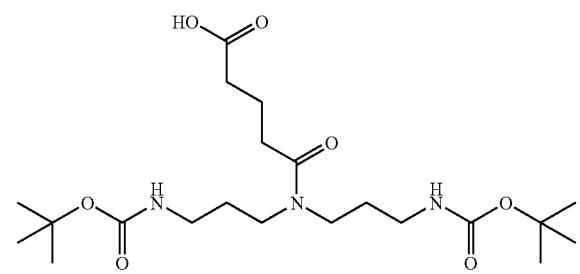

A mixture of di-BOC protected amine (5 g, 15 mmol), glutamic anhydride (1.64 g, 14.25 mmol), and $Et_3N$ (3 mL, 22.5 mmol) in anhydrous DCM (50 mL) was stirred at room temperature overnight. The solvent was removed under reduced pressure and the residue dissolved in water. The aqueous solution was acidified with 1N HCl at 4-10° C. to pH ~3, and then extracted with DCM (3×150 mL). The combined extracts were washed with sat. NaCl, dried over Na$_2$SO$_4$, and then concentrated under reduced pressure to yield the desired product (6 g, 90%)

Step III

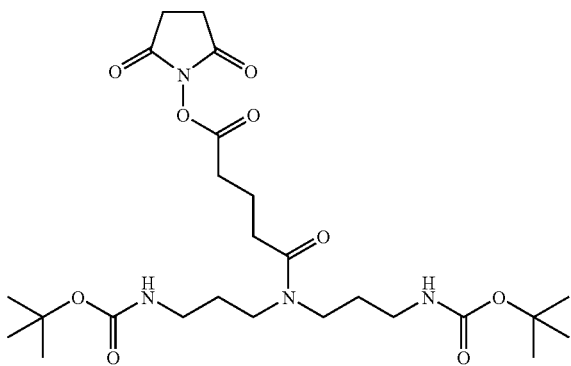

A mixture of the above Step II mono-acid product (2 g, 5.78 mmol) and N-hydroxysuccinimide (731 mg, 6.36 mmol) in anhydrous DCM (50 mL) was cooled to 4° C. in an ice-bath. N-(3-dimethylaminopropyl)-N'-ethylcarbodiimide hydrochloride (EDCI) (1.4 g, 8.7 mmol) was added in portions to the reaction mixture. The resulting mixture was then warmed to room temperature and stirred for 2 hours. After removal of solvent under reduced pressure, the residue was partitioned between ethyl acetate and water. The aqueous layer was extracted with EtOAc (2×100 mL). The combined organic layer was washed with 1 M NaHCO$_3$ (1×100 mL) followed by water (5×100 mL), and sat. NaCl (1×100 mL). The extracts were dried over Na$_2$SO$_4$, concentrated, and dried under vacuum to give the final activated trifunctional linker as a semi-solid (4.9 g, 85%).

Example 6

Conjugation to a Peptide and Subsequent PEGylation of a Trifunctional Linker

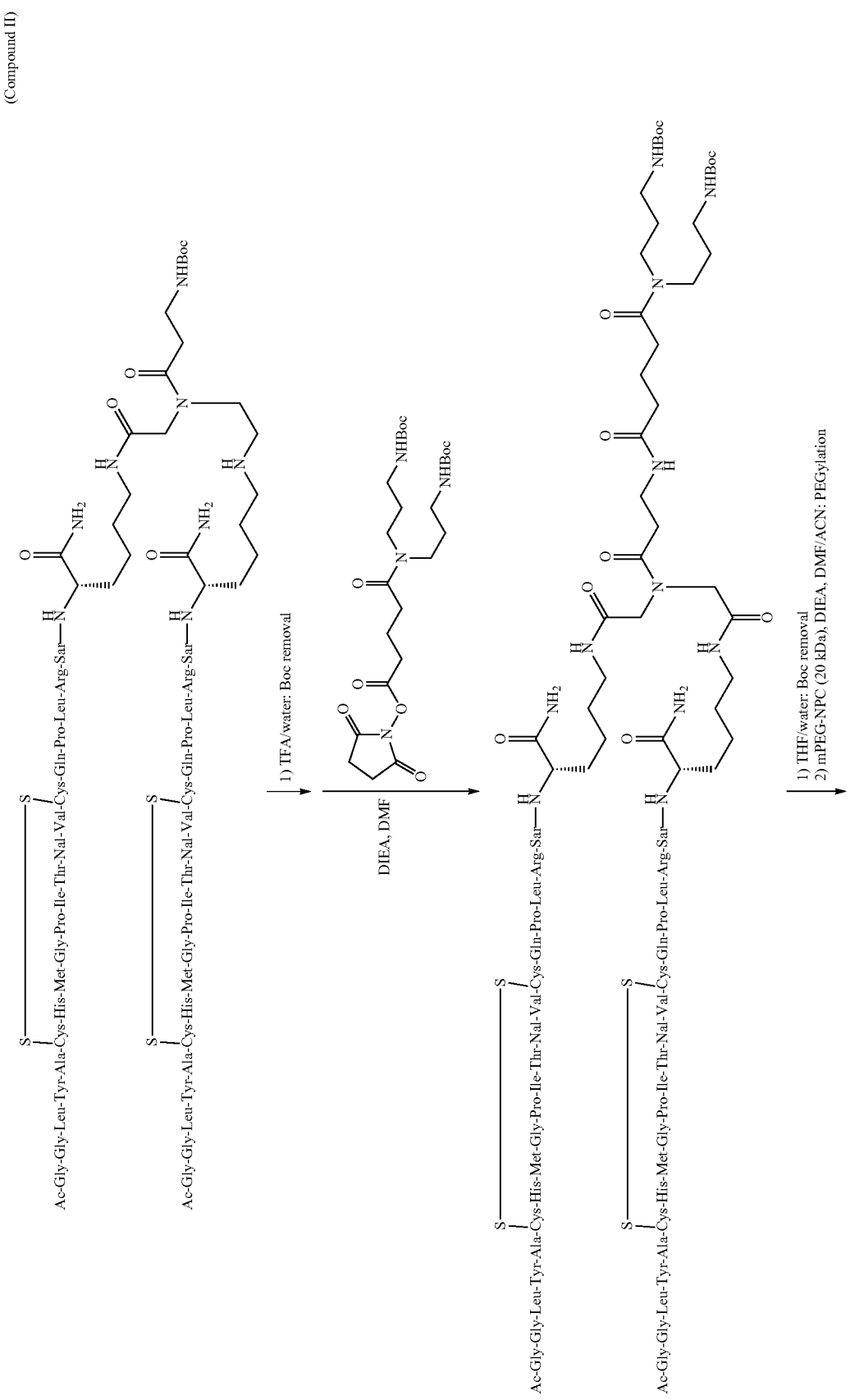

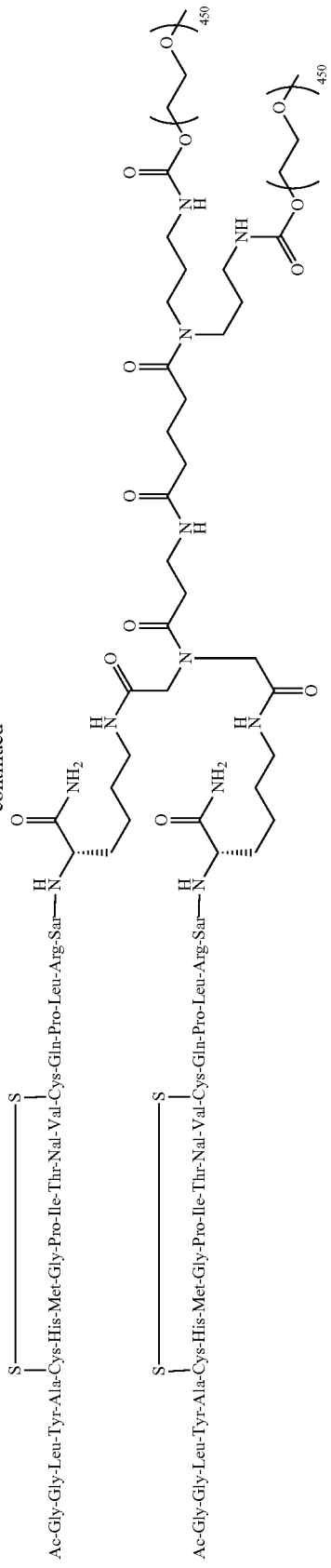

The dimer peptide from Example 3 (using SEQ ID NO: 5) was used as starting material for this example, in order to synthesize Compound II. Removal of the Boc group was effected with 95% TFA/water. The peptide was precipitated from cold ether and was purified via HPLC on a C18 column using a TFA/ACN/0.1% TFA gradient. Fractions containing the product were freeze-dried on a lyophilizer to afford the free amine-peptide as a white solid. A solution of peptide (20 mg, 1 eq.) and DIEA (10 microliters, 10 eq.) in 0.5 mL of DMF and was treated with the trifunctional activated linker from Example 5 (4.5 mg, 2 eq.). HPLC analysis after stirring overnight revealed a nearly complete reaction. The reaction mixture was added to cold ether to precipitate the peptide. The bis-Boc protected linker-peptide conjugate was dried under reduced pressure.

The two Boc groups were removed by dissolving the peptide in a solution of 1.9 mL of TFA and 0.1 mL of water and stirring for 1 h. The TFA was removed under educed pressure and the residue was precipitated from cold ether. The bis-amine peptide was purified via HPLC on a C18 column using a TFA/ACN/0.1% TFA gradient. Fractions containing the desired peptide were freeze-dried on a lyophilizer.

PEGylation Reaction:

To a solution of bis-amine peptide (10 mg, 1 eq.) in 0.5 mL of DMF was added DIEA (7 microliters, 20 eq.) followed by mPEG-NPC 20 kDa (NOF Corp., 120 mg, 3 eq.). An additional aliquot of mPEG-NPC (40 mg) and ACN (~50-100 microliters) were added after 6 h. Analysis after 14 h by ion exchange chromatography revealed a complete reaction. The reaction mixture was diluted with 20% ACN/water containing 0.2% HOAc and was purified by strong cation exchange chromatography (Source 15S 15 μm support, gradient elute using 100 mM NH$_4$OAc in 20% ACN/water containing 0.2% HOAc). Free PEG eluted during the void volume. Fractions containing product were freeze-dried on a lyophilizer to afford 51 mg of PEGylated peptide as a white powder.

Example 7

Synthesis of a Tetrafunctional Linker and Activation as its NHS Ester

The tetrafunctional, activated linker having the structure

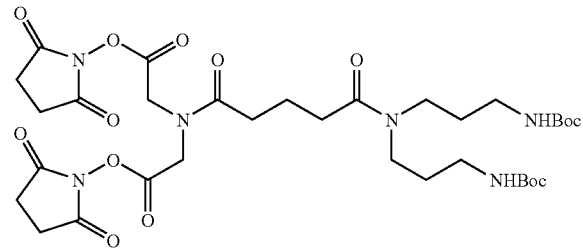

was synthesized according to the following scheme

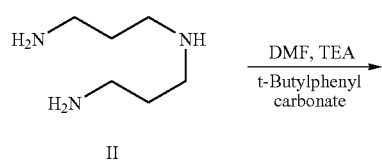

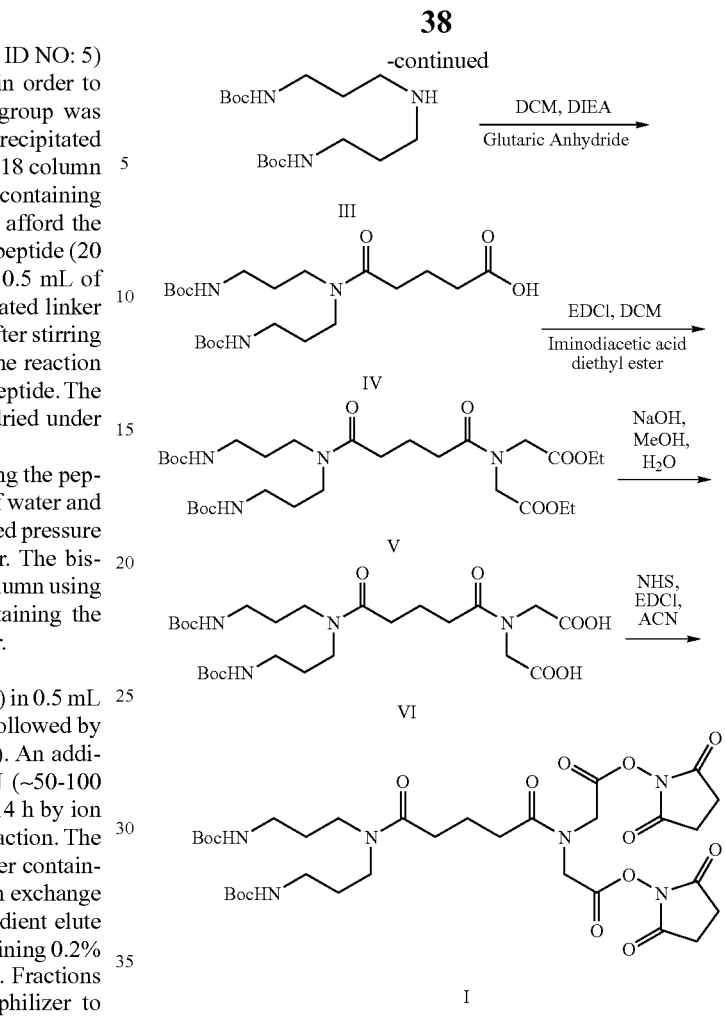

Di-t-butyloxy Triamine (III):

To a solution of triamine (II) (0.05 mole) in DMF (50 mL) was added the t-butyl phenyl carbonate (2.3 eq.). The reaction mixture was stirred overnight at room temperature and poured into phosphate buffer (1 L of 0.05 M K$_2$HPO$_4$ and 0.05 M NaH$_2$PO$_4$). The pH was adjusted to 3 with 2 M H$_2$SO$_4$ and extracted with diethyl ether (3×250 mL). The aq. phase was made strongly alkaline with 10 N NaOH and extracted with DCM (4×250 mL). The organic phase was washed with brine, dried over sodium sulphate, and concentrated under reduced pressure to provide the bis protected triamine (III) as a white solid (yield ~60%).

DiBoc Amino Acid (IV):

A mixture of diBoc triamine (III) (0.01 mole) and glutaric anhydride (0.01 mole) in anhydrous DCM (25 mL) was cooled to 5° C. (ice-water bath). Anhydrous TEA (0.015 mole, 1.5 eq.) was added and the mixture was stirred at room temperature for 6 hours. The mixture was diluted with more DCM and washed with 1 N NaHCO$_3$ (twice). The organic layer was discarded. The water layer was acidified to pH 3.0 with 2 NHC and extracted with ethyl acetate (thrice). The ethyl acetate layer was washed with water and brine, dried over sodium sulphate, and concentrated under reduced pressure to provide (IV) as a white sticky solid (yield ~90%).

Diethyl Ester Linker (V):

The diBoc amino acid (IV) (0.01 mole) and diethyl iminodiacetate (0.01 mole) were dissolved in anhydrous dichloromethane. To this was added N-(3-dimethylaminopropyl)-N'-ethylcarbodiimide hydrochloride (EDCI) (0.012 mole)

and the reaction mixture was stirred at room temperature overnight. The mixture was diluted with more DCM and washed with 0.1 N HCL, ice cold 1 N NaHCO$_3$, water (3 times), and brine. The DCM layer was dried over sodium sulphate and concentrated under reduced pressure to provide diethyl ester linker (V) as sticky semi-solid.

Diacid Ester Linker (VI):

The diethyl ester linker (V) from the previous step as dissolved in a 1:1 mixture of 1 N NaOH and MeOH and stirred at room temperature for 6 hrs. The MeOH was removed under reduced pressure and the residue diluted with water. The solution was washed with DCM (twice). The aqueous layer was neutralized with cold 1 N HCL and extracted with ethyl acetate (3 times). The organic layer was washed with brine, dried over sodium sulphate, and concentrated under reduced pressure to provide the tetrafunctional linker (VI) as a white solid (yield ~65%, two steps).

Activated Tetrafunctional Linker (I):

The diacid linker (VI) from above (0.005 mole) and N-hydroxysuccinimide (0.015 mole, 3 eq.) were dissolved in anhydrous acetonitrile. To this was added N-(3-dimethylaminopropyl)-N'-ethylcarbodiimide hydrochloride (EDCI) (0.0125 mol, 2.5 eq.) and the reaction mixture was stirred at room temperature overnight. The mixture was diluted with DCM and washed with ice cold water (5 times) and brine. The DCM phase was dried over sodium sulphate and concentrated under reduced pressure to provide the activated tetrafunctional linker (I) as white solid (yield ~85%). The structure of the linker was confirmed by $^1$H-NMR.

Example 8

Peptide Dimerization Using a Tetrafunctional Linker and Subsequent PEGylation

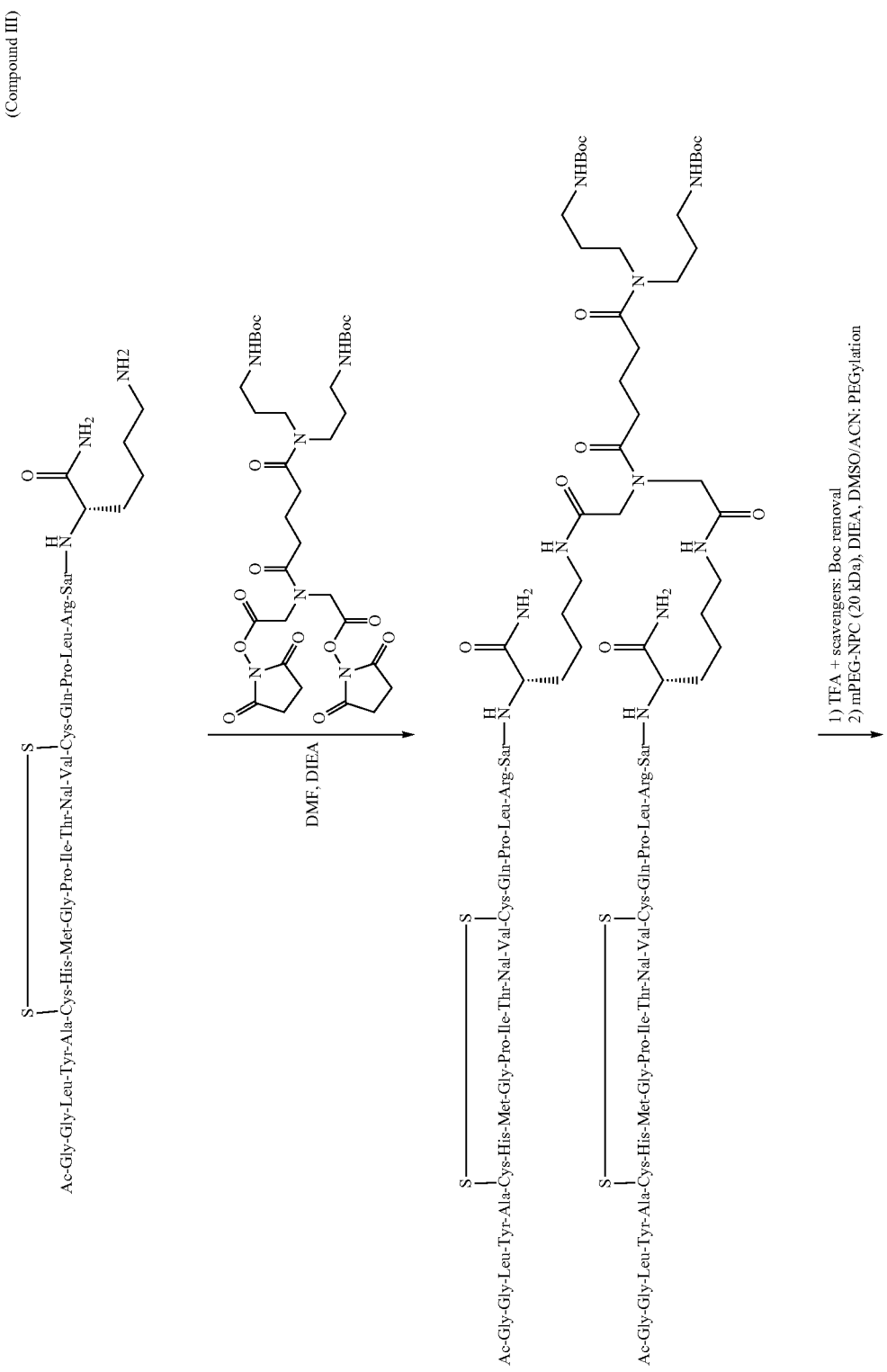

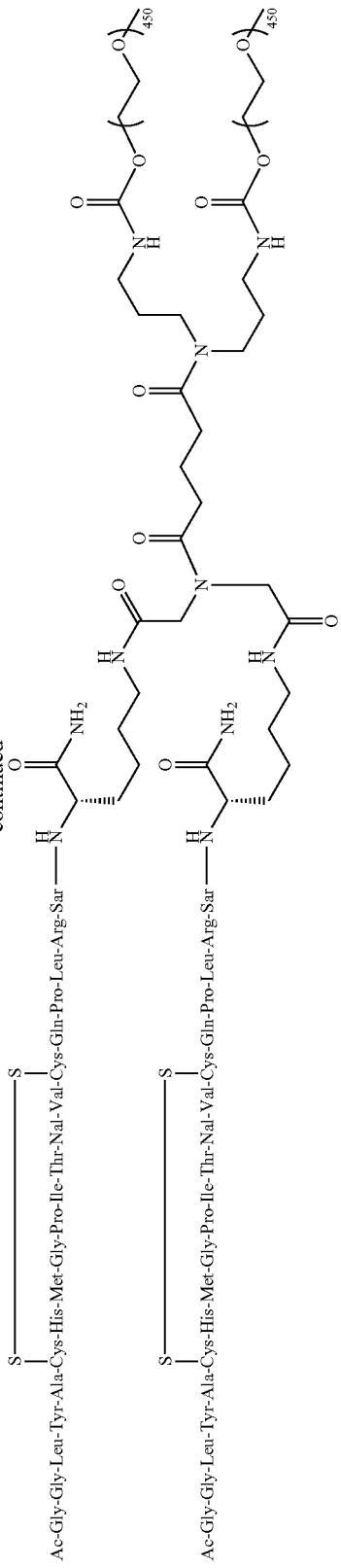
-continued

The peptide monomer was prepared as in Example 3 (using SEQ ID NO: 5), and use as the initial molecule in the synthesis of Compound III. To a solution of peptide (150 mg, 2 eq.) and DIEA (56 microliters, 10 eq.) in 0.4 mL of DMF was added tetrafunctional activated linker from Example 7 (23 mg, 1 eq.). HPLC analysis after stirring overnight revealed a complete reaction. The peptide was precipitated from cold ether and dried under reduced pressure. The two Boc groups were removed by dissolving the peptide in a solution of 1.9 mL of TFA and 0.1 mL of water and stirring for 1 h. The TFA was removed under educed pressure and the residue was precipitated from cold ether. The bis-amine peptide was purified via HPLC on a C18 column using a TFA/ACN/0.1% TFA gradient Fractions containing the desired peptide were freeze-dried on a lyophilizer.

PEGylation Reaction:

mPEG-NPC 20 kDa (NOF Corp., 596 mg, 3 eq.) was dissolved in minimal 70:30 mixture of DMSO:ACN. To this solution was added bis-amine peptide (50 mg, 1 eq.) and DIEA 17 microliters, 10 eq.). Analysis after 5 h by ion exchange chromatography revealed a complete reaction. The reaction mixture was added to cold ether to precipitate the PEGylated peptide. The PEGylated peptide was dissolved in 35% ACN/water containing 0.2% HOAc and was purified by strong cation exchange chromatography (Source 15S 15 μm support, gradient elute using 100 mM NH₄OAc in 35% ACN/water containing 0.2% HOAc). Free PEG eluted during the void volume. Fractions containing product were freeze-dried on a lyophilizer to afford 360 mg of PEGylated peptide as a white powder.

Example 9

Synthesis of Tetrafunctional Linker and Activation as its NHS Ester

The tetrafunctional, activated, linker having the structure:

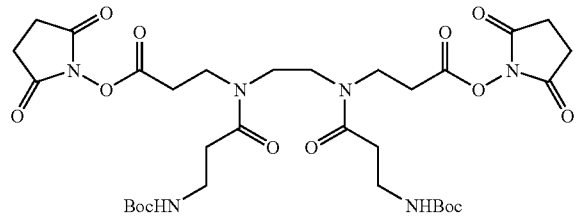

was synthesized according to following steps:
Step I

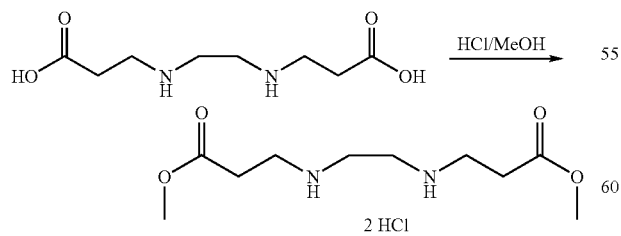

To a flask containing 400 mL of methanol was added acetyl chloride (8 mL, 112 mmol). The solution was stirred for 10 min and ethylenediamine-N,N'-dipropionic acid dihydrochloride from TCI America (Portland, Oreg.) (25.0 g, 90.2 mmol) was added and the reaction mixture was heated to reflux for 24 hrs. The solution was cooled to RT and then placed in a freezer for 14 hrs. The white crystals were collected by filtration and dried under reduced pressure to yield 27.12 g of diamine dihydrochloride salt product.

Step II

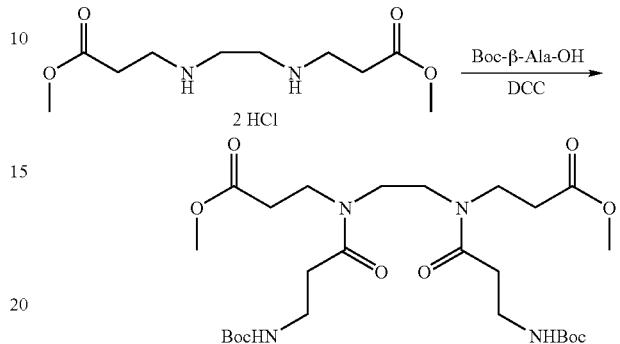

The diamine dihydrochloride salt (5.0 g, 16.4 mmol) was free-based by dissolving in 50 mL of water, transferring to a separatory funnel, adding 100 mL of saturated NaHCO₃ and 25 mL of saturated NaCl (pH of aq. phase was approximately 10), and extracted four times with chloroform, and dried over Na₂SO₄. Removal of the solvent afforded 1.12 g of colorless oil. The aqueous phase from above was further basified to pH 12 with an aqueous solution of NaOH, and was extracted four times with chloroform. Drying over Na₂SO₄ and removal of the solvent afforded an additional 2.33 g of colorless oil.

The combined free-base (3.45 g, 14.8 mmol) was dissolved in 125 mL of acetonitrile, Boc-β-alanine-OH (4.36 g, 23.0 mmol) was added, an ice water bath was placed under the flask, followed by the addition of dicyclohexylcarbodiimide (4.74 g, 22.97 mmol) to the flask. The reaction mixture was allowed to warm to RT, stirred 24 h, and then was filtered to remove precipitated urea. The solvent was removed under reduced pressure and the residue taken up in 250 mL of ethyl acetate and washed sequentially with saturated NaHCO₃, saturated NaCl, 1 N HCl, and saturated NaCl. The organic phase was dried over MgSO₄, filtered, and concentrated under reduced pressure to afford 6.03 g (91% yield) of white solid.

Step III

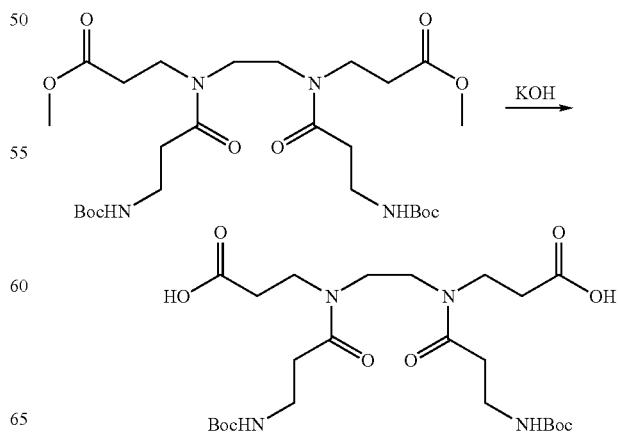

Crude dimethyl ester from above (6.03 g, 10.5 mmol) was dissolved in a mixture of 75 mL of methanol and 50 mL of tetrahydrofuran, and 30 ml of water. A solution of KOH (1.89 g, 33.7 mmol) in 20 mL of water was added at RT. HPLC analysis after 2 hrs showed complete conversion to product. The organic solvents were removed under reduced pressure after 3.5 hrs. The solution was diluted with 100 mL of water, extracted with diethyl ether, acidified to below pH 2 with 6 N HCl, saturated with solid NaCl, and extracted into ethyl acetate. The organic phase was dried over $MgSO_4$, filtered, and concentrated under reduced pressure to afford a white semi-solid. The product was recrystallized from 10% methanol/water containing a small amount of HCl to afford 3.42 g of diacid as a white solid (60% yield).

Step IV

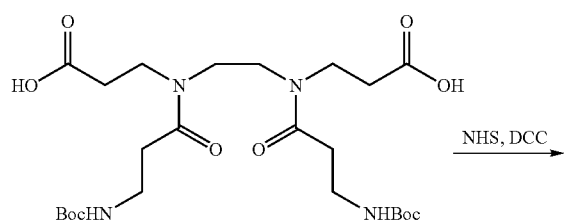

NHS, DCC

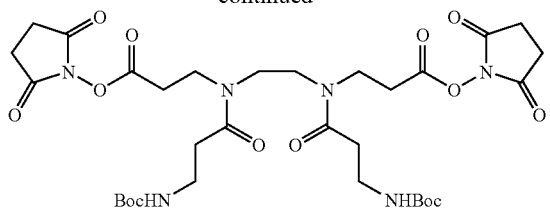

To a solution of the diacid from above (0.551 g, 1.01 mmol) and N-hydroxysuccinimide (0.28 g, 2.42 mmol) in 35 mL of DMF was added 1-(3-dimethylaminopropyl)-3-ethylcarbodiimide hydrochloride (0.408 g, 2.13 mmol). After stirring for 26 hrs, the solvent was removed under educed pressure and the residue partitioned between ethyl acetate and sat $NaHCO_3$. The organic phase was washed (sat NaCl, 2×10% $KHSO_4$, sat NaCl), dried ($MgSO_4$), filtered, and concentrated to afford 0.385 g (51.5% yield) of di-NHS activated ester product as a white solid.

Example 10

C-Terminus Dimerization of a Peptide and Subsequent PEGylation Using a Tetrafunctional Linker (Compound IV)

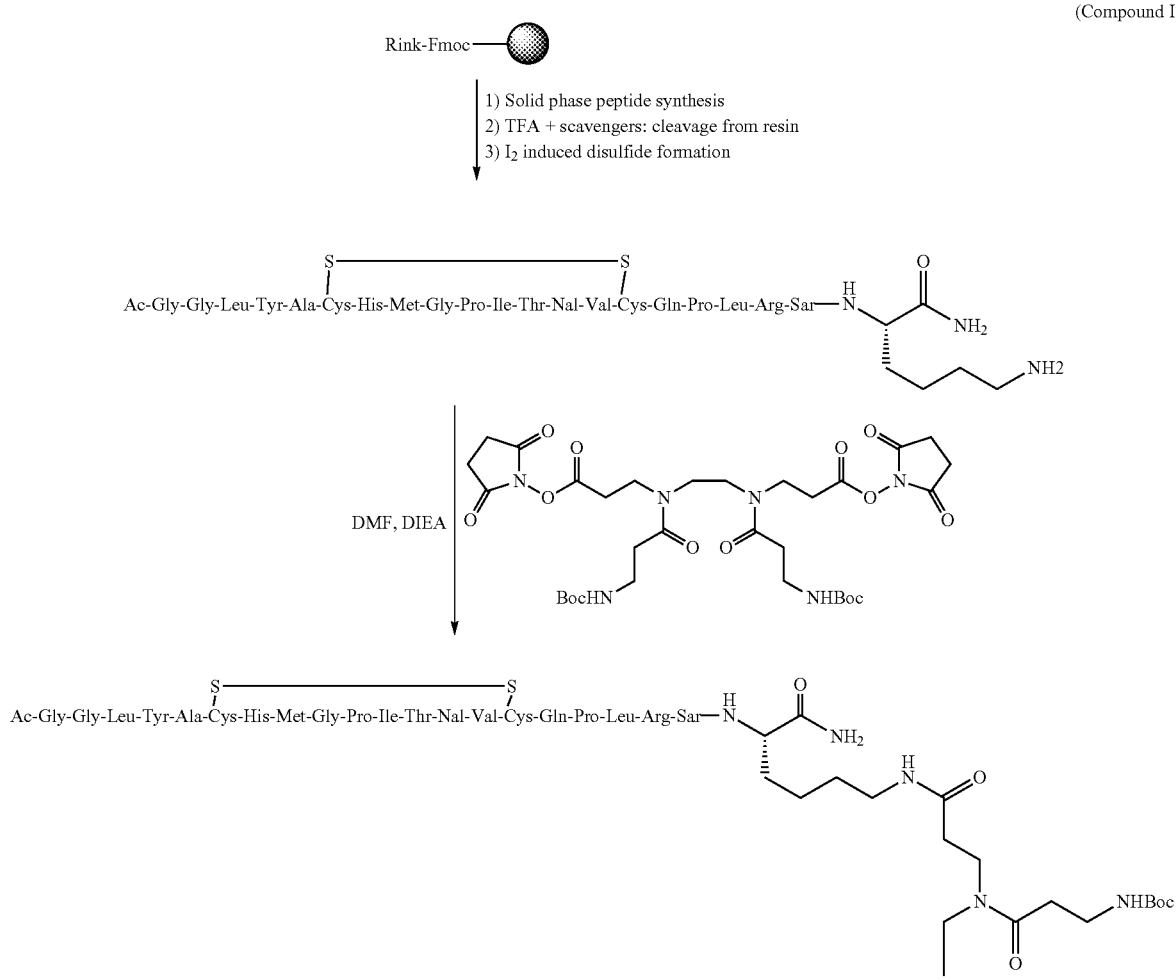

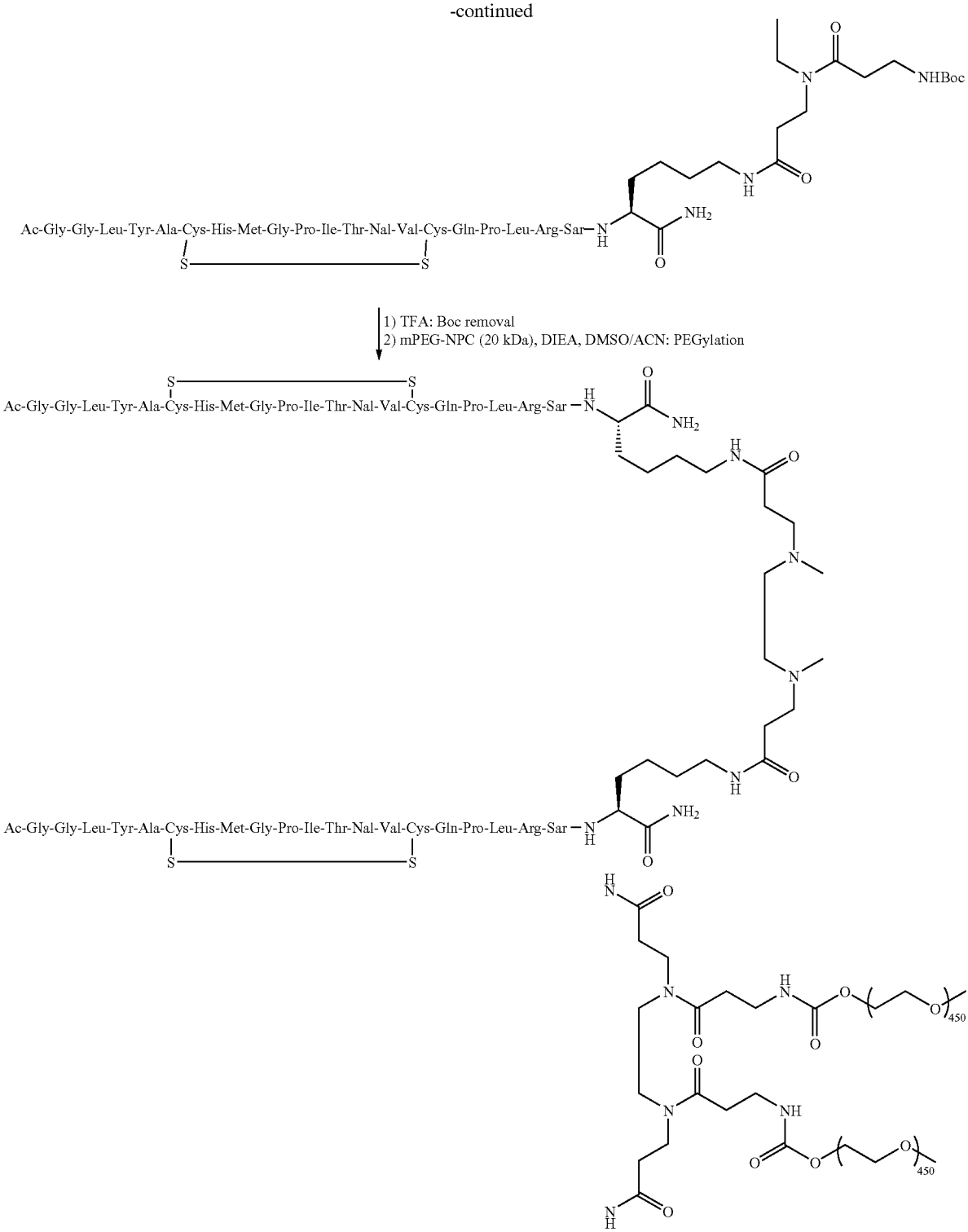

Peptide Synthesis:

The monomeric peptide (using the peptide given in SEQ ID NO: 5) was synthesized on 30 g of TentaGel Rink Amide resin using standard Fmoc-amino acids (TFA-labile side chain protecting groups) and diisopropylcarbodiimide (DIC)/hydroxybenzotriazole (HOBt) couplings (0.25 M, 4 eq, 2 h couplings) on an ACT90 peptide synthesizer (from Advanced ChemTech, Louisville, Ky.). The resin was cleaved with 85/10/2.5/2.5 TFA/TIPS/Thioanisole/water. The cleavage cocktail was reduced to one half its volume and precipitated with ether. The precipitate was taken up in TFE and diluted with MeOH to 2 mg/ml. To this stirring solution was added a saturated solution of $I_2$ in AcOH until the light yellow color remained. The solution was stirred for 15 min then quenched with a small amount of ascorbic acid. The solution was stripped to min volume and precipitated with ether. The precipitate was purified by reversed phased HPLC on a C18 column using an ACN/water/0.1% TFA gradient.

Dimerization Reaction:

The pure oxidized monomer (80 mg, 34 micromoles) was dissolved in 1 mL of DMF. To this was added 10 eq. of DIEA (59 microliters) followed by 0.5 eq. of the activated tetrafunctional linker of Example 9 (12.6 mg, 17 micromoles) in 5 mg aliquots over 2 hours. The dimerization was followed by HPLC. When reaction was complete, the solution was diluted with 80/20 water/ACN and purified by reversed phase HPLC. The pure fractions were treated with TFA to remove Boc protection (reaction monitored by HPLC). The free diamine was purified by reversed phase HPLC on a C18 column using an ACN/water/0.1% TFA gradient.

PEGylation Reaction:

Dimer peptide (20 mg, 4 micromoles) along with 175 mg (2.2 eq., 8.8 micromoles) mPEG-NPC 20 kDa from NOF Corp. were dissolved in 0.5 mL of 70/30 DMSO/ACN. To this viscous solution was added 7 microliters of DIEA (10 eq., 40 micromoles). The reaction was followed by HPLC. After 16 hours, another 0.5 mL of 70/30 DMSO/ACN was added to the reaction mixture. The reaction was complete at 22 h. The solution was diluted with 80/20 water/ACN containing 0.2% AcOH. One third of the solution was loaded onto a column containing strong cation exchange Source 15S (from GE Biosciences) and multiple column volumes of solvent A (35% ACN/water containing 0.2% AcOH) were passed through the column. The PEGylated material was eluted from the column with 100 mM $NH_4OAc$ in solvent A. The fractions containing the desired product were freeze-dried on a lyophilizer. Fractions of purity >95% were dissolved in 80/20 ACN/water, combined, and freeze-dried on a lyophilizer to give 42 mg of PEGylated peptide as a white solid.

Example 11

C-Terminus Dimerization of a Peptide and Subsequent PEGylation Using a Tetrafunctional Linker The following conjugate (Compound V) was prepared according to procedures of Example 10, except that a different peptide monomer was used (using the sequence Ac-GGLYACHYGPIT(Nal)VCQPLR(MeG)K, SEQ ID NO: 23).

(Compound V)

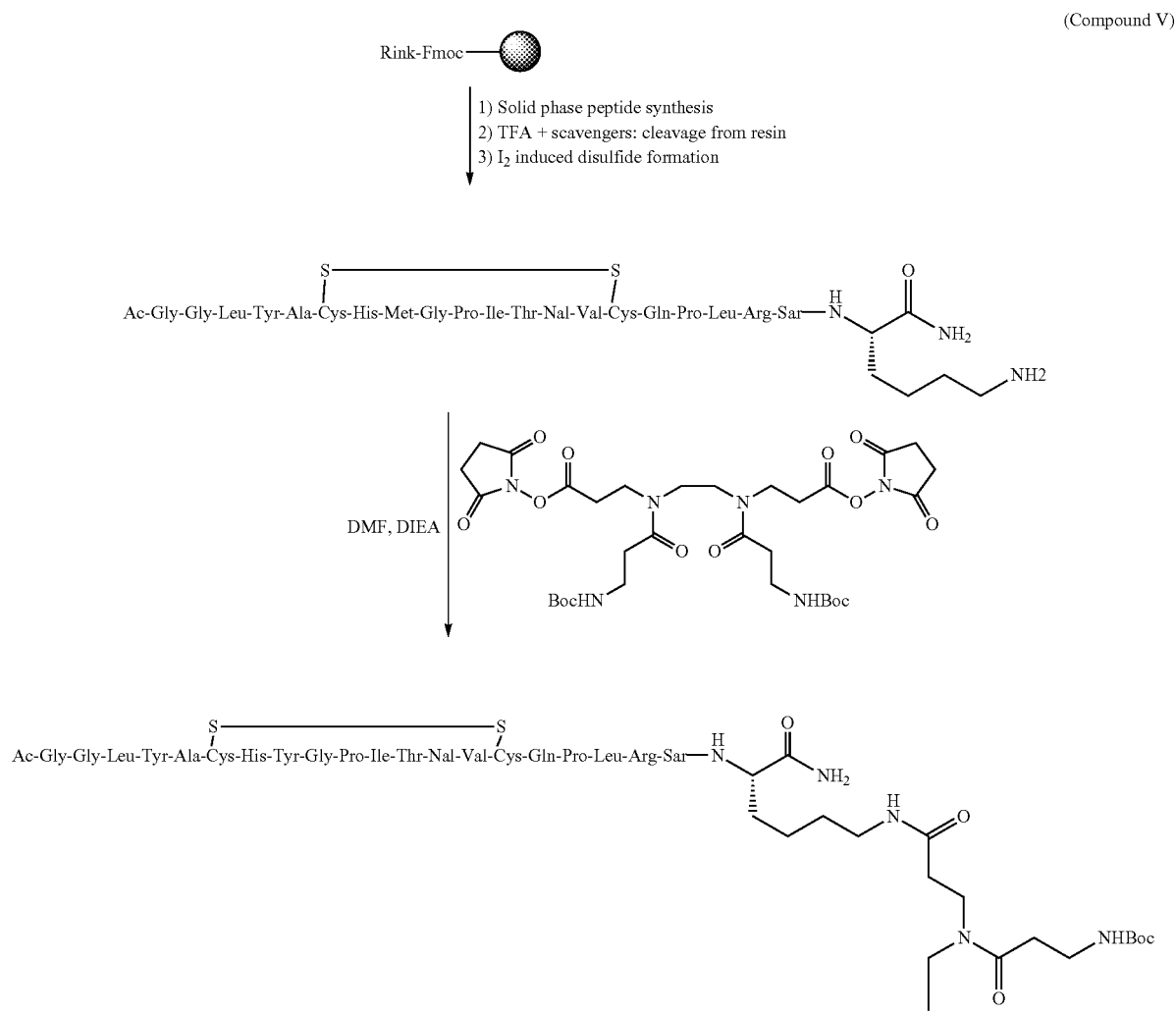

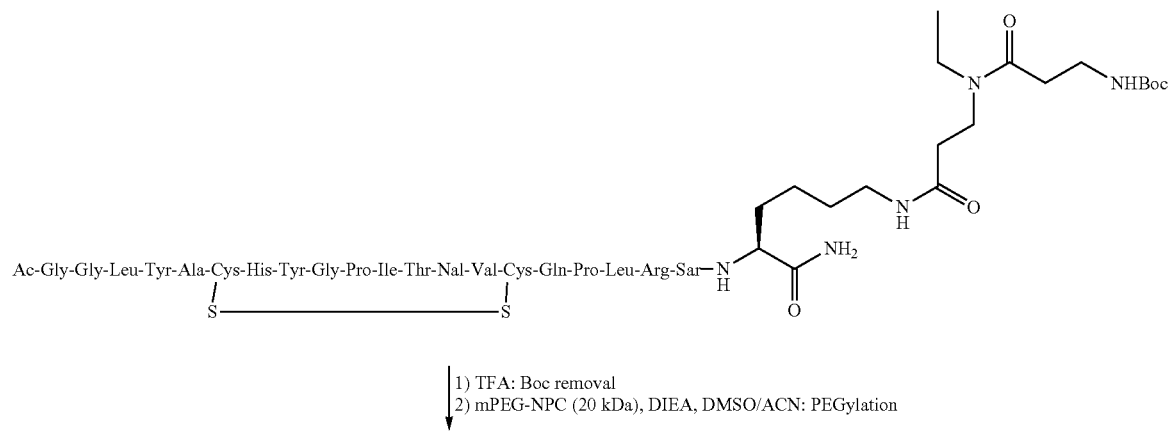
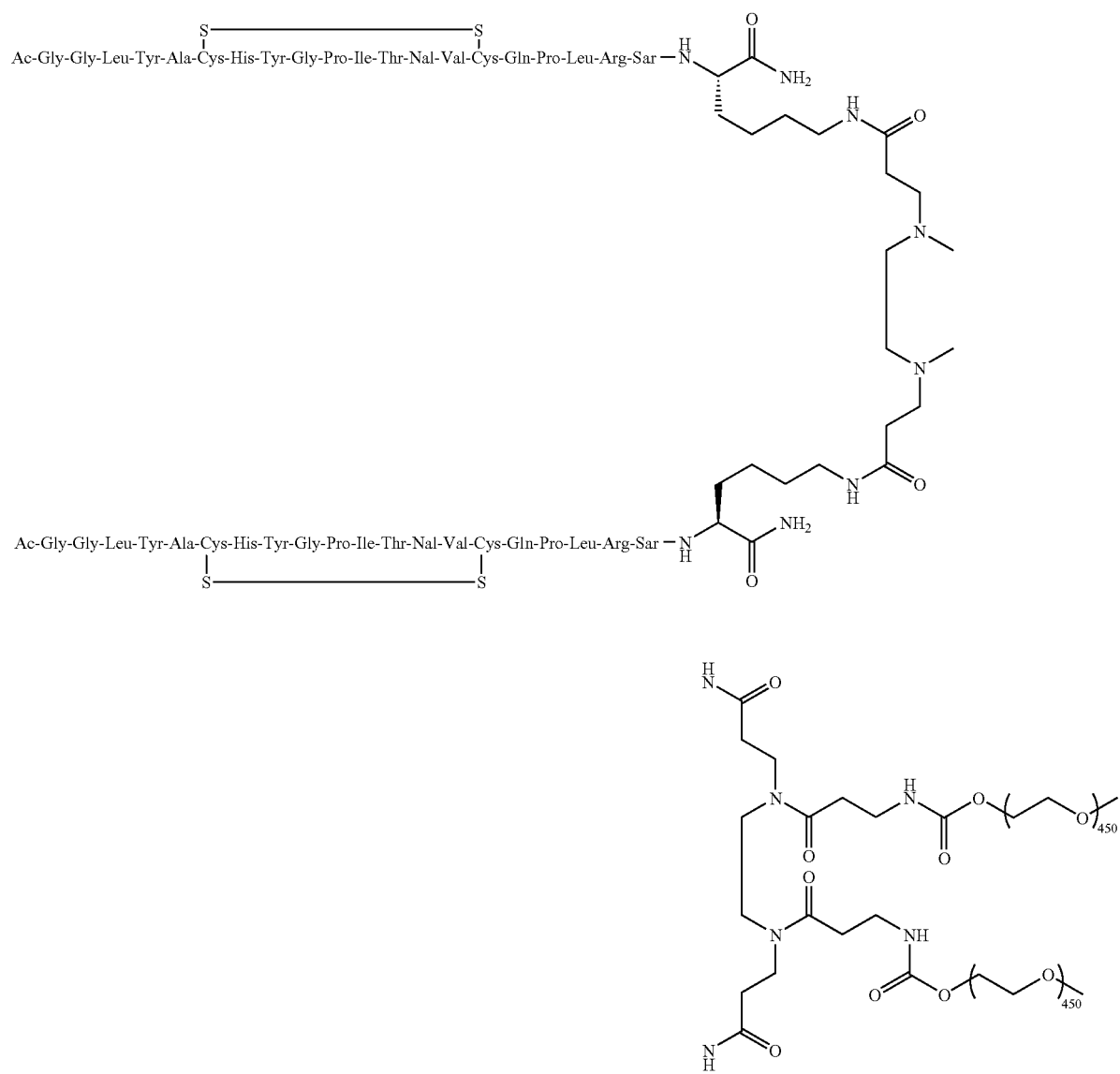

Example 12
C-Terminus Dimerization of a Peptide Using a Tetrafunctional Linker
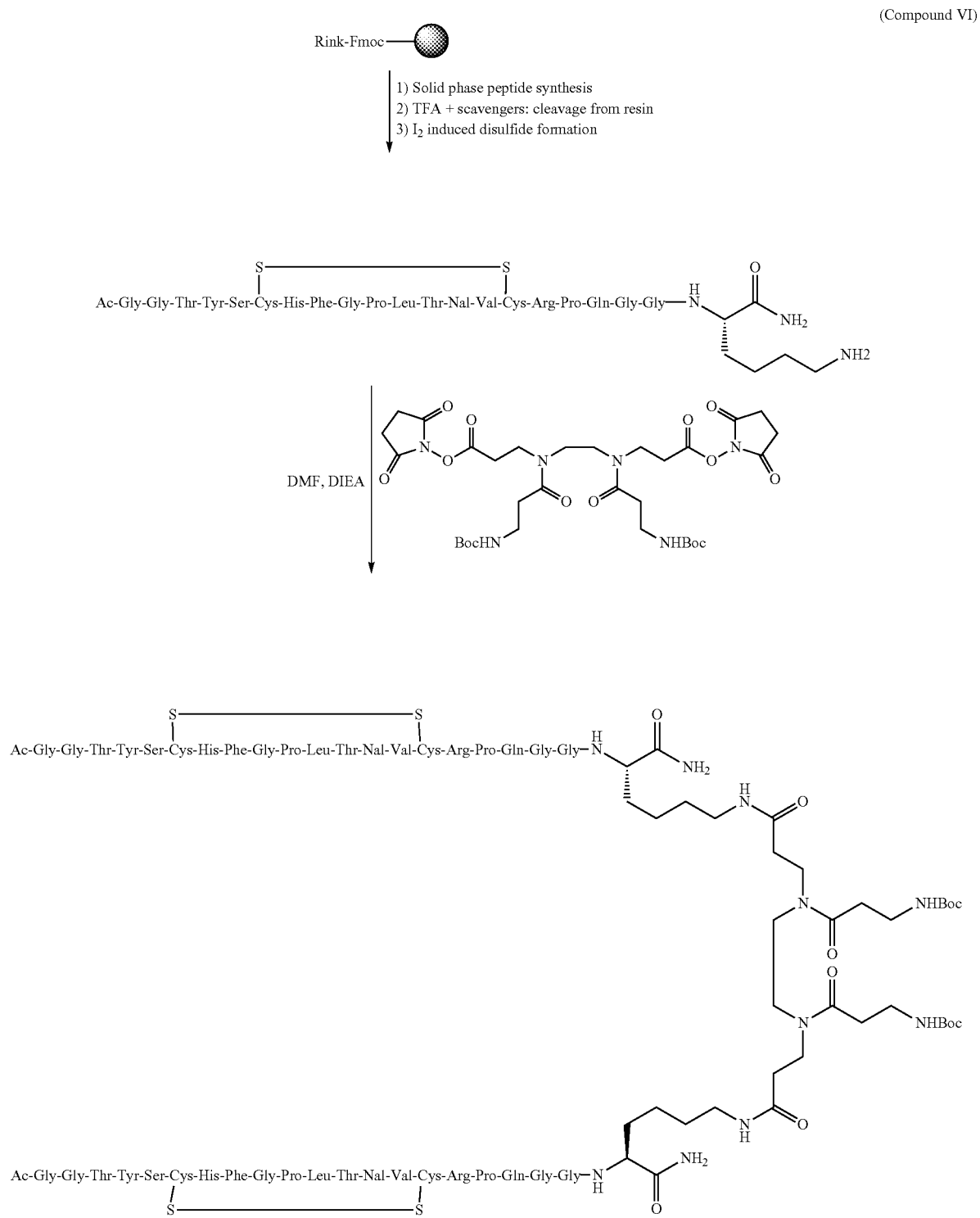
(Compound VI)
Following the peptide synthesis and dimerization procedures of Example 10, the above conjugate (Compound VI, using SEQ ID NO: 17 as starting material) was prepared as 6.0 mg of white solid.

Example 13
C-Terminus Dimerization of a Peptide Using a Tetrafunctional Linker
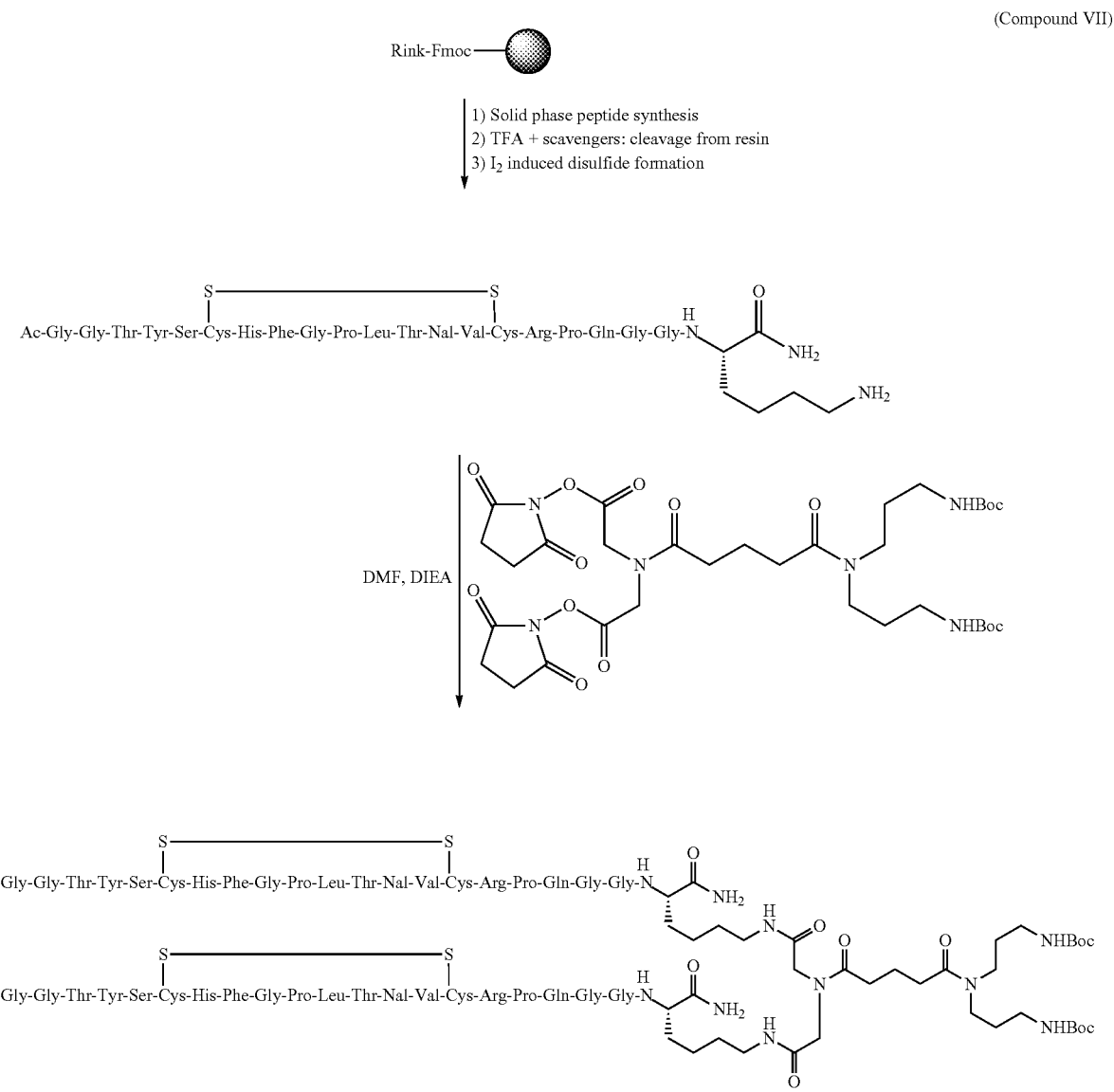
(Compound VII)
Following the peptide synthesis and dimerization procedures of Example 10, Compound VII (using the peptide of SEQ ID NO: 17 as starting material) was prepared as 4.5 mg of white solid.
Example 14
C-Terminus Dimerization of a Peptide Using a Trifunctional Linker
Compound (VIII)

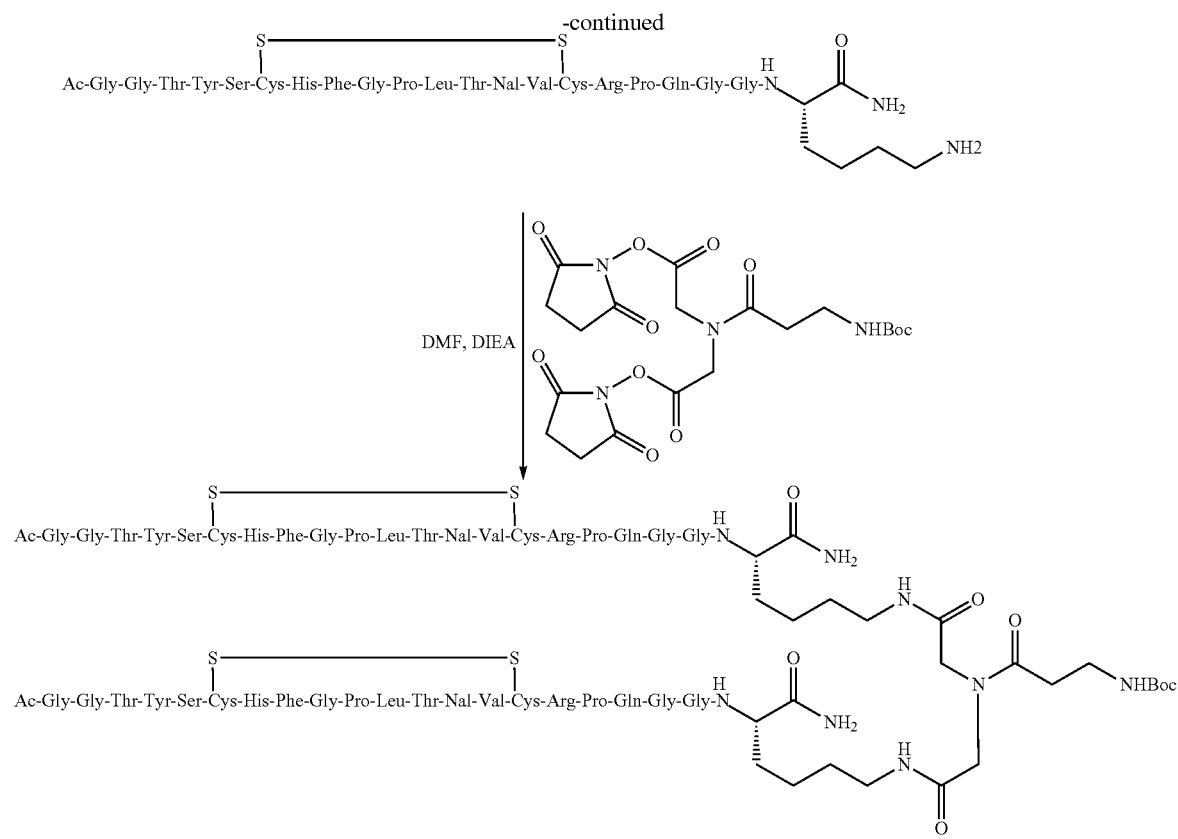
Following the peptide synthesis and dimerization procedures of Example 10, the Compound VIII (using the peptide of SEQ ID NO: 17 as starting material) was prepared as 5 mg of white solid.
Example 15
C-Terminus Dimerization of a Peptide Using a Trifunctional Linker
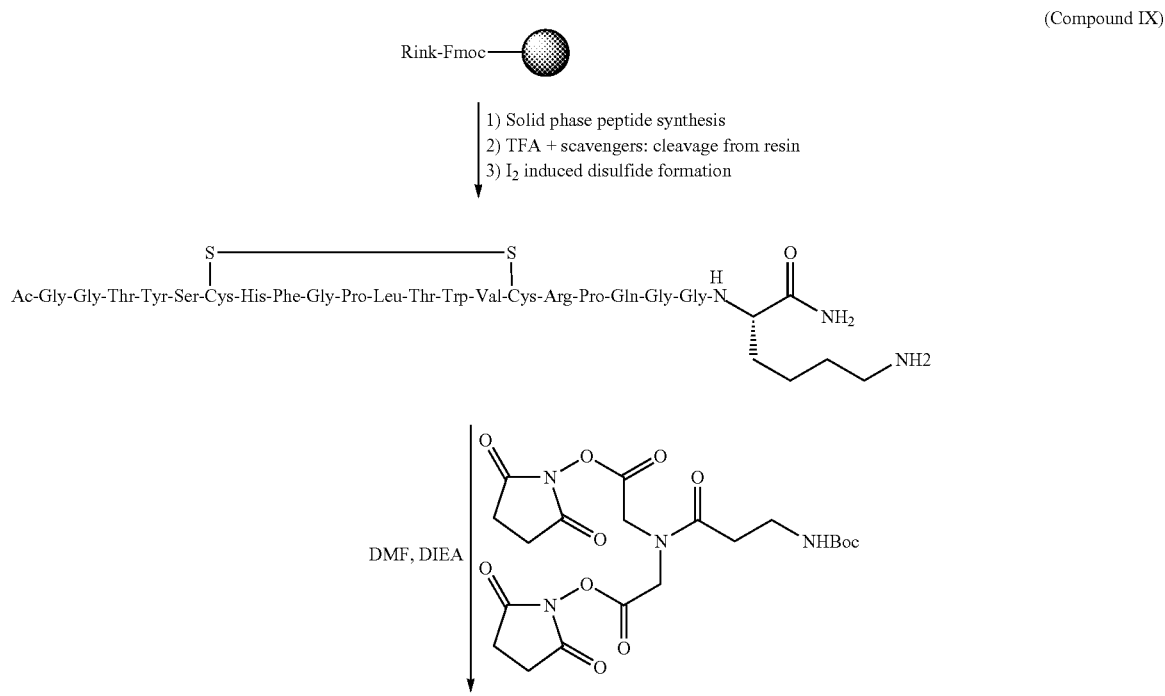
(Compound IX)

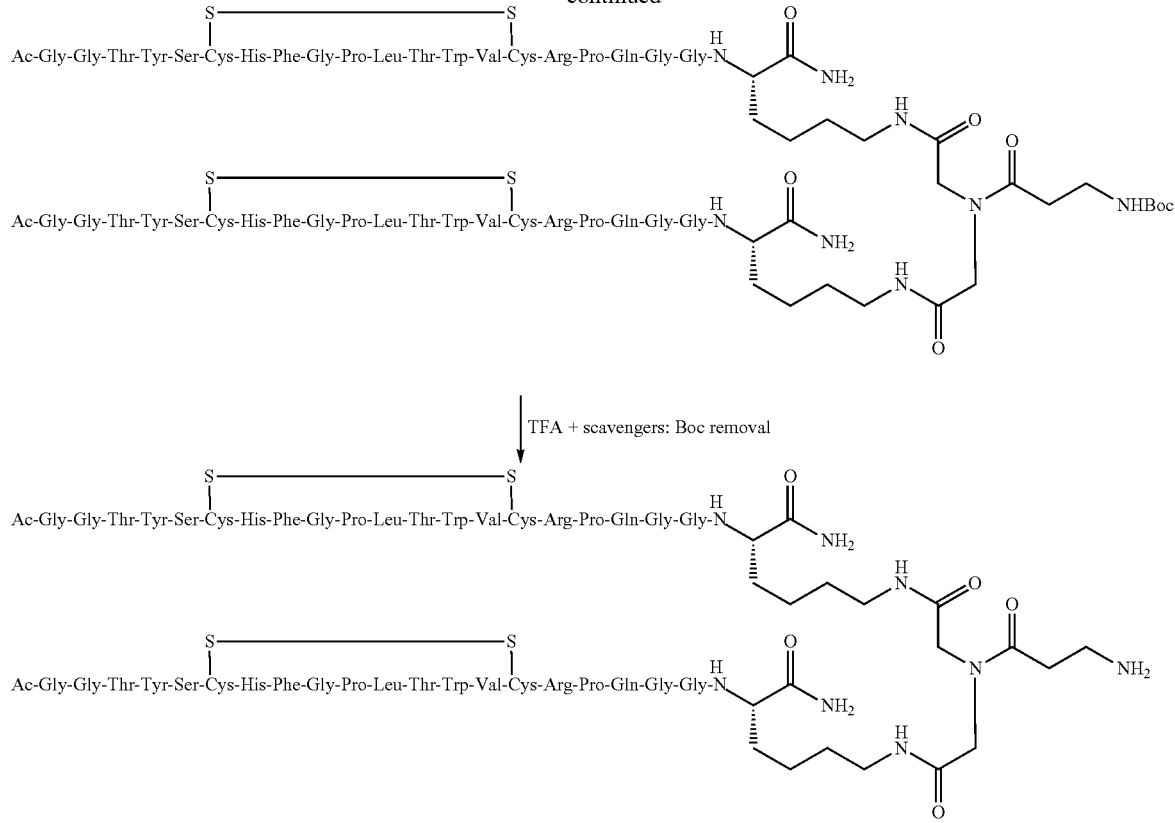
Following the peptide synthesis and dimerization procedures of Example 10, Compound IX (using the peptide of SEQ ID NO: 24 as starting material) was prepared as 95 mg of white solid.
Example 16
N-Terminus Dimerization of a Peptide Using a Trifunctional Amine Linker and Subsequent PEGylation with 5 kDa PEG
(Compound X)
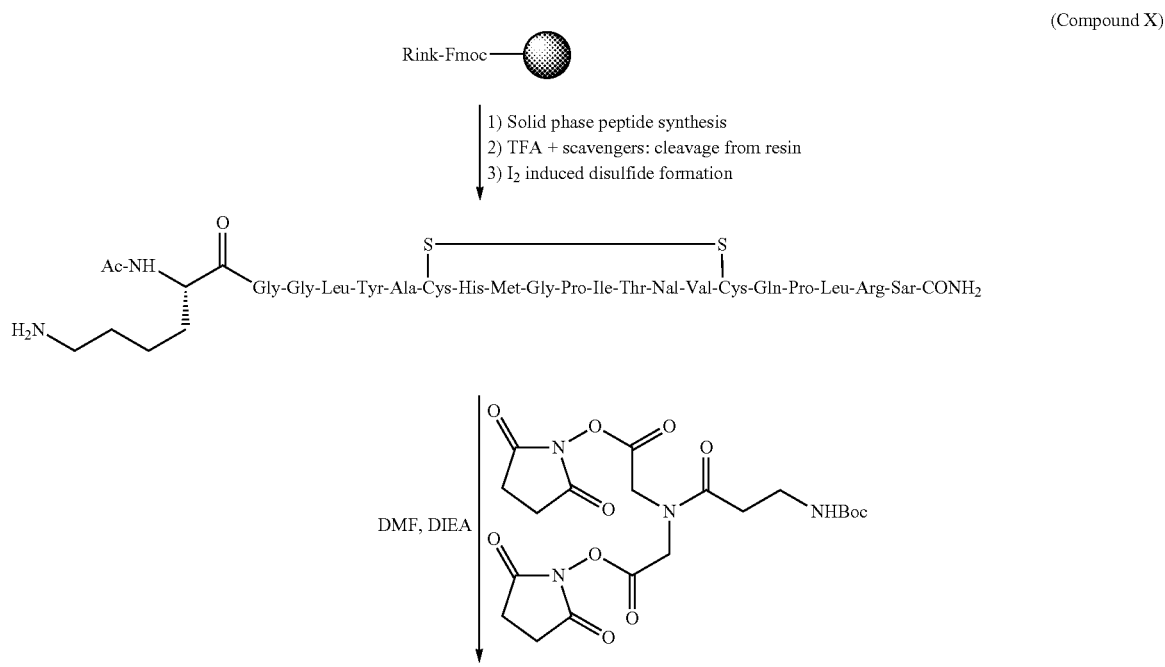

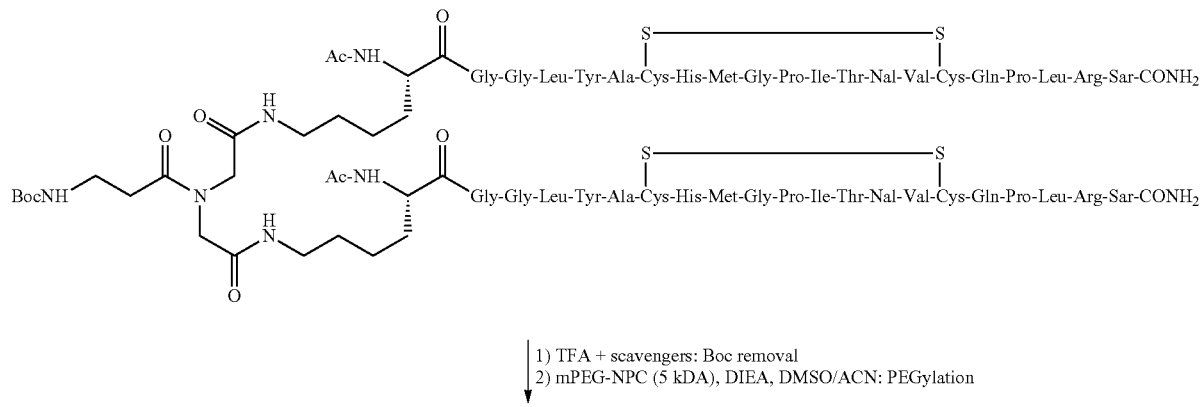

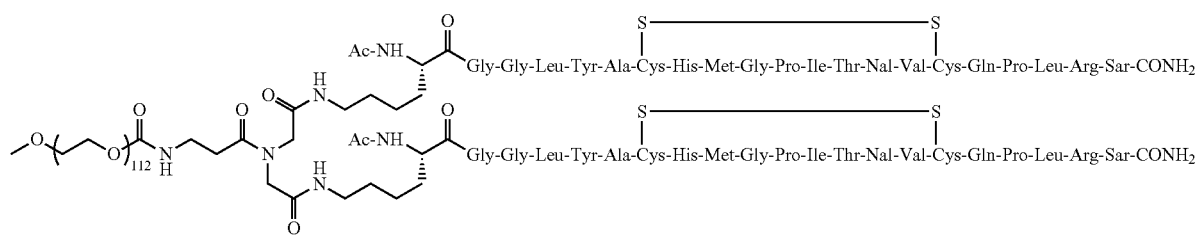

Peptide Synthesis:

The linear peptide Ac-K-G-G-L-Y-A-C-H-M-G-P-I-T-1Nal-V-C-Q-P-L-R-Sar-amide (7-15 disulfide, SEQ ID NO: 25), was prepared using standard Fmoc amino acids as in Example 3. Cleavage of the peptide from the resin was performed with a 85/10/2.5/2.5 mixture of TFA/triisopropyl silane/thioanisole/water and the resultant peptide was precipitated from cold ether. Purification on C18 using an ACN/water/TFA gradient afforded the pure monomeric peptide.

Dimerization Reaction:

Dimerization was performed as in Example 3 with 507 mg of monomer, 60 mg of trifunctional linker of Example 2, and 170 microliters of DIEA in 10 mL of DMF. An additional 6 mg of linker from Example 2 in 1 mL of DMF was added after 3 h. After an additional 1 h, 200 microliters of water were added, and the reaction mixture was freeze-dried on a lyophilizer. The crude peptide was purified by reversed phase HPLC on a C18 column using an ACN/water/TFA gradient to afford 236 mg of dimeric peptide as a white solid. The dry solid was taken up in 4 mL of 95% TFA/water, agitated for 15 in, and was then added to cold ether to precipitate the peptide. The solid was dissolved in 50% ACN/water and was freeze-dried on a lyophilizer to afford 197 mg of dimeric peptide as a white solid.

PEGylation Reaction:

The dimeric peptide from above (102 mg) was taken up in 3.5 mL of DMSO, DIEA (34 microliters) was added, followed by a solution of mPEG-NPC 5 kDA (from Sun Bio USA, Orinda, Calif., catalog number P1NPC-005) in 1.5 mL of CAN. After stirring for 2 h, HOAc was added drop wise until the solution became clear (~10 drops). The solution was diluted to 10 mL with 35% ACN/water containing 0.2% AcOH and was purified by cation exchange chromatography on Source 15S support as Example 3 to give 93 mg of what solid. The powder (Compound X) was analyzed by HPLC (Zorbax 300 SB-C8, ACN/water/TFA gradient) to reveal 98.8% purity. Peptide content (94%) was determined by combustion analysis based on observed nitrogen value of 7.83% compared to the predicted value of 8.33%.

Example 17

C-Terminus Dimerization of a Peptide and Subsequent PEGylation Using a Tetrafunctional Linker (Compound XI)

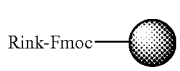 Rink-Fmoc

1) Solid phase peptide synthesis
2) TFA + scavengers: cleavage from resin
3) I₂ induced disulfide formation

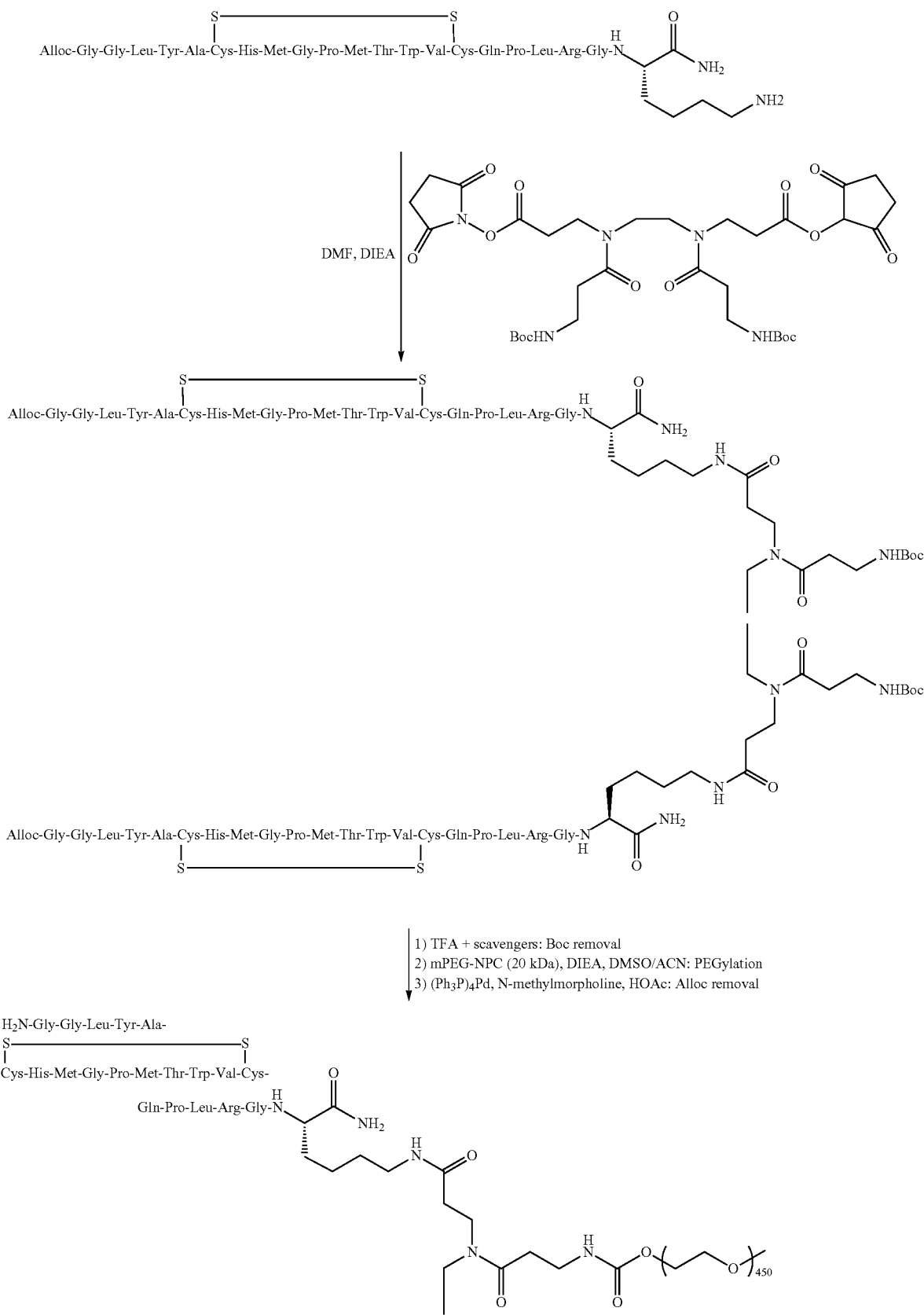

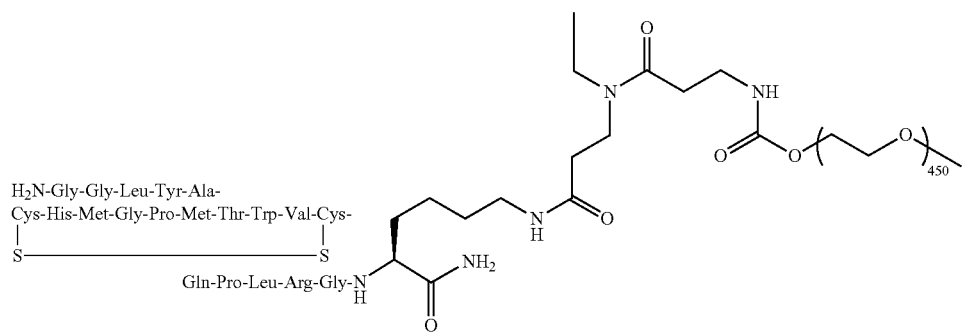

Following the peptide synthesis, dimerization, and PEGylation procedures of Example 10, the above conjugate (Compound XI, using SEQ ID NO: 26 as starting material) can be prepared. Glycine at position 1 uses an orthogonal N-terminus protecting group such as allyloxycarbonyl (Alloc). Post cleavage and dimerization, the Alloc group is removed with $(Ph_3)_4Pd$ with HOAc and N-methylmorpholine.

Example 18

C-Terminus Dimerization of a Peptide and Subsequent PEGylation Using a Tetrafunctional Linker (Compound XII)

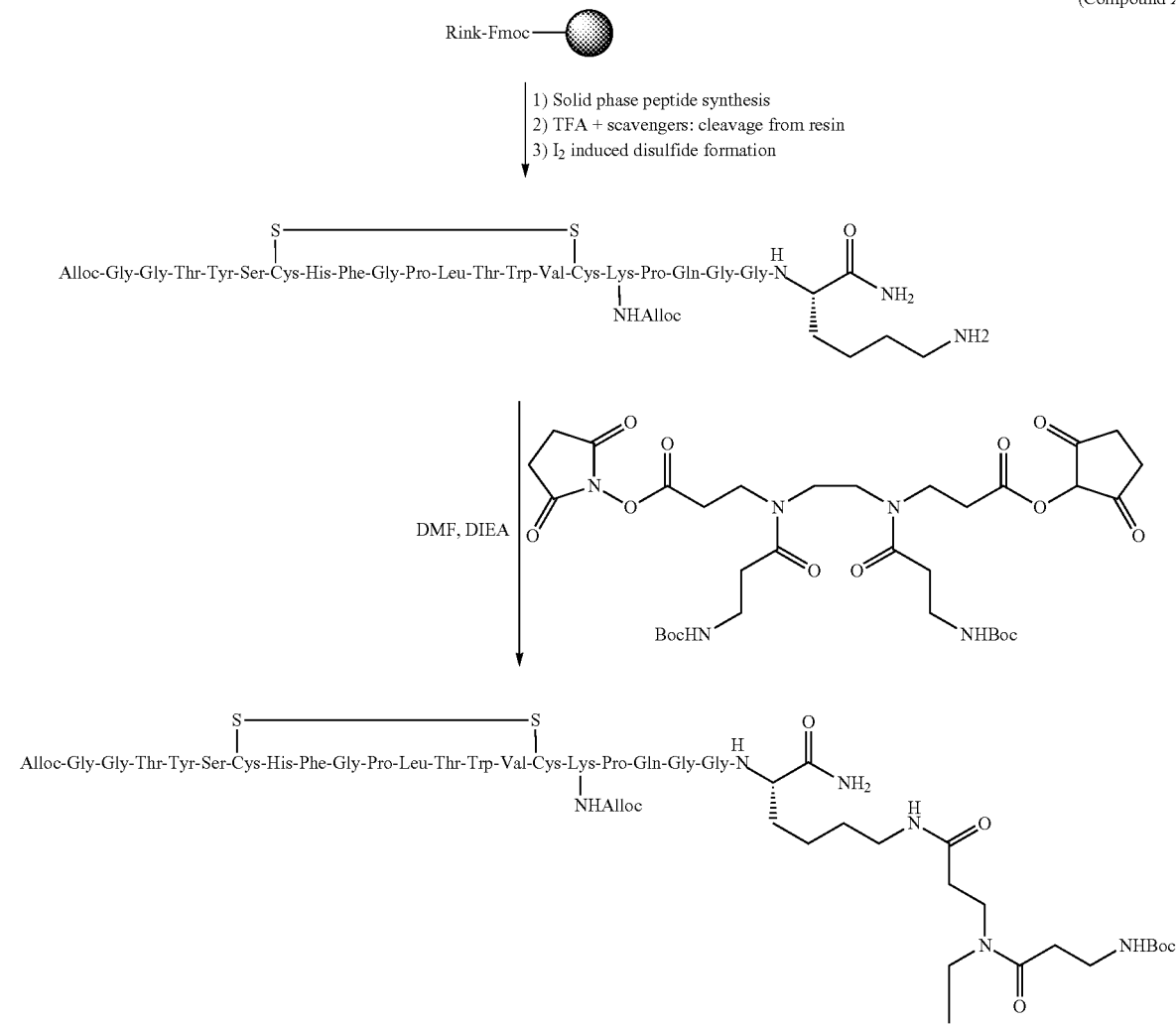

-continued

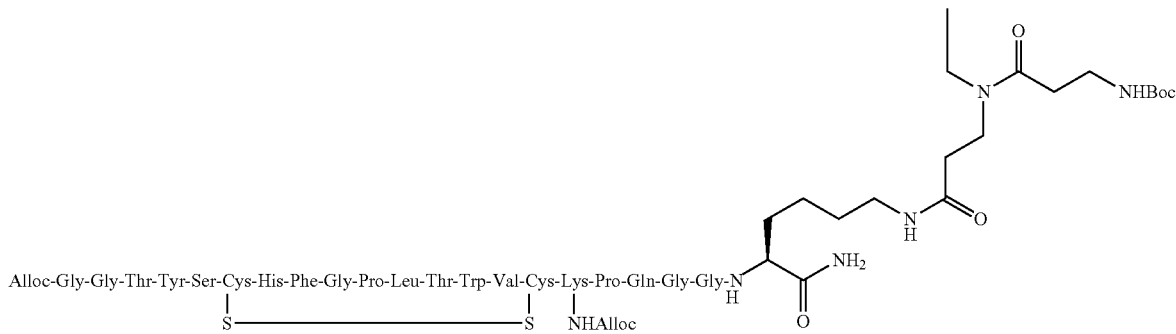

Alloc-Gly-Gly-Thr-Tyr-Ser-Cys-His-Phe-Gly-Pro-Leu-Thr-Trp-Val-Cys-Lys-Pro-Gln-Gly-Gly-N
|_____S——————————————S_____|  NHAlloc 1) TFA + scavengers: Boc removal
2) mPEG-NPC (20 kDa), DIEA, DMSO/ACN: PEGylation
3) (Ph₃P)₄Pd, N-methylmorpholine, HOAc: Alloc removal

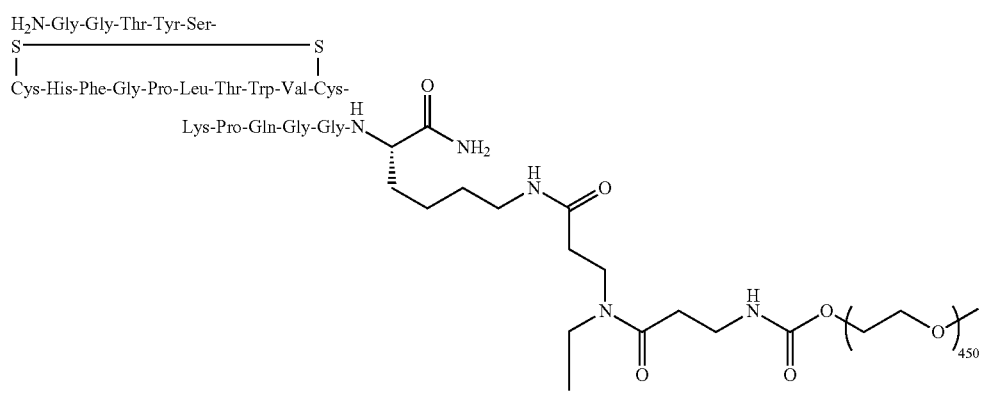

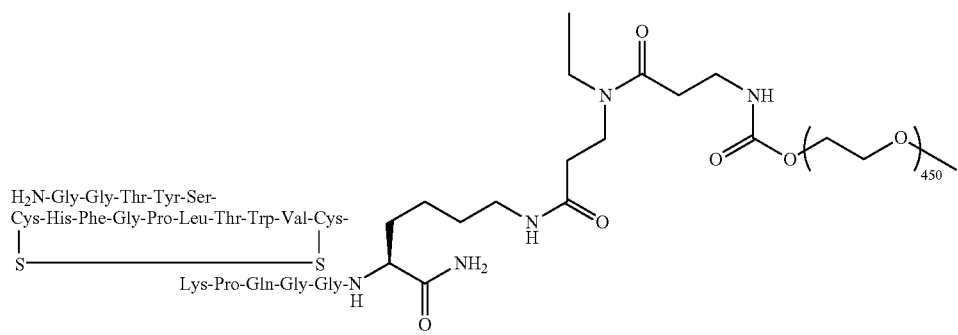

Following the procedure of Example 10, the above conjugate (Compound XII, using SEQ ID NO: 27 as starting material) can be prepared. Lysine at position 16 uses an orthogonal side chain protecting group such as allyloxycarbonyl (Alloc) and glycine at position 1 uses Alloc-Gly-OH. Post cleavage and dimerization, the two Alloc groups are removed with (Ph₃)₄Pd with HOAc and N-methylmorpholine Example 19

C-Terminus Dimerization of a Peptide and Subsequent PEGylation Using a Tetrafunctional Linker The following conjugate (Compound XIII) was prepared according to Example 10 (using SEQ ID NO: 5), except that mPEG-NPC 30 kDa (from NOF Corp, Japan) was used instead of mPEG-NPC 20 kDa.

(Compound XIII)

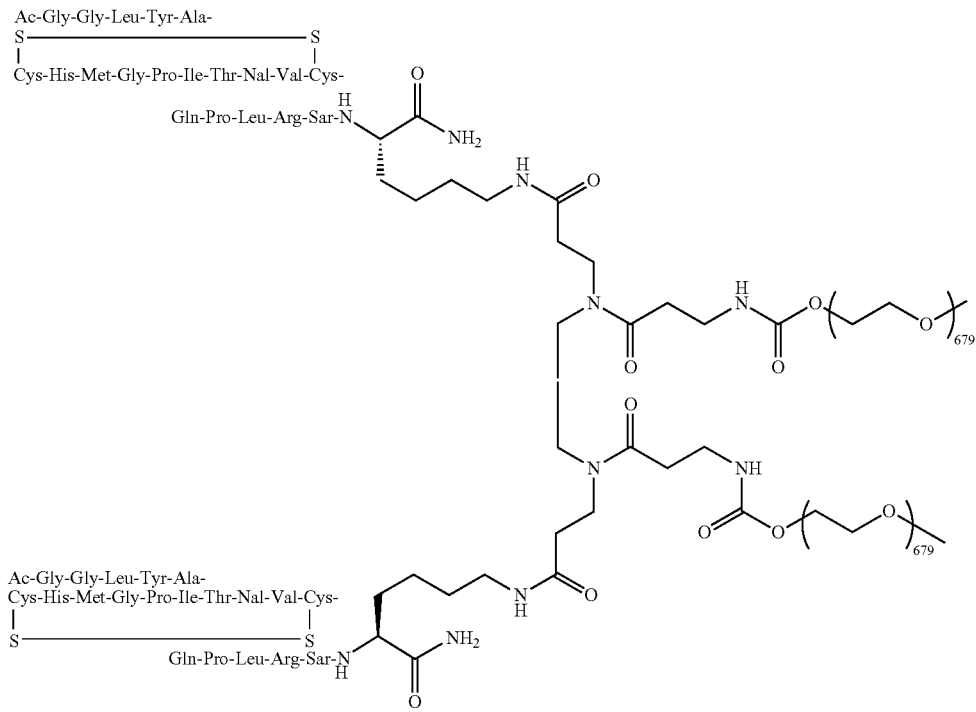

Example 20

Synthesis of Tetrafunctional Linker and Activation as the bis-NHS Ester

The tetrafunctional, activated, linker having the structure:

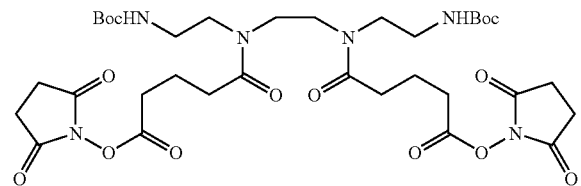

was synthesized according to following reaction scheme:

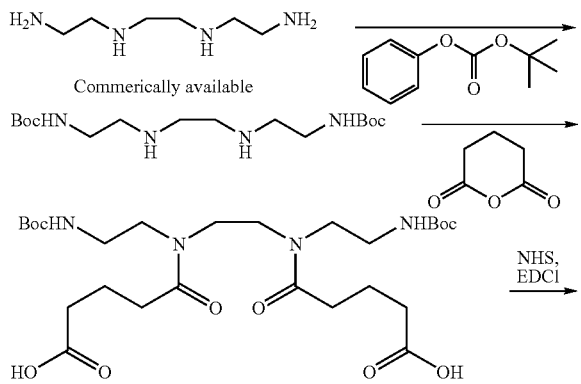

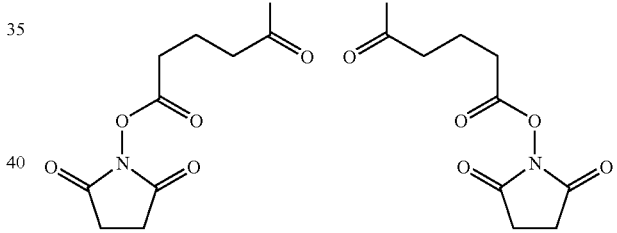

To a solution of the tetra-amine in DMF containing 2.2 eq. of t-butyl-phenyl carbonate was added catalytic triethylamine. The reaction mixture was stirred overnight. The reaction mixture was poured into phosphate buffer (2 L, 0.025 M K$_2$HPO$_4$ and 0.025 M NaH$_2$PO$_4$), and the resulted solution was adjusted to pH ~3 with 2 M H$_2$SO$_4$ with vigorous stirring. The mixture was washed with ether (washings discarded) and the aqueous layer was basified to pH 10 with 9 N NaOH; and then was extracted with DCM. The organic extracts were dried over Na$_2$SO$_4$, concentrated under reduced pressure, and then dried under vacuum overnight to give the desired product.

A mixture of diBoc tetra-amine (1 eq.) and glutaric anhydride (2 eq.) in anhydrous DCM (25 mL) was cooled to 5° C. (ice-water bath). Anhydrous TEA (1.3 eq.) was added and the mixture was stirred at room temperature for 6 hours. The mixture was diluted with more DCM and washed with 1 N NaHCO$_3$. The organic layer was discarded. The water layer was acidified to pH 3.0 with 2 NHC and extracted with ethyl acetate. The ethyl acetate layer was washed with water and brine, dried over sodium sulphate, and concentrated under reduced pressure to afford the tetrafunctional linker.

A mixture of the tetrafunctional linker (1 eq.) and N-hydroxysuccinimide (2.2 eq.) in anhydrous DMF was cooled to 4° C. in an ice-bath. N-(3-dimethylaminopropyl)-N'-ethylcarbodiimide hydrochloride (EDCI) (1.1 eq.) was added in portions to the reaction mixture. The resulting mixture was then warmed to room temperature and stirred for 2 hours. After removal of solvent under reduced pressure, the residue was partitioned between DCM and water. The extracts were dried over Na$_2$SO$_4$, concentrated, and dried under vacuum to give the final activated tetrafunctional linker as an off-white solid.

Example 21

Synthesis of Tetrafunctional Linker

The tetrafunctional linkers having the structure:

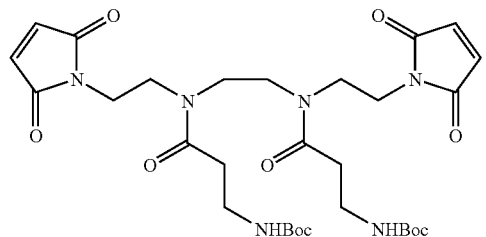

can be synthesized according to following reaction scheme:

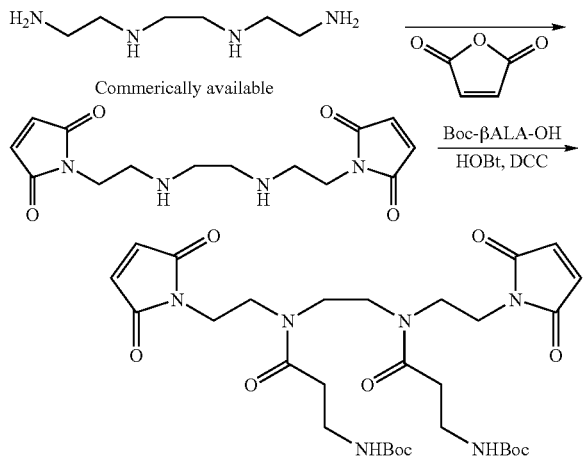

Example 22

Synthesis of a Trifunctional Linker and Dimerization and PEGylation of a Peptide The trifunctional linker having the structure:

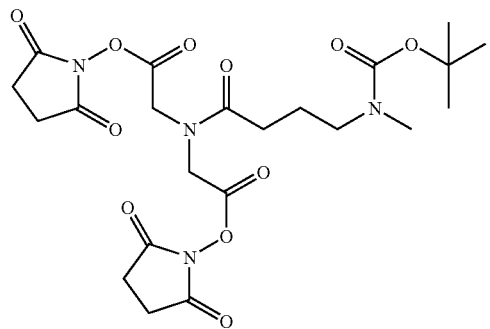

was made according to the following protocol.

Step I

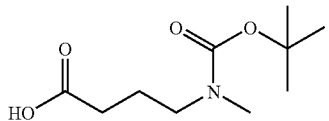

Di-t-butyl dicarbonate (7 g, 32.1 mmol) was added dropwise over 10 minutes to a mixture of 4-(methylamino)butyric acid hydrochloride (5 g, 32.5 mmole) in MeOH (50 mL) and 3 eq. Et$_3$N (5 mL). The reaction mixture was stirred at room temperature for 1 hour and then concentrated under reduced pressure. The residue was dissolved in EtOAc (150 mL), and washed with an ice-cold 0.1 N aqueous HCl solution (2×70 mL). The organic layer was then washed with water (2×100 mL) to neutral pH, and then washed with sat. NaCl (1×100 mL). The EtOAc layer was dried over Na$_2$SO$_4$ and concentrated to give the Boc-protected product (6.8 g, 96% yield).

Step II

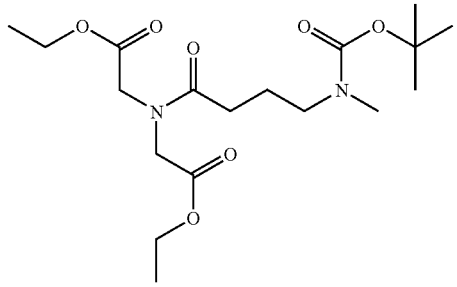

A mixture of the Boc-protected 4-(methylamino)butyric acid (6.8 g, 31.3 mmol) and di-ethyl iminodiacetate (5.92 g, 29.7 mmol) in anhydrous DCM (80 mL) was cooled to 4° C. in an ice-bath. EDCI (7.1 g, 37.3 mmol) was added in portions to the reaction mixture. The resulting mixture was then warmed to room temperature and stirred for 4 hours. After removal of solvent nder reduced pressure, the residue was partitioned between ethyl acetate (200 mL) and water (100 mL). The organic layer was subsequently washed with H$_2$O (4×100 mL), ice-cold 0.1 N HCl (2×100 mL), H$_2$O (2×100 mL), sat. NaHCO$_3$ (1×100 mL), H$_2$O (2×100 mL), and finally followed by sat. NaCl (1×100 mL). The organic layer was dried over Na$_2$SO$_4$ and then concentrated to give the desired product (10 g, 86.7% yield).

Step III

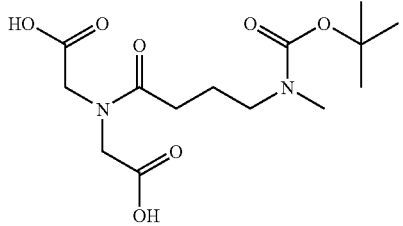

The diethyl ester product (10 g, 25.7 mmol) was hydrolyzed with 2N aq. LiOH in THF (1:1 by volume) for 18 hours. After removal of solvent, the aqueous layer was washed with EtOAc (2×100 mL) and the organic layer was discarded. The aqueous layer was acidified with 6 N HCl to pH ~1 at 0° C.

with ice added in the solution, and then saturated with solid NaCl afterwards. The saturated solution was extracted with EtOAc (5×100 mL). The combined extracts were washed with sat. NaCl (3×100 mL), dried over Na₂SO₄, and then concentrated to yield the di-acid linker (5.8 g, 68%) as a white solid.

Step IV

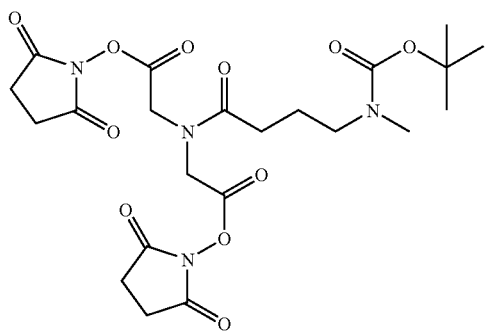

A mixture of above di-acid linker (1 g, 3.0 mmol) and N-hydroxysuccinimide (760 mg, 6.6 mmol) in anhydrous DCM (20 mL) was cooled to 4° C. in an ice-bath. N-(3-dimethylaminopropyl)-N'-ethylcarbodiimide hydrochloride (EDCI) (1.72 g, 9.0 mmole) was added in portions to the reaction mixture. The resulting mixture was then warmed to room temperature and stirred for 3 to 4 hours. After removal of solvent, the residue was partitioned between ethyl acetate and water. The aqueous layer was extracted with EtOAc (2×50 mL). The combined organic layer was washed with water (5×50 mL), and sat. NaCl (1×50 mL). The extracts were died over Na₂SO₄, concentrated, and dried under vacuum to give the final activated linker as a white solid (1.35 g, 85%).

Peptide Dimerization with Activated Linker:

Peptide monomer as described in Example 3 (SEQ ID NO: 5, 193 mg, 0.075 mmol) was dissolved in anhydrous DMSO (2 mL) with DIEA added (70 µL, 0.38 mmol) with stirring. The activated linker (21.7 mg, 0.041 mmol) was dissolved in 0.5 mL of anhydrous DMSO and then added by pipette. The resulting mixture was stirred at room temperature for 1 hour, and then analyzed by HPLC [Analytical HPLC column: Agilent Zorbax 300SB-C8, 5 micron, 300 Å, 2.1×150 mm (20% B to 70% B over 10 min; 0.1% TFA in ACN & H₂O as mobile phase; UV detector: 210 nm; flow rate: 0.5 mL/min)] and LC-MS. When the reaction is complete, the mixture was quenched with 20 µL of H₂O, and lyophilized to remove the solvent.

The dried residue was treated with TFA-DCM (1:1) (1 mL) for 10 minutes to remove the Boc-protecting group, and the solvent was dried by gently blowing N₂ gas over the solution. One half of the mixture was purified by preparative HPLC (25% B to 50% B over 70 min; 0.1% TFA in ACN & H₂O as mobile phase; UV detector: 210 nm; flow rate: 30 mL/min). After drying the fractions, the dimeric peptide was isolated as a white power (42 mg, 43% yield) in 95% purity.

PEGylation of Dimeric Peptide with 40 kDa PEG:

The dimeric peptide (42 mg, 0.008 mmol) was dissolved in anhydrous DMSO-ACN (3:1 by volume) (2 mL) with DIEA added (10 µL, 7 eq.). Activated 40 kDa (mPEG)₂-Lys-NHS (480 mg, 0.012 mmol, from Nektar Therapeutics, San Carlos, Calif.) dissolved in anhydrous acetonitrile (1 mL) was added, and the resulting mixture was stirred at room temperature overnight. Analysis by HPLC indicated that ⅓ of peptide dimer as starting material remained. Another portion of activated PEG ragent (480 mg, 0.012 mmol) dissolved in anhydrous acetonitrile (1 mL) was added and the reaction mixture was stirred again overnight. Analytical HPLC indicated the majority of product formed with small amount of starting material. After lyophilizing the solvent, the mixture was passed through an strong cation ion-exchange column as in Example 3 to remove the excess hydrolyzed PEG. The first peak by UV collected from ion-exchange purification was identified to be an 80 kDa-PEGylated product and confirmed by SEC analysis. The second peak by UV collected from ion-exchange purification was identified to be desired 40 kDa-PEGylated product (in 85% purity) along with some starting material and impurities. The impure mixture was re-purified by preparative HPLC (C18, ACN/H2O/0.1% TFA gradient) to yield the 40 kDa-PEGylated conjugate (Compound XIV, 32 mg) in 95% purity.

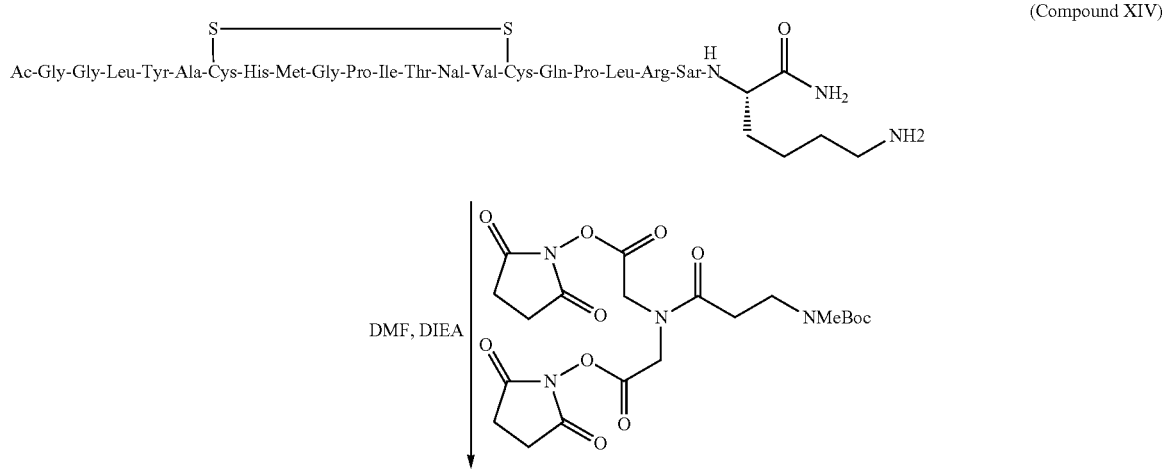

(Compound XIV)

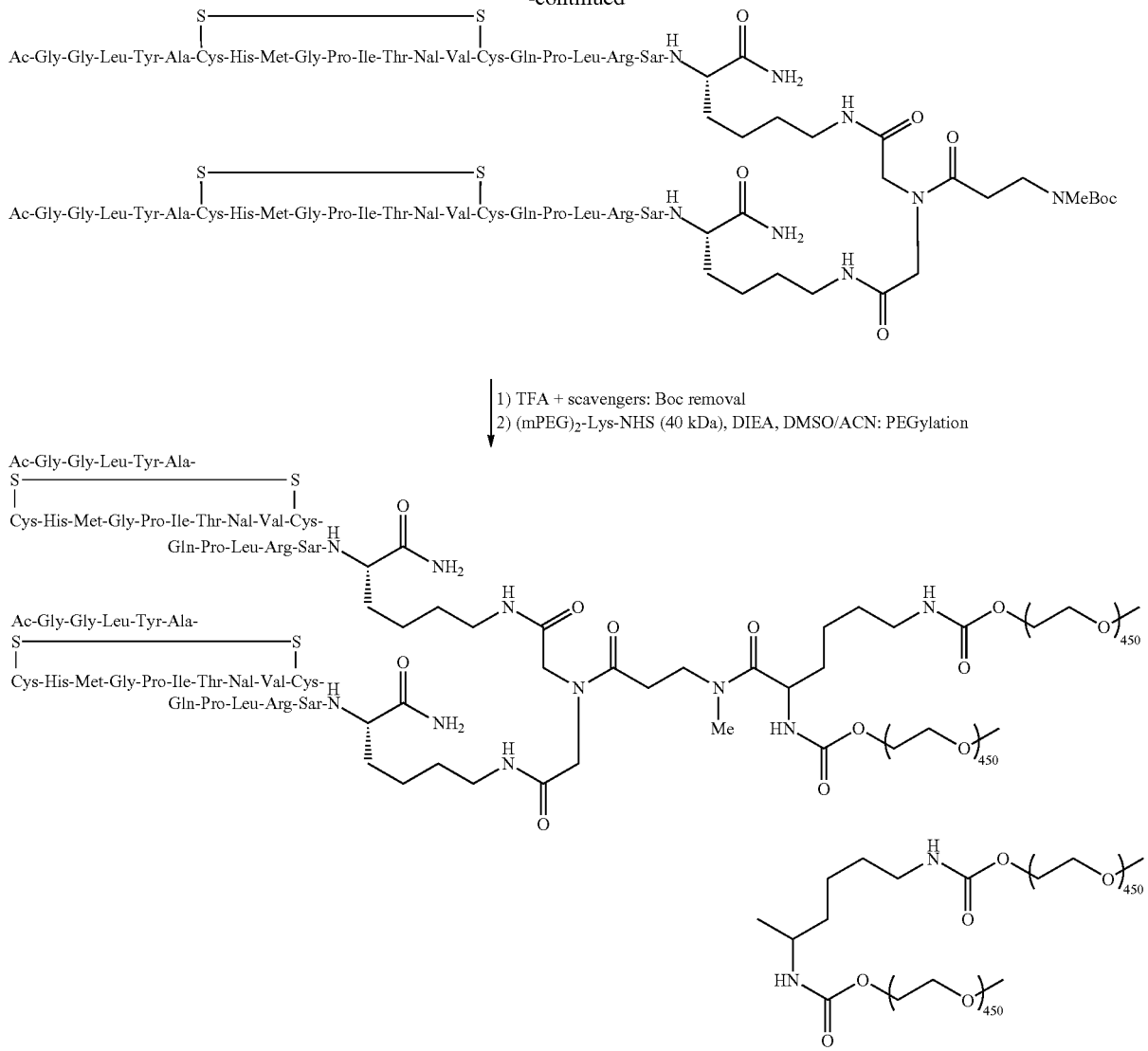

Example 23

C-Terminus Dimerization of a Peptide and Subsequent PEGylation Using a Tetrafunctional Linker Compound XV was prepared as follows.

Peptide Synthesis:

The monomeric peptide shown as SEQ ID NO: 16 was synthesized on 30 g of TentaGel Rink Amide resin using standard Fmoc-amino acids (TFA-labile side chain protecting groups) and diisopropylcarbodimide (DIC)/hydroxybenzotriazole (HOBt) couplings (0.25 M, 4 eq, 2 h couplings) on an ACT90 peptide synthesizer (from Advanced ChemTech, Louisville, Ky.). The resin was cleaved with 85/10/2.5/2.5 TFA/TIPS/Thioanisole/water. The peptide was precipitated from the solution by adding diethylether. The precipitate was collected, dried under reduced pressure, and taken up in trifluoroethanol (TFE) and diluted with MeOH (final ratio TFE:MeOH 1:4) to 2 mg/ml. To this stirring solution was added a saturated solution of $I_2$ in AcOH until the light yellow color remained. The solution was stirred for 15 min. then quenched with a small amount of ascorbic acid. The solution was stripped to minimum volume and precipitated with ether. The precipitate was purified by reversed phase HPLC on a C18 column using an water/0.12% TFA (solvent A) and ACN/0.10% TFA (solvent B) gradient as follows: 5% B for 5 min, to 20% B over 1 min, to 40% B over 55 min, to 95% B over 1 min. Fractions containing the desired peptide were combined and lyophilized to dryness to yield the pure monomeric peptide.

Dimerization Reaction:

The pure oxidized monomer (1156 mg, 498 micromoles) was dissolved in 11 mL of DMF. To this was added 10 eq. of DIEA (852 microliters) followed by 0.5 eq. of the activated tetrafunctional linker of Example 9 (184.6 mg, 249 micromoles) in aliquots over 1 h. The dimerization was followed by HPLC. When the reaction was complete, the solution was diluted with 80/20 water/ACN and purified by reversed phase HPLC. The pure fractions were treated with TFA to remove Boc protection (reaction monitored by HPLC). The free diamine was purified by reversed phase HPLC on a C18 column using an water/0.12% TFA (solvent A) and ACN/0.10% TFA (solvent B) gradient as follows: 10% B for 9 min, to 20% B over 1 min, to 35% B over 70 min, then to 80% B over 1 min. Fractions containing the desired peptide were combined and lyophilized to dryness to yield 619 mg of pure dimeric peptide.

PEGylation Reaction:

Dimer peptide (219 mg, 44.2 micromoles) along with 2917 mg (2.2 eq., 97.2 micromoles) mPEG-NPC 30 kDa from NOF Corp (lot # M35525) were dissolved in 20 mL of 70/30 DMSO/ACN. To this viscous solution was added 76 microliters of DIEA (10 eq., 442 micromoles). The reaction was followed by HPLC. The reaction was complete at 5.5 h. Cold ether was added to the reaction mixture to precipitate the peptide and the precipitate was washed with cold ether three times. The peptide was dissolved in 80/20 water/ACN containing 0.2% AcOH. One third of the solution was loaded onto a column containing strong cation exchange Source 15S (from GE Biosciences) and multiple column volumes of solvent A (35% ACN/water containing 0.2% AcOH) were passed through the column. The PEGylated material was eluted from the column with 100 mM NH$_4$OAc in solvent A. This process was repeated two more times with the rest of the peptide solution. The fractions containing the desired product were lyophilized to dryness. Fractions of purity >95% were dissolved in 80/20 ACN/water, combined, and lyophilized three additional times followed by purification by reversed phase HPLC on a C18 column using an water/0.2% HOAc (solvent A) and ACN/0.2% HOAc (solvent B) gradient as follows: 22% B at start, to 24% B over 10 min, to 30% B over 1 min, to 40% B over 60 min, then to 95% B over 1 min. Fractions containing the desired peptide were combined and lyophilized to dryness to yield 514 mg of pure PEGylated dimer as a white solid.

The synthesis of Compound XV is shown below.

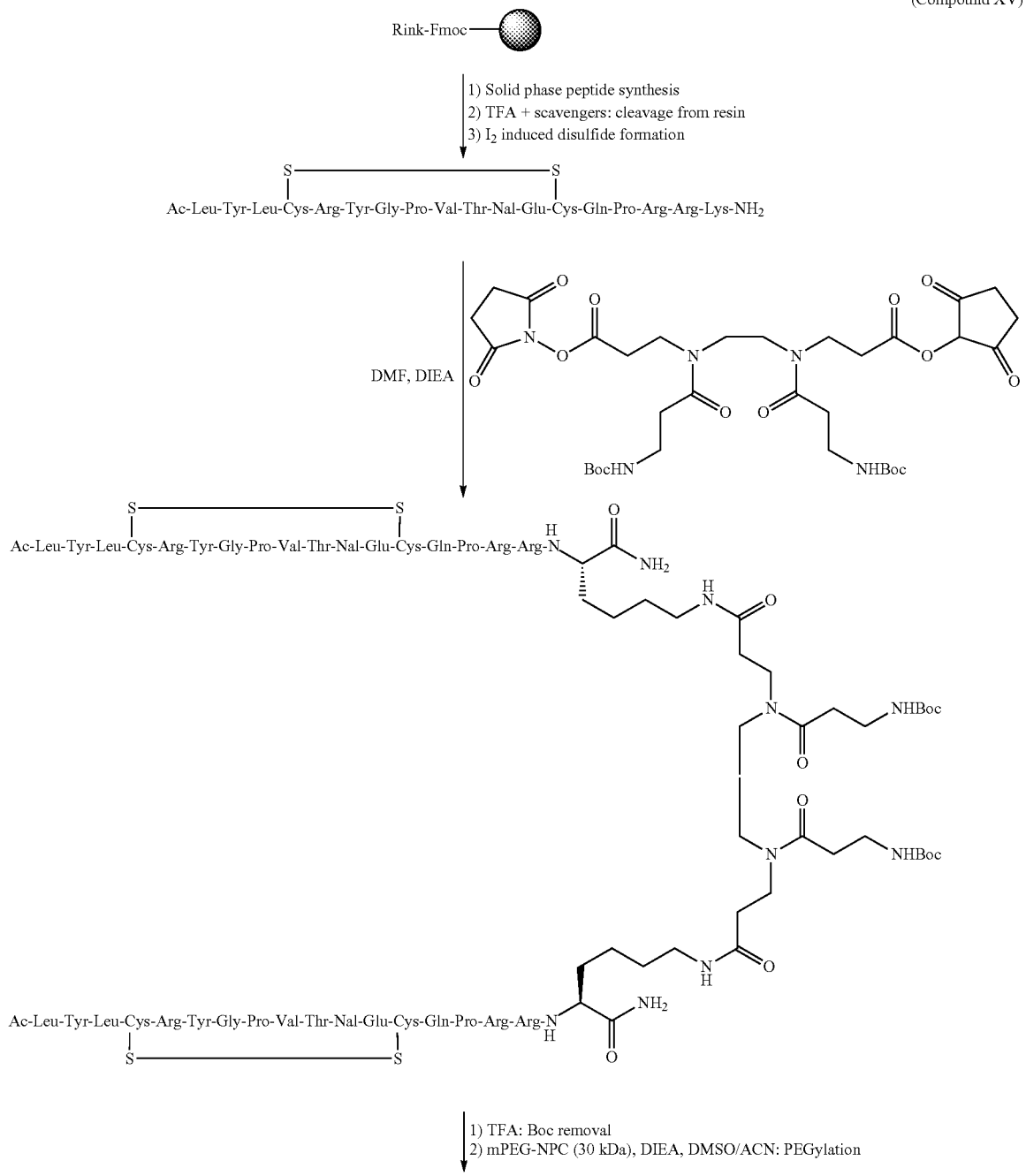

-continued
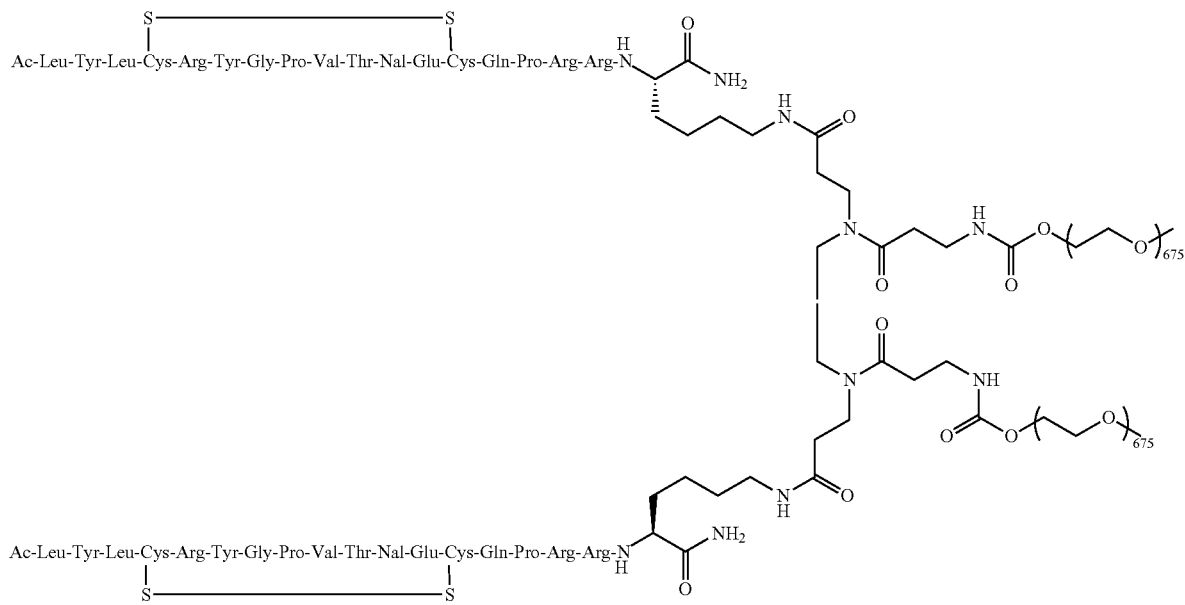
Example 24
PEGylation with 20 kDa PEG
The synthesis of Compound XVI, a conjugate with two 20 kDa PEG moities, is shown below.
(Compound XVI)
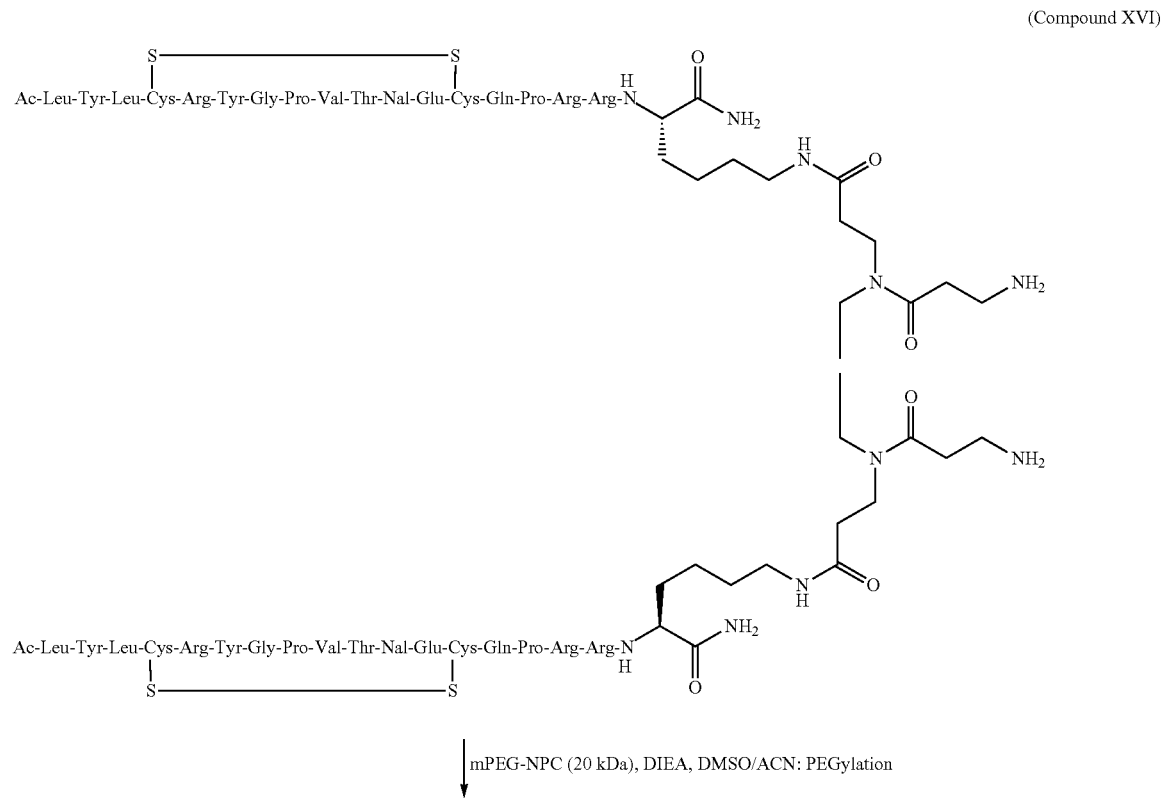
mPEG-NPC (20 kDa), DIEA, DMSO/ACN: PEGylation -continued

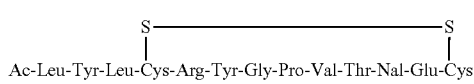
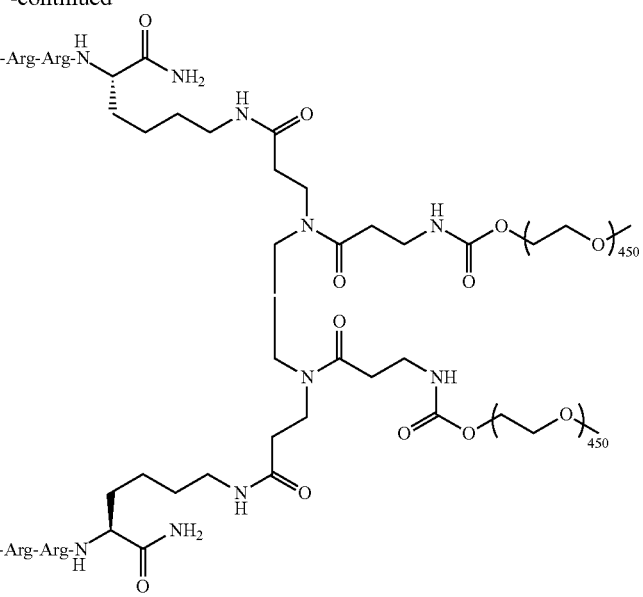
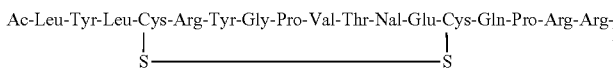

Dimer peptide (SEQ ID NO:16, 79 mg, 15.9 micromoles) from Example 23, above, along with 700 mg (2.2 eq., 34.9 micromoles) mPEG-NPC 20 kDa from NOF Corp (MEMP-20T, lot # M4D558) were dissolved in 2.5 mL of 70/30 DMSO/ACN. To this viscous solution was added 28 microliters of DIEA (10 eq., 159 micromoles). The reaction was left overnight for completion. Cold ether was added to the reaction mixture to precipitate the peptide and the precipitate was washed with cold diethyl ether three times. The peptide was dissolved in 80/20 water/ACN containing 0.2% AcOH. Half of the solution was loaded onto a column containing strong cation exchange Source 15S (from GE Biosciences) and 2-3 column volumes of solvent. A (35% ACN/water containing 0.2% AcOH) were passed through the column. The PEGylated material was eluted from the column with 100 mM NH$_4$OAc in solvent A. The purification process was repeated with the remaining portion of the peptide solution. The fractions containing the desired product were freeze-dried on a lyophilizer. Fractions of the desired product with purity >95% were dissolved in 80/20 ACN/water, combined, and freeze-dried three additional times followed by purification by reversed phase HPLC on C18 column using a water/0.2% HOAc (solvent A) and ACN/0.2% HOAc (solvent B) gradient as follows: 22% B to 24% B over 10 min, to 30% B over 1 min. 30% to 40% B over 60 min, to 95% B over 1 min. The pure PEG-peptide conjugate was isolated as 470 mg of a white solid.

Example 25

Biological Testing of Peptides

1. Reporter Assay

This assay was based upon a murine pre-B-cell line transfected to express human EPO-R and further transfected with a fos promoter-driven luciferase reporter gene construct. Upon exposure to EPO or another EPO-R agonist, such cells respond by synthesizing luciferase. Luciferase causes the emission of light upon addition of its substrate luciferin. Thus, the level of EPO-R activation in such cells may be quantitated via measurement of luciferase activity.

The activity of a test peptide was measured by adding serial dilutions of the test peptide to cells, which were then incubated for 4 hr. After incubation, luciferin substrate was added to the cells, and light emission was measured. The concentration of test peptide that results in a half-maximal emission of light, relative to that observed with EPO, was recorded as the EC50.

2. Proliferation Assay

This assay was based upon a murine pre-B-cell line transfected to express human EPO-R. Proliferation of this cell line is dependent on EPO-R activation. The degree of cell proliferation was quantitated using MTT, where the signal in the MTT assay is proportional to the number of viable cells. The activity of a test peptide was measured by adding serial dilutions of the test peptide to cells, which were then incubated for 48 hours. After incubation, MTT was added to the cells, and absorbance was measured. The concentration of test peptide that results in a half-maximal absorbance, relative to that observed with EPO, was recorded as the EC50.

3. Competitive Binding Assay

Competitive binding calculations are made using an assay in which a light signal is generated as a function of the proximity of two beads: an EPO-conjugated bead and an EPO-R-conjugated bead. Bead proximity is generated by the binding of EPO to EPO-R. A test peptide that competes with EPO for binding to EPO-R will prevent this binding, causing a decrease in light emission. The concentration of test peptide that results in a 50% decrease in light emission, relative to that observed without test peptide, is recorded as the IC50.

4. C/BFU-e Assay

EPO-R signaling stimulates the differentiation of bone marrow stem cells into proliferating red blood cell presursors. This assay measured the ability of test peptides to stimulate the proliferation and differentiation of red blood cell precursors from primary human bone marrow pluripotent stem cells. Test peptides were added to cultures of human bone marrow cells, and the cells are incubated for 16 days. Thereafter, the number of red blood cell colonies were counted. The concentration of test peptide at which the number of formed colonies is 90% of maximum, relative to that observed with EPO, was recorded as the EC90.

| Compound | Reporter assay EC$_{50}$ (nM) | Proliferation assay EC$_{50}$ (nM) | C/BFUe assay EC$_{90}$ (nM) |
|---|---|---|---|
| Example 8 peptide (non-PEGylated) | 0.022 | 0.22 | 0.026 |
| Example 11 peptide (non-PEGylated) | 0.14 | 0.23 | — |
| Compound III (Example 8) | 0.20 | 0.14 | — |
| Compound IV (Example 10) | 0.32 | 0.19 | — |
| Compound V (Example 11) | 0.69 | 0.44 | 1.3 |
| Compound XIII (Example 19) | 0.70 | 0.36 | — |
| Compound I (Example 3) | 0.37 | 0.22 | 1.2 |

5. Polycythemic Exhypoxic Mouse Bioassay

Test peptides are assayed for in vivo activity in the polycythemic exhypoxic mouse bioassay adapted from the method described by Cotes and Bangham (1961), Nature 191: 1065-1067. This assay examines the ability of a test peptide to function as an EPO mimetic: i.e., to activate EPO-R and induce new red blood cell synthesis. Red blood cell synthesis is quantitated based upon incorporation of radiolabeled iron into hemoglobin of the synthesized red blood cells.

BDF1 mice are allowed to acclimate to ambient conditions for 7-10 days. Body weights are determined for all animals, and low weight animals (<15 grams) are not used. Mice are subjected to successive conditioning cycles in a hypobaric chamber for a total of 14 days. Each 24 hour cycle consists of 18 hr at 0.40±0.02% atmospheric pressure and 6 hr at ambient pressure. After conditioning the mice are maintained at ambient pressure for an additional 72 hr prior to dosing.

Test peptides, or recombinant human EPO standards, are diluted in PBS+0.1% BSA vehicle (PBS/BSA). Peptide monomer stock solutions are first solubilized in dimethyl sulfoxide (DMSO). Negative control groups include one group of mice injected with PBS/BSA alone, and one group injected with 1% DMSO. Each dose group contains 10 mice. Mice are injected subcutaneously (scruff of neck) with 0.5 mL of the appropriate sample.

Forty eight hours following sample injection, the mice are administered an intraperitoneal injection of 0.2 ml of Fe$^{59}$ (Dupont, NEN), for a dose of approximately 0.75 µCuries/mouse. Mouse body weights are determined 24 hr after Fe$^{59}$ administration, and the mice are sacrificed 48 hr after Fe$^{59}$ administration. Blood is collected from each animal by cardiac puncture and hematocrits are determined (heparin was used as the anticoagulant). Each blood sample (0.2 ml) is analyzed for Fe$^{59}$ incorporation using a Packard gamma counter. Non-responder mice (i.e., those mice with radioactive incorporation less than the negative control group) are eliminated from the appropriate data set. Mice that have hematocrit values less than 53% of the negative control group are also eliminated.

6. Hemoglobin and Reticulocyte Assays

Normocythemic male Sprague-Dawley rats were dosed at 10 mg/kg (1 mL/kg injection of a 10 mg/mL solution, injected intravenously) with test peptide formulated at pH 6.0 in phosphate buffer. At days 5, 9, 14, 19, 23, 28, 34, 43, and 57, blood samples were removed and hemoglobin levels were measured. FIGS. 1-4 illustrate the rise in hemoglobin over time for selected peptides of the Examples compared to the peptide of Example 3.

Also, the percent (%) reticulocytes for each blood sample was determined by thiazole orange staining and flow cytometer analysis (retic-count program). FIGS. 5-8 illustrate the rise in observed reticulocyte percent over time for selected peptides of the Examples compared to the peptide of Example 3.

Figure 9:
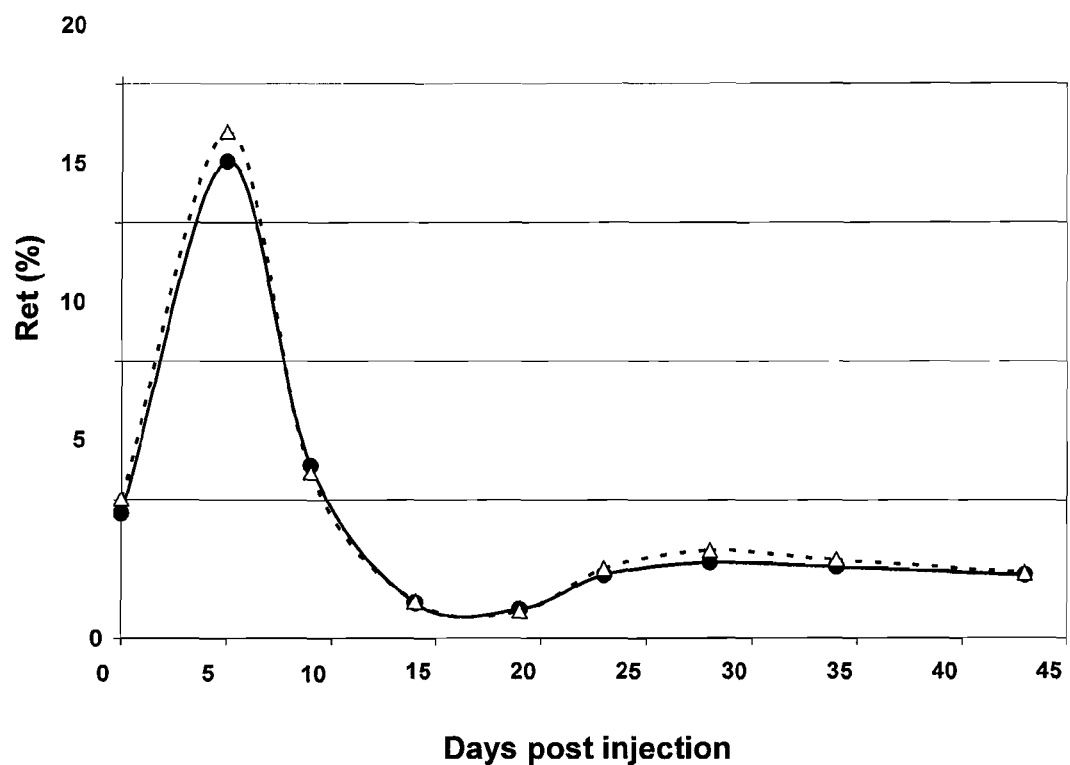
FIG. 9: Change in observed reticulocyte percent (Ret %) in male Sprague-Dawley rats after a single bolus administration of Compound XVI at 0.5 mg/kg. Dashed line (Δ): subcutaneous injection (SC); solid line (●): intravenous injection (IV).
Figure 10:
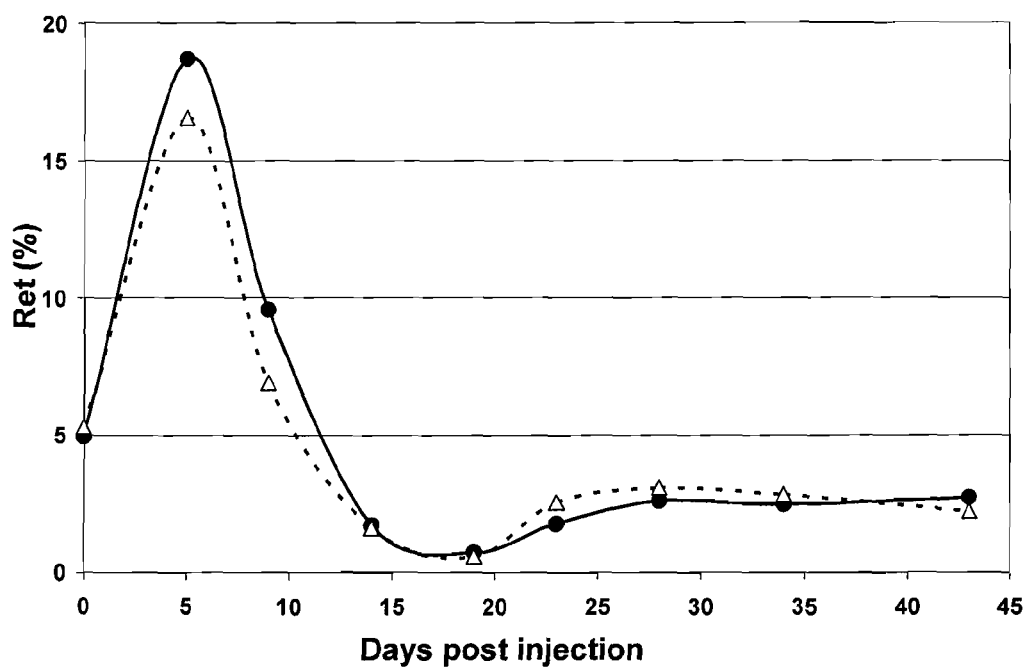
FIG. 10: Change in observed reticulocyte percent (Ret %) in male Sprague-Dawley rats after a single bolus administration of Compound XV at 0.5 mg/kg. Dashed line (Δ): subcutaneous injection (SC); solid line (●): intravenous injection (IV).
Figure 11:
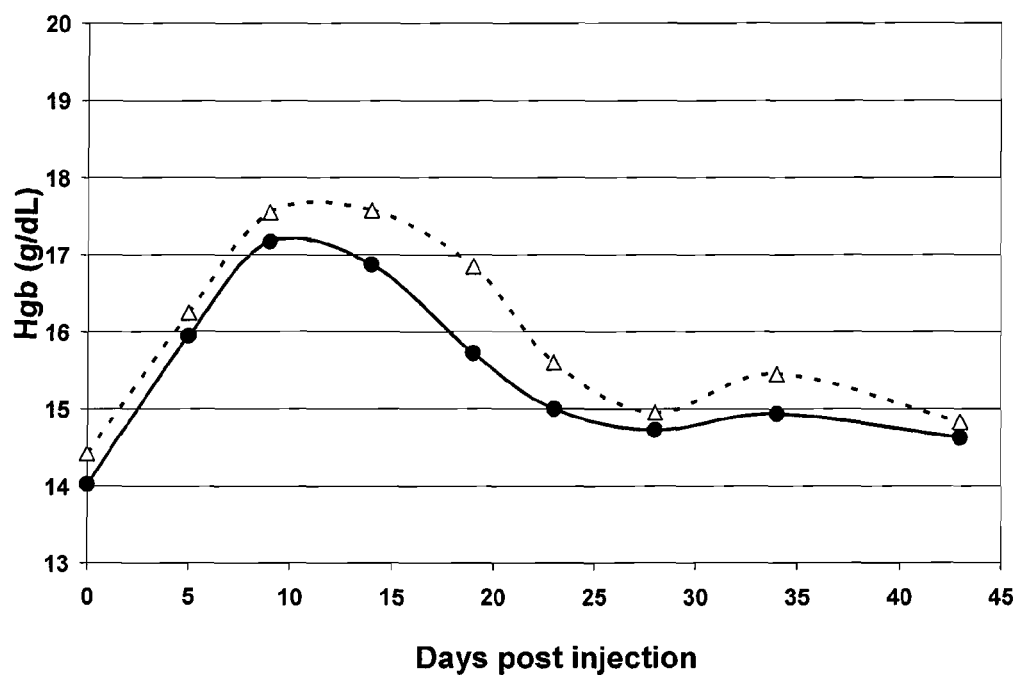
FIG. 11. Change in hemoglobin (Hgb) in male Sprague-Dawley rats after single bolus injection of Compound XVI at 0.5 mg/kg. Dashed line (Δ): subcutaneous injection (SC); solid line (●): intravenous injection (IV).
Figure 12:
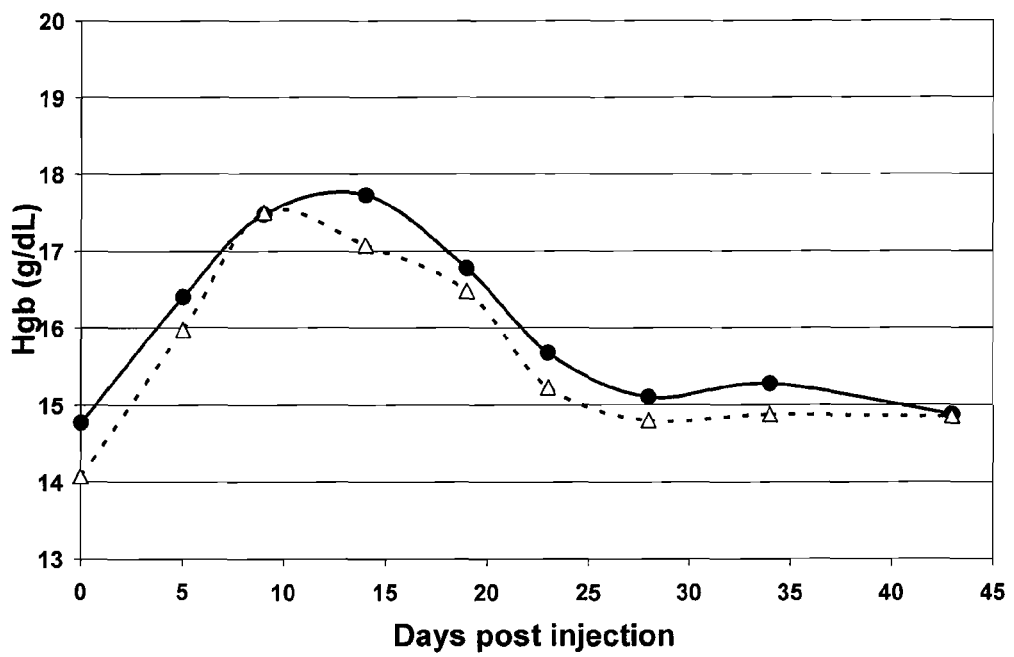
FIG. 12. Change in hemoglobin (Hgb) in male Sprague-Dawley rats after single bolus injection of Compound XV at 0.5 mg/kg. Dashed line (Δ): subcutaneous injection (SC); solid line (●): intravenous injection (IV).

Change in observed reticulocyte percent (Ret %) and hemoglobin (Hgb) in male Sprague-Dawley rats were measured for Compounds XV and XVI. Normocythemic male Sprague-Dawley rats were dosed at 10 mg/kg (1 mL/kg injection of a 10 mg/mL solution, injected intravenously or subcutaneously) with test peptide formulated at pH 6.0 in phosphate buffer. At days 5, 9, 14, 19, 23, 28, 34, 43, and 57, blood samples were removed. The percent (%) reticulocytes for each blood sample was determined by thiazole orange staining and flow cytometer analysis (retic-count program). These results are given in FIG. 9 for Compound XVI and FIG. 10 for Compound XV. Hemoglobin levels were measured at these time points and are shown in FIG. 11 for Compound XVI and FIG. 12 for Compound XV.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Numerous references, including patents, patent applications, protocols and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

SEQUENCE LISTING

```
<160> NUMBER OF SEQ ID NOS: 28

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

-continued

```
<222> LOCATION: (2)
<223> OTHER INFORMATION: Arg, His, Leu or Trp
<220> FEATURE:
<221> NAME/KEY: MOD_RES
<222> LOCATION: (3)
<223> OTHER INFORMATION: Met, Phe, Tyr or Ile
<220> FEATURE:
<221> NAME/KEY: MOD_RES
<222> LOCATION: (6)
<223> OTHER INFORMATION: any one of the 20 genetically encoded L-amino
      acids
<220> FEATURE:
<221> NAME/KEY: MOD_RES
<222> LOCATION: (9)
<223> OTHER INFORMATION: Asp, Glu, Ile, Leu or Val

<400> SEQUENCE: 1

Cys Xaa Xaa Gly Pro Xaa Thr Trp Xaa Cys
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Trp, 1-Nal or 2-Nal

<400> SEQUENCE: 2

Leu Tyr Ala Cys His Met Gly Pro Ile Thr Xaa Val Cys Gln Pro Leu
1               5                   10                  15

Arg

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (14)
<223> OTHER INFORMATION: Sar
<220> FEATURE:
<223> OTHER INFORMATION: n-term acetylation

<400> SEQUENCE: 3

Ile Glu Gly Pro Thr Leu Arg Gln Xaa Leu Ala Ala Arg Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Sar
<220> FEATURE:
<223> OTHER INFORMATION: n-term acetylation
```

-continued

```
<400> SEQUENCE: 4

Ile Glu Gly Pro Thr Leu Arg Gln Trp Leu Ala Ala Arg Xaa
1               5                   10

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal
<220> FEATURE:
<221> NAME/KEY: MOD_RES
<222> LOCATION: (20)
<223> OTHER INFORMATION: Sar
<220> FEATURE:
<223> OTHER INFORMATION: n-term acetylation

<400> SEQUENCE: 5

Gly Gly Leu Tyr Ala Cys His Met Gly Pro Ile Thr Xaa Val Cys Gln
1               5                   10                  15

Pro Leu Arg Xaa Lys
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal
<220> FEATURE:
<223> OTHER INFORMATION: n-term acetylation

<400> SEQUENCE: 6

Gly Gly Leu Tyr Ala Cys His Met Gly Pro Ile Thr Xaa Val Cys Gln
1               5                   10                  15

Pro Leu Arg Lys
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 1-Nal
<220> FEATURE:
<221> NAME/KEY: MOD_RES
<222> LOCATION: (19)
<223> OTHER INFORMATION: Sar
<220> FEATURE:
<223> OTHER INFORMATION: n-term acetylation

<400> SEQUENCE: 7

Gly Leu Tyr Ala Cys His Met Gly Pro Ile Thr Xaa Val Cys Gln Pro
1               5                   10                  15

Leu Arg Xaa Lys
```

-continued

```
<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: 1-Nal
<220> FEATURE:
<221> NAME/KEY: MOD_RES
<222> LOCATION: (18)
<223> OTHER INFORMATION: Sar
<220> FEATURE:
<223> OTHER INFORMATION: n-term acetylation

<400> SEQUENCE: 8

Leu Tyr Ala Cys His Met Gly Pro Ile Thr Xaa Val Cys Gln Pro Leu
1               5                   10                  15

Arg Xaa Lys

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 1-Nal
<220> FEATURE:
<223> OTHER INFORMATION: n-term acetylation

<400> SEQUENCE: 9

Gly Leu Tyr Ala Cys His Met Gly Pro Ile Thr Xaa Val Cys Gln Pro
1               5                   10                  15

Leu Arg Lys

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: 1-Nal
<220> FEATURE:
<223> OTHER INFORMATION: n-term acetylation

<400> SEQUENCE: 10

Leu Tyr Ala Cys His Met Gly Pro Ile Thr Xaa Val Cys Gln Pro Leu
1               5                   10                  15

Arg Lys

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (13)
<223> OTHER INFORMATION: 1-Nal
<220> FEATURE:
<221> NAME/KEY: MOD_RES
<222> LOCATION: (20)
<223> OTHER INFORMATION: Sar
<220> FEATURE:
<223> OTHER INFORMATION: n-term acetylation

<400> SEQUENCE: 11

Gly Gly Leu Tyr Leu Cys Arg Tyr Gly Pro Val Thr Xaa Glu Cys Gln
1               5                   10                  15

Pro Arg Arg Xaa Lys
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal
<220> FEATURE:
<223> OTHER INFORMATION: n-term acetylation

<400> SEQUENCE: 12

Gly Gly Leu Tyr Leu Cys Arg Tyr Gly Pro Val Thr Xaa Glu Cys Gln
1               5                   10                  15

Pro Arg Arg Lys
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 1-Nal
<220> FEATURE:
<221> NAME/KEY: MOD_RES
<222> LOCATION: (19)
<223> OTHER INFORMATION: Sar
<220> FEATURE:
<223> OTHER INFORMATION: n-term acetylation

<400> SEQUENCE: 13

Gly Leu Tyr Leu Cys Arg Tyr Gly Pro Val Thr Xaa Glu Cys Gln Pro
1               5                   10                  15

Arg Arg Xaa Lys
            20

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
```

```
<223> OTHER INFORMATION: 1-Nal
<220> FEATURE:
<221> NAME/KEY: MOD_RES
<222> LOCATION: (18)
<223> OTHER INFORMATION: Sar
<220> FEATURE:
<223> OTHER INFORMATION: n-term acetylation

<400> SEQUENCE: 14

Leu Tyr Leu Cys Arg Tyr Gly Pro Val Thr Xaa Glu Cys Gln Pro Arg
 1               5                  10                  15

Arg Xaa Lys

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 1-Nal
<220> FEATURE:
<223> OTHER INFORMATION: n-term acetylation

<400> SEQUENCE: 15

Gly Leu Tyr Leu Cys Arg Tyr Gly Pro Val Thr Xaa Glu Cys Gln Pro
 1               5                  10                  15

Arg Arg Lys

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: 1-Nal
<220> FEATURE:
<223> OTHER INFORMATION: n-term acetylation

<400> SEQUENCE: 16

Leu Tyr Leu Cys Arg Tyr Gly Pro Val Thr Xaa Glu Cys Gln Pro Arg
 1               5                  10                  15

Arg Lys

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal
<220> FEATURE:
<223> OTHER INFORMATION: n-term acetylation

<400> SEQUENCE: 17

Gly Gly Thr Tyr Ser Cys His Phe Gly Pro Leu Thr Xaa Val Cys Arg
 1               5                  10                  15

Pro Gln Gly Gly Lys
```

-continued

```
<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal
<220> FEATURE:
<223> OTHER INFORMATION: n-term acetylation

<400> SEQUENCE: 18

Gly Gly Thr Tyr Ser Cys His Phe Gly Pro Leu Thr Xaa Val Cys Arg
 1               5                  10                  15

Pro Gln Gly Lys
            20

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal
<220> FEATURE:
<223> OTHER INFORMATION: n-term acetylation

<400> SEQUENCE: 19

Gly Gly Thr Tyr Ser Cys His Phe Gly Pro Leu Thr Xaa Val Cys Arg
 1               5                  10                  15

Pro Gln Lys

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 1-Nal
<220> FEATURE:
<223> OTHER INFORMATION: n-term acetylation

<400> SEQUENCE: 20

Gly Thr Tyr Ser Cys His Phe Gly Pro Leu Thr Xaa Val Cys Arg Pro
 1               5                  10                  15

Gln Gly Gly Lys
            20

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (11)
<223> OTHER INFORMATION: 1-Nal
<220> FEATURE:
<223> OTHER INFORMATION: n-term acetylation

<400> SEQUENCE: 21

Thr Tyr Ser Cys His Phe Gly Pro Leu Thr Xaa Val Cys Arg Pro Gln
 1               5                  10                  15

Gly Gly Lys

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 1-Nal
<220> FEATURE:
<223> OTHER INFORMATION: n-term acetylation

<400> SEQUENCE: 22

Gly Thr Tyr Ser Cys His Phe Gly Pro Leu Thr Xaa Val Cys Arg Pro
 1               5                  10                  15

Gln Gly Lys

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal
<220> FEATURE:
<221> NAME/KEY: MOD_RES
<222> LOCATION: (20)
<223> OTHER INFORMATION: Sar
<220> FEATURE:
<223> OTHER INFORMATION: n-term acetylation

<400> SEQUENCE: 23

Gly Gly Leu Tyr Ala Cys His Tyr Gly Pro Ile Thr Xaa Val Cys Gln
 1               5                  10                  15

Pro Leu Arg Xaa Lys
                20

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylation

<400> SEQUENCE: 24

Gly Gly Thr Tyr Ser Cys His Phe Gly Pro Leu Thr Trp Val Cys Arg
 1               5                  10                  15

Pro Gln Gly Gly Lys
                20
```

-continued

```
<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: 1-Nal
<220> FEATURE:
<221> NAME/KEY: MOD_RES
<222> LOCATION: (21)
<223> OTHER INFORMATION: Sar
<220> FEATURE:
<223> OTHER INFORMATION: c-term amidation

<400> SEQUENCE: 25

Lys Gly Gly Leu Tyr Ala Cys His Met Gly Pro Ile Thr Xaa Val Cys
1               5                   10                  15

Gln Pro Leu Arg Xaa
            20

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term may have allyloxycarbonyl protecting
      group

<400> SEQUENCE: 26

Gly Gly Leu Tyr Ala Cys His Met Gly Pro Met Thr Trp Val Cys Gln
1               5                   10                  15

Pro Leu Arg Gly Lys
            20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term may have allyloxycarbonyl protecting
      group

<400> SEQUENCE: 27

Gly Gly Thr Tyr Ser Cys His Phe Gly Pro Leu Thr Trp Val Cys Lys
1               5                   10                  15

Pro Gln Gly Gly Lys
            20

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: 1-Nal
<220> FEATURE:
```

```
<223> OTHER INFORMATION: n-term acetylation

<400> SEQUENCE: 28

Leu Tyr Leu Cys Arg Tyr Gly Pro Val Thr Xaa Glu Cys Gln Pro Leu
1               5                   10                  15

Arg Lys
```

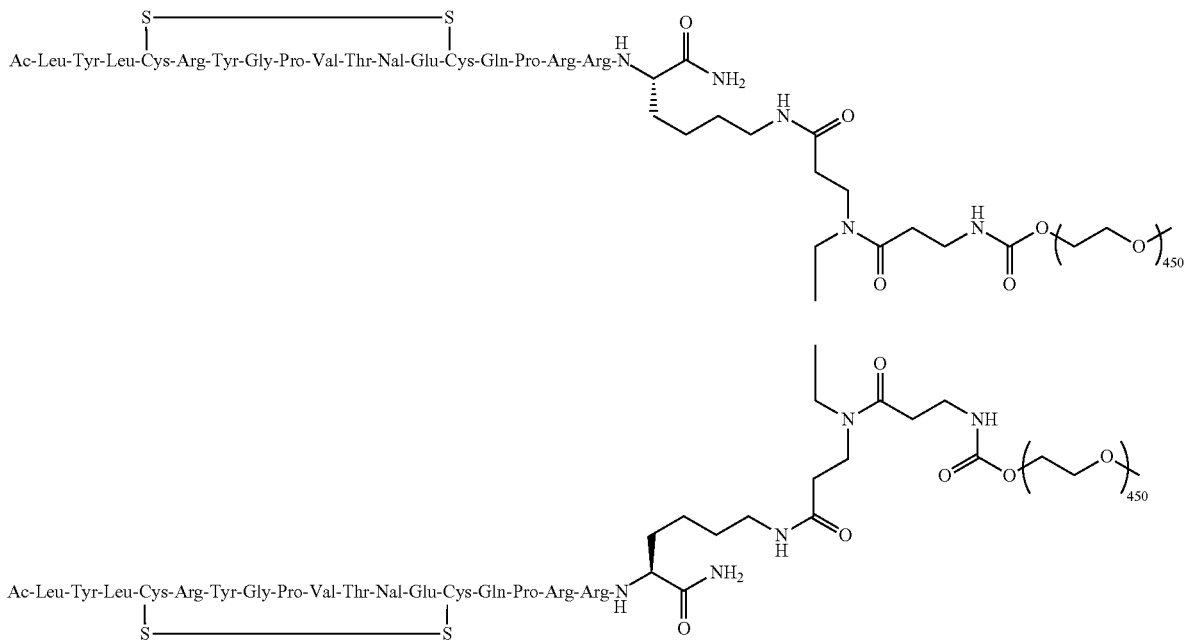

4. A compound that binds to and activates the erythropoietin receptor (EPO-R), which compound comprises a peptide dimer (SEQ ID NO: 16) having the formula:
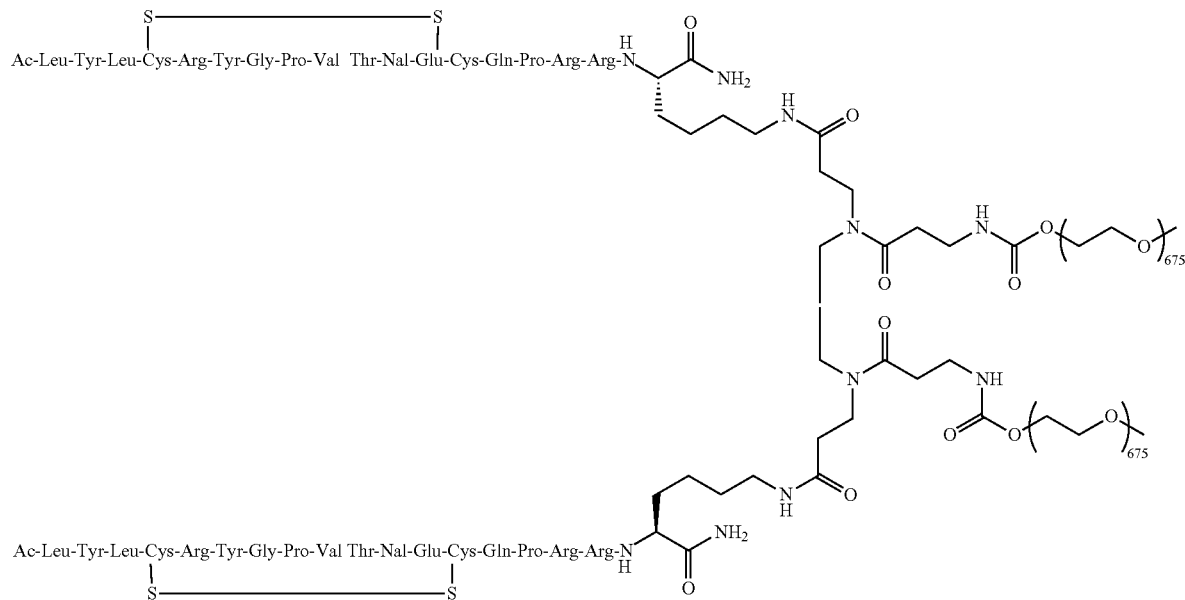

What is claimed is:

1. A linker moiety compound, wherein the linker moiety compound has the structure:

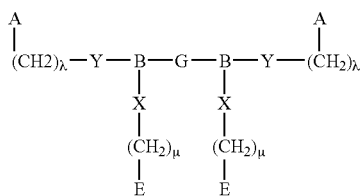

wherein
- each $\lambda$ is an integer having a value independently selected from $1 \leq \lambda \leq 4$;
- each $\mu$ is an integer having a value independently selected from $2 \leq \mu \leq 4$;
- each A is independently selected from the group consisting of $CO_2H$, activated $CO_2H$, $NH_2$, NCO, CHO, maleimide, and vinyl sulfone;
- each B is independently selected from the group consisting of CH and N;
- each G is independently selected from the group consisting of $(CH_2)_v$, CO and $COCH_2OCH_2CO$;
- each E is independently selected from the group consisting of $NH_2$, NHBoc, $CO_2H$, CHO, and maleimide;
- each X is independently selected from the group consisting of CO, bond, and CONH;
- each Y is independently selected from the group consisting of CO, bond, and NHCO; and
- each v is an integer having a value independently selected from $2 \leq v \leq 4$.

2. The linker moiety compound of claim 1, wherein
- each $\lambda$ is an integer having a value independently selected from $1 \leq \lambda \leq 3$;
- each $\mu$=2;
- each A is independently selected from the group consisting of $CO_2H$ and activated $CO_2H$;
- each B is N;
- each G is independently selected from the group consisting of $(CH_2)_v$, CO and $COCH_2OCH_2CO$;
- each E is independently selected from the group consisting of $NH_2$ or NHBoc;
- each X is independently selected from the group consisting of CO and bond;
- each Y is independently selected from the group consisting of CO and bond; and
- each v=2.

3. A compound that binds to and activates the erythropoietin receptor (EPO-R), which compound comprises a peptide dimer (SEQ ID NO: 16) having the formula: